United States Patent [19]

Rosenberg

[11] Patent Number: 4,763,282
[45] Date of Patent: Aug. 9, 1988

[54] PROGRAMMING FORMAT AND APPARATUS FOR THE IMPROVED COHERENT BEAM COUPLER SYSTEM AND METHOD

[76] Inventor: Larry Rosenberg, 3440 Caroline Ave., Culver City, Calif. 90230

[21] Appl. No.: 798,011

[22] Filed: Nov. 14, 1985

Related U.S. Application Data

[63] Continuation-in-part of Ser. No. 498,773, May 27, 1983, Pat. No. 4,589,078.

[51] Int. Cl.$^4$ .................. G06F 15/20; G05B 19/00
[52] U.S. Cl. .................. 364/524; 128/633; 604/20; 364/415
[58] Field of Search .......... 364/524, 525, 413, 414, 364/415, 555; 128/633, 395, 2 G, 303.1, 634, 635, 664, 665; 604/20, 48, 49, 50, 65, 66, 67

[56] References Cited

U.S. PATENT DOCUMENTS

| | | | |
|---|---|---|---|
| Re. 31,879 | 5/1985 | Lübbers et al. | 128/665 |
| 3,703,726 | 11/1972 | Stephenson | 364/300 |
| 3,748,044 | 7/1973 | Liston | 364/525 |
| 3,914,013 | 11/1975 | Rosenberg | 350/96.24 |
| 4,350,163 | 9/1982 | Ford, Jr. et al. | 128/633 |
| 4,392,849 | 7/1983 | Petre et al. | 604/50 |
| 4,538,613 | 9/1985 | Rosenberg | 128/395 |
| 4,556,057 | 12/1985 | Hiruma et al. | 604/20 |
| 4,576,173 | 3/1986 | Parker et al. | 128/633 |
| 4,589,078 | 5/1986 | Rosenberg | 364/524 |
| 4,633,872 | 1/1987 | Chaffee et al. | 128/303.1 |
| 4,638,456 | 1/1987 | Elias et al. | 364/415 |
| 4,641,650 | 2/1987 | Mok | 128/303.1 |
| 4,672,963 | 6/1987 | Barken | 128/303.1 |
| 4,696,671 | 9/1987 | Epstein et al. | 604/67 |

OTHER PUBLICATIONS

Watkins and Holloway, Jr., An Instrument to Measure Cutaneous Blood Flow Using the Doppler Shift of Laser Light, ©1978, IEEE Transactions on Biomedical Engineering, vol. BME-25, No. 1, Jan. 1978, pp. 28–33.

Olson et al., Computer-Controlled Electrophoresis Microscope, 1980, pp. 54–61, SPIE, vol. 232, 1980 International Optical Computing Conference.

Halaby and Vance, Computer-Controlled Spectral Measurements of Blood Cells, ©1979, pp. 34–43, IEEE Transactions on Biomedical Engineering, vol. BME-26, No. 1, Jan. 1979.

Primary Examiner—Parshotam S. Lall
Assistant Examiner—Steven A. Melnick
Attorney, Agent, or Firm—Malke Leah Bas Meyer Itzhak Ben Shlomo

[57] ABSTRACT

A novel and innovative series of programs are deployed to actuate and control the novel embodiment of an automated laser wave detection and emissive delivery system known as the Improved Coherent Beam Coupler which is useful in surgical operations and high resolution analytic procedures. The programs are collectively designed to provide the highest resolution of optical electronic spectra data and to promote the fastest most reliable response time necessary to control the electronic composition, dispersal, and wave amplitude modulation of emissive sources. High energy multiple emissions are generated in discrete steps which are specified by impulses derived or obtained from an array of feedback sensors. The necessary tactical and logistic information necessary to engage target loci, analyze specific chemical species or any associated processes are specified by pre-existing data contained within the existing framework of readily accessible programs. Contained within the body or framework of the programming network is the capacity to make rapid and very specific alterations in the operations of subsystems of the Improved coherent Beam Coupler based on digitized feedback signals obtained from the array of sensors. The added capability to key on the spot modifications in the programming sequence is an essential process when dealing with nonhomogenous systems which are subjected to conditions of dynamic flux.

4 Claims, 50 Drawing Sheets

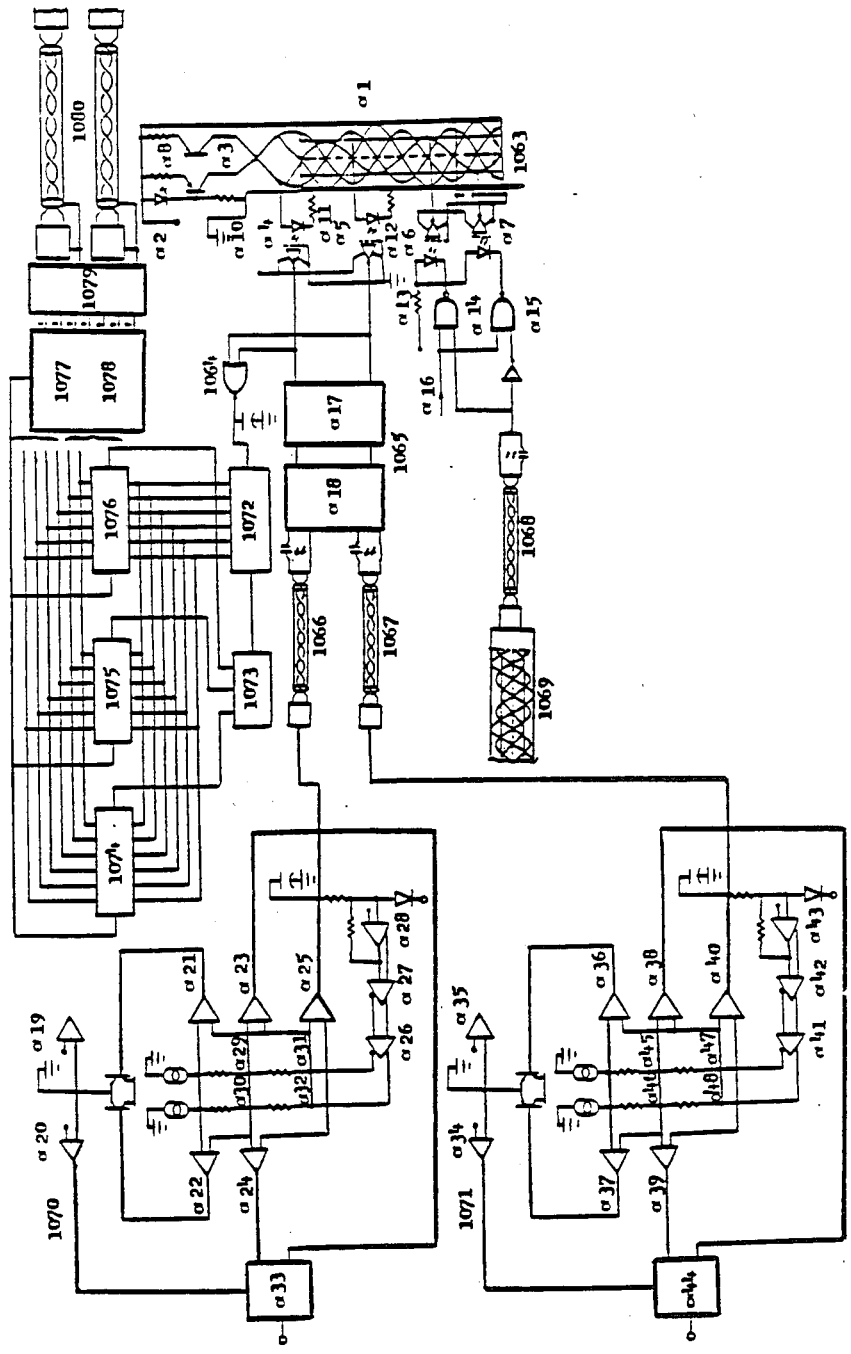

PROGRAMMING FORMAT AND APPARATUS FOR THE IMPROVED COHERENT BEAM COUPLER SYSTEM AND METHOD

This application is a continuation-in-part of U.S. application Ser. No. 498,773 filed May 27, 1983, now U.S. Pat. No. 4,589,078.

BACKGROUND OF THE INVENTION

1. Field of the Invention

The invention consists of a series of quantitative numerical programs designed to control electronic subsystems of an improved version of a device known as the Coherent Radiation Beam Coupler, a mechanism specifically constructed to control and or modify the electronic characteristics, the deposition and the subsequent delivery of coherent radiation or other forms of emissions, to a given loci or mode of operation. The Improved Coherent Beam Coupler alters emissive sources in a manner as to specifically perform certain well defined analytic operations such as those concerned with laser doppler analysis, or to inact a wide variety of quantitative surgical procedures and industrial applications. More specifically the present scope of the invention coordinates a series of complex flexable programs and subroutines which are of an interactive nature, in order to provide numerous microprocessors or their equivalents with the optimal response necessary to solve a multitude of complex numerical operations simultaneously and to achieve the particular desired effect.

2. Description of the Prior Art

Examples of existing systems are represented by U.S. Pat. No. 3,914,013 Coherent Radiation Beam Coupler issued to the inventor hereof and publications Laser Imaging, Departiclization, and Analysis A Relatively Noninvasive Means ISBN#0-935536-25-6 Copyright 1982.

The earlier versions of the Coupler device had a complement of at least two, but no more than six microprocessors restricting the implementation of each unit to its respective subsystem. Of late while the microprocessors allowed the Coupler apparatus to provide a large scale integration of the various subsystems each unit functioned independently from the rest in fixed modes of operation. The effectiveness of beam amplification, dispersal and wave characteristic modification relied on the collective operation of each keyed microprocessor, and the judgment and speed of the system's human operator. Each subsystem had the option of functioning either in succession or synchronously with each other system, with no variations in between the two extremes. The exposure interval, electronic wave characteristics, amplification, and dispersal or other properties of the said beams had to be precisely programmed and exacted separately or independently from the preceding operational mode.

The conventional Beam Coupler device had been limited to a series of one step single microprocessor operations each of which is confined to its own specific fixed program, such that the data entering from various sensory apparatus had to be independently collated with each of the subsystems restricting both the speed and the accuracy of the entire Coherent Radiation Beam Coupler unit. One or more microprocessors have been employed for controlling the entry of data through a key matrix and the remaining microprocessors were utilized for controlling various aspects of the high energy emissions a display, a storage and the like serving as a load of a given processor. A more preferred embodiment of programming is in a self actuated microcomputer with an automated feedback system compiler and signal digitizer, which can rapidly initiate the necessary adjustments of the said transmission source, while all systems are in operation. A further essential element of the preferred embodiment would most certainly be the capacity to make frequent on the spot corrections or alterations in the fixed encoded program instructions governing each subsystem of the unit as ambient conditions of the target loci changed their respective physical states. Smooth variations between one state of matter to the next or the Kinetic dynamics thereof, could not be attained sufficiently to satisfy all necessary time dependent conditions. The advent of EEPROM or equivalent system ideally provide programming flexibility which was hereto unattainable by previous coupler devices with rigid programming formats.

SUMMARY OF THE INVENTION

The present invention is characterized by the deployment of commercially available microcomputers equipped with enhanced programming capabilities governing the processing of all data as well as the operation of the Improved Coherent Beam Coupler unit proper. An optical electronic analog digital converter provides direct system interphase between the commercially available microcomputers, coupler device and any ancillary system, in order to enhance signals either re-emitted or reflected from a given target site, and in doing so limits the signals distortion significantly in such processes as doppler analysis. Various types of unique control parameters and novel command conditions are provided to amplify, control, direct, or otherwise alter specified wave characteristics of one or more emissive sources, as to optimally engage one or more target loci. Each target loci or site when subjected to an intense localized emissive bombardment re-emits and or reflects specific energy emissions which are characteristic of the size, density, and chemical composition of the effective target area. It is the complex nature of the specialized program revealed by the flow diagrams presented in this disclosure, which provides for continuous scanning of all pertinent parameters, data reaccessment, and the effective operation of all subsystems based on current sensory feedback entries.

According to the present invention all digitized data entries are converted into their primary binary equivalents and sorted or classifiec on the basis of statistical constructs, with those values indexed in the system's memory banks. Variation of the Maximum Likelyhood Method, Optimal Probability and or the Best Fit Method provide the statistical basis whereby signals in the form of retrieved optical electronic sensory data are exacted and indexed, in order to effect a match with stored values representing known substances. Each known substance is further classified on the basis of behavioral effects of such attributes as concentration electric mobility, internal resonance, and thermal, kinetic or other well defined parameters.

The preferred embodiment of the present invention employs stochastic acquisition and pursuit programs which are instrumental in homing in and locking on various chemical substances, emitted by the target site.

In another preferred embodiment of the present invention programs are enlisted to stabilize wide variations in temperature and pressure as well as subtle changes in chemical properties such as those concerning the equalisation of pH through the initiation of a Normalization Innovation Process:

Accordingly ambient chemical, thermal, and pressure parameters are maintained by certain specific compensatory processes pertaining to a novel infusion technique in conjunction with a novel laser bombardment process defined as departiclization.*

*is also known as departicalization

Another object of the present invention is to provide the immediate implementation and execution of selected programs each of which is carried out in discrete steps either sequentially or simultaneously.

A further object of the present invention concerns the capacity to make immediate modifications in the programming when confronted with new or novel situations. The EEPROM element provides a compensatory means to adjust the operation of the entire apparatus with a few simple keying instructions from the human operator.

Still a further object of the present invention is to utilize the programming versatility to optimize the delivery of certain electronic wave characteristics, their dispersal and alike to the target site, while minimizing the effect to surrounding areas in the immediate vicinity of the target area.

Still another object of the present invention is the capacity of the unit to automaticly relinquish control of one or more subsystems to the user for keying specific modes of operation if warranted, without interrupting the operation of one or all subsystems comprising the device.

The objects mentioned herein the above and other objects, features, aspects and advantages of this present invention will become increasingly apparent from the following detailed description of the preferred embodiments and annexed drawings.

BRIEF DESCRIPTION OF THE DRAWINGS

FIG. 44 is a combination block diagram and schematical representation in which only one of several optical electronic analog/digital converter units employed by the coupler device;

DESCRIPTION OF THE PREFERRED EMBODIMENT

In the following detailed description of the preferred embodiment of the present invention, the present invention will be advantageously described within the distinct contexts of the Coherent Beam Coupler System. However, the operation of the present invention should not be limited or restricted solely to the exclusive embodiment of the Improved Beam Coupler System, but rather the present scope of the invention can be employed in any one of several Coherent Radiation Beam Coupler devices or other similar such apparatus used for altering the content, electronic characteristics or disposition of given emissive sources an the like.

Figure 1:
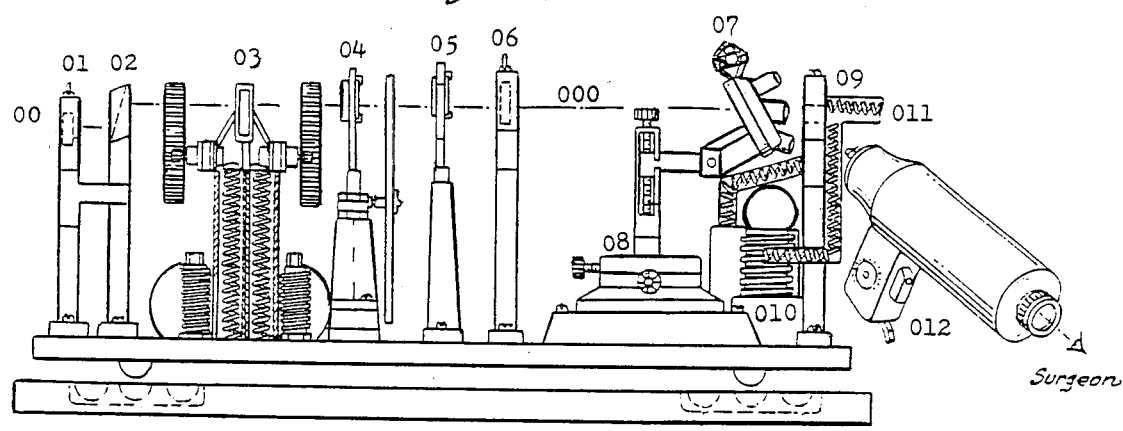
FIG. 1 is a side elevation of the Improved Coherent Beam Coupler revealing a perspective view of the apparatus in which the present invention can be advantageously employed.

FIG. 1 is a perspective view exposing a side elevation of the Improved Coherent Beam Coupler. A given emissive source entering along axis 00 is engaged by a electronic diaphragm 01 and then passes through one of four equivalent automated beam splitters 02, which directs the said beam down the central axis 000 of device onto the automated dye cell complex 03. The beam upon exiting the automated dye cell complex 03 is intercepted by one or more automated elements of the electronic chopper complex 04 where upon the said emission beam departing from the chopper complex might be further acted upon by electronic shutter means 05 or electronic diaphragm 06. A multiple lense turret system 07 is automated to focus on one or more emissive beams along the central axis 000. The turret system is mounted on an automated X, Y, Z translational stage denoted by numerial 08 which focuses the emissive beams onto a fiber optic element 09. An automated infusion aspiration pump 010 is adjacent to the translational stage means and transfers its contents circumferentially along the outer peripherial axis of fiber optics element 09. The contents of pump unit 010 and fiber optics element 09 are both housed in conduit 011. Spectral data imaging and alike maybe sampled almost directly by a return self focusing fiber optics system 012.

Figure 2:
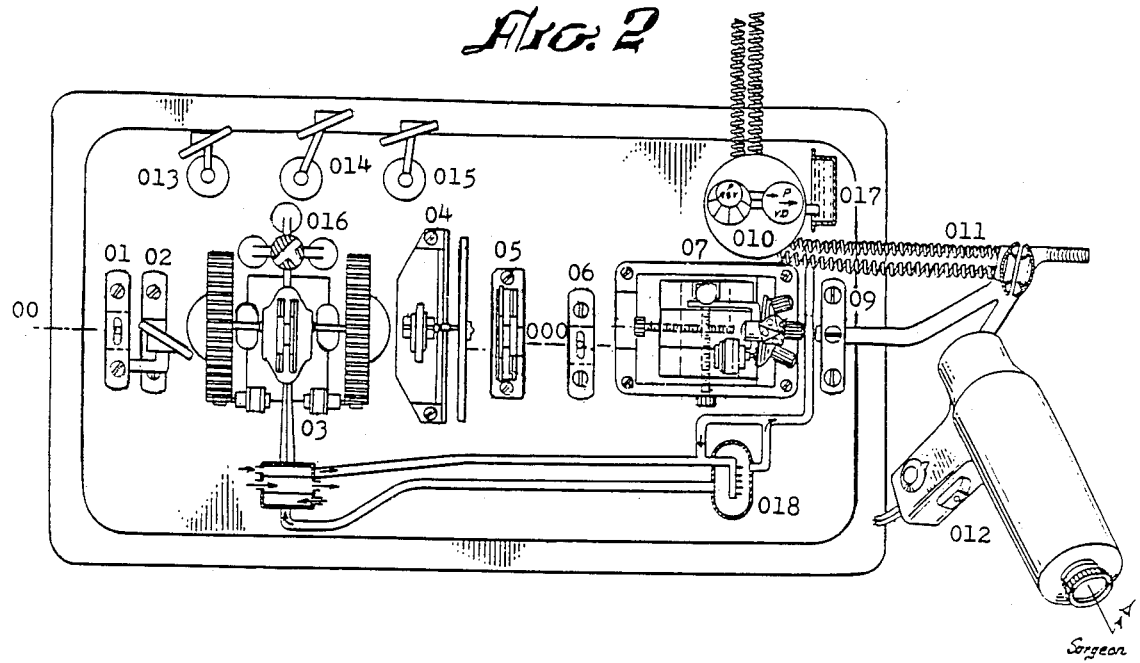
FIG. 2 is a plan topographical view of the system depicted in FIG. 1.

FIG. 2 consists of a topographical view of the apparatus as depicted in FIG. 1. The subsystems are disclosed by the overview. Numerals 013, 014, and 015 represent the remaining complement of a automated beam splitting and 016 denotes a complex of dye containing reservoirs. Additional reservoirs are denoted by 017 and 018. The contents expended by each of the reservoirs is cycled to a common heat exchanger means 019.

Figure 3:
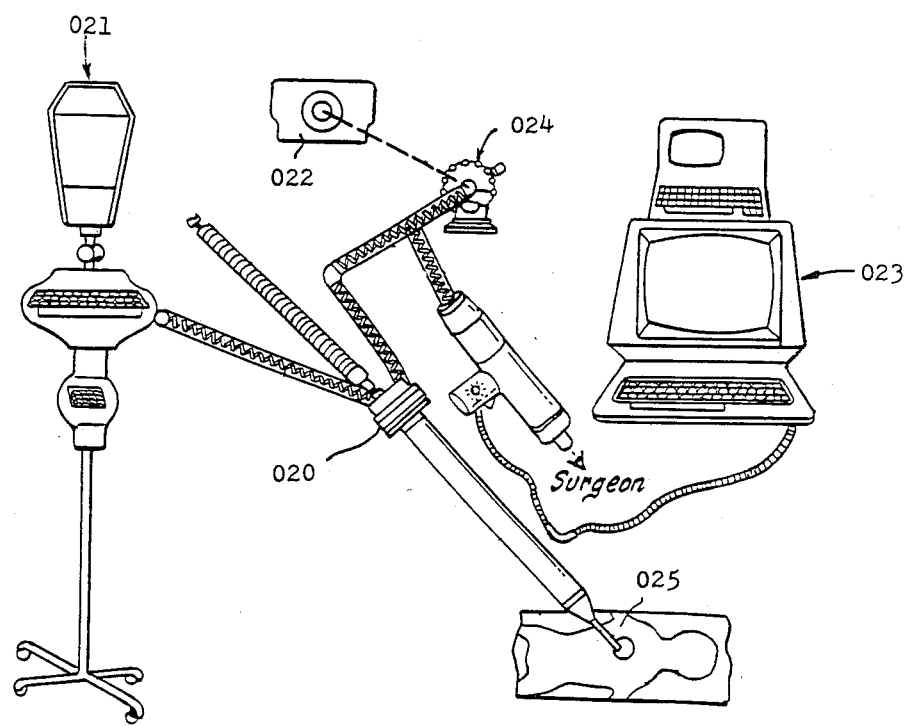
FIG. 3 is a perspective view of the tactical logistic support unit to supply infusion, aspiration, and or the insertion of a portion of the Coupler into a target region.

FIG. 3 offers a prespective view of the tactical logistic support unit which provides for the insertion of conduit 011 into a given target area. A automated hydraulic insertion autofeed system denoted by numeral 020 has the capacity to advance or withdraw conduit 011. Additional infustion or aspiration as well as the introduction of buffering agents, hemoglobin, blood plasma and the like can be introduced by an additional automated reservoir complex unit 021. Numerals 022, 023, and 024 describe a given emissive source, the coupler device and an enhanced video display terminal to monitor all systems operations.

Figure 4:
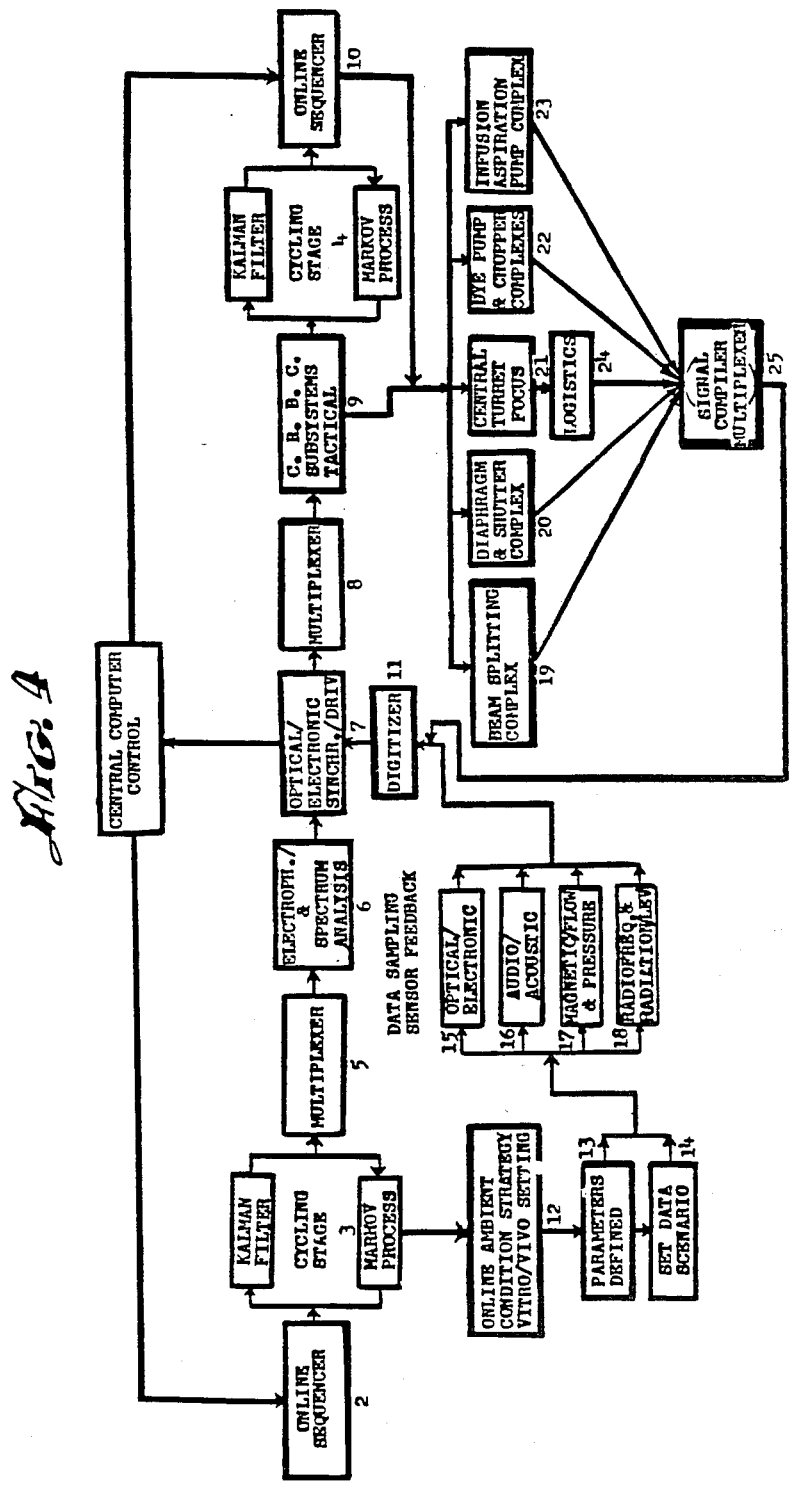
FIG. 4 is a simplified block diagram and schematic representation of the entire complement of online systems governed by the preferred embodiment of the present invention.

FIG. 4 depicts in a block diagram fashion the entire complement of systems deployed for laser departiclization, doppler analysis and any related processes. Specific optical electronic data and instructions are sent divergently by a Central Computer Control, 1, to the online sequencers, 2 and 10 respectively. Both the signals entering the main sequence from element 2, or those signals sent to the peripheral system by element 10 are digitized and filtered cyclicly by systems 3 and 4, in order to eliminate white noise or other forms of distortion. Once specific signals are separated and free from distortion they are multiplexed by the multiplexer unit 5. Optical electronic signals sent by multiplexer 5 are received by unit 6 where spectral analysis occurs by a complex of automated interferometers, micrometers, multichannel analyzers and the like. Electronic data received from microspectral electrophoresis is analyzed by charge column separators, electronic field oscillators and the like. Impulses are conveyed by optical electronic unit 6 to a bidirectional optical electronic compiler element 7. The complex signals derived from the compiler 7 are conveyed to a multiplexer 8 which directly sends the online information to a microcomputer associated with the coupler device and concerned with tactical operations denoted by element 9. The microcomputer employed to control onboard systems operations for the Coupler is the SDK-86, a commercially available unit with a rapid turn around time and EEPROM capabilities. A number of equivalent systems are now commonly available from several other manufactures. Optical electronic signals are conveyed to subsystems of the Coupler device and to a online sequencer 10, via cyclic filter system 4. Additional instructions are sent by the Central Computer Control unit, 1, to element 10, whereby the signals are passed along to the Couplers subsystems along the same route which is employed by tactical element 9.

Numerals 19 through 23 denote specific operational subsystems of the Coupler unit. The beam splitter complex is represented by number 19, and the diaphragm shutter control complex is denoted by number 20. Numerals 22 and 23 represents the dye pump chopper complex and the infusion aspiration pump means respectively. The central focusing turret of the device is represented by number 21 and it is associated with a sensor array incorporating a logistics control means designated by the number 24. All feedback data channeled from subsystems 19 through 24 is collectively sent to the signal compiler multiplexer unit 25, which in turn sends its input to a digitizer means 11. The digitizer 11 conveys its data to the optical electronic synchronous drive element, and or compiler 7 where its transferred to the Central Computer to be acted upon further. Returning command signals are sent from the Central Control Computer 1 to the first of two online sequencers 2, which transfers the data to filter element 3 where the divergent data is cycled and passed to multiplexer 5 and 12 respectively. Numeral 12 represents a second microcomputer which provides a file of online ambient conditions and strategies necessary to inact a proper chain of command when dealing with either vitro or vivo conditions. The output from element 12 is received by unit 13 where specifications are indexed for given parameters. A particular course of action or means of monitoring a given target area is choosen by a priority system 14. The output of 13 and 14 are combined and sent to a complex of sensory means denoted collectively by numbers 15 through 18. The data sampling sensor feedback systems is as follows; number 15 represents all optical electronic sensors; 16 denotes audio acoustic sensors which incorporate ultrasound; numeral 17 depicts various magnetic flow and tension pressure sensors; and finally a series of radio frequency and radiation detection sensor devices are represented by element 18. All sensory data collected from the data sampling sensor feedback system denoted by numerals 15 through 18 are collectively sent to the digitizer unit 11 where they are separated, prepared, and then transmitted to the optical electronic compiler means 7, which returns the output data to the Central Computer Control Complex for processing.

Figure 5:
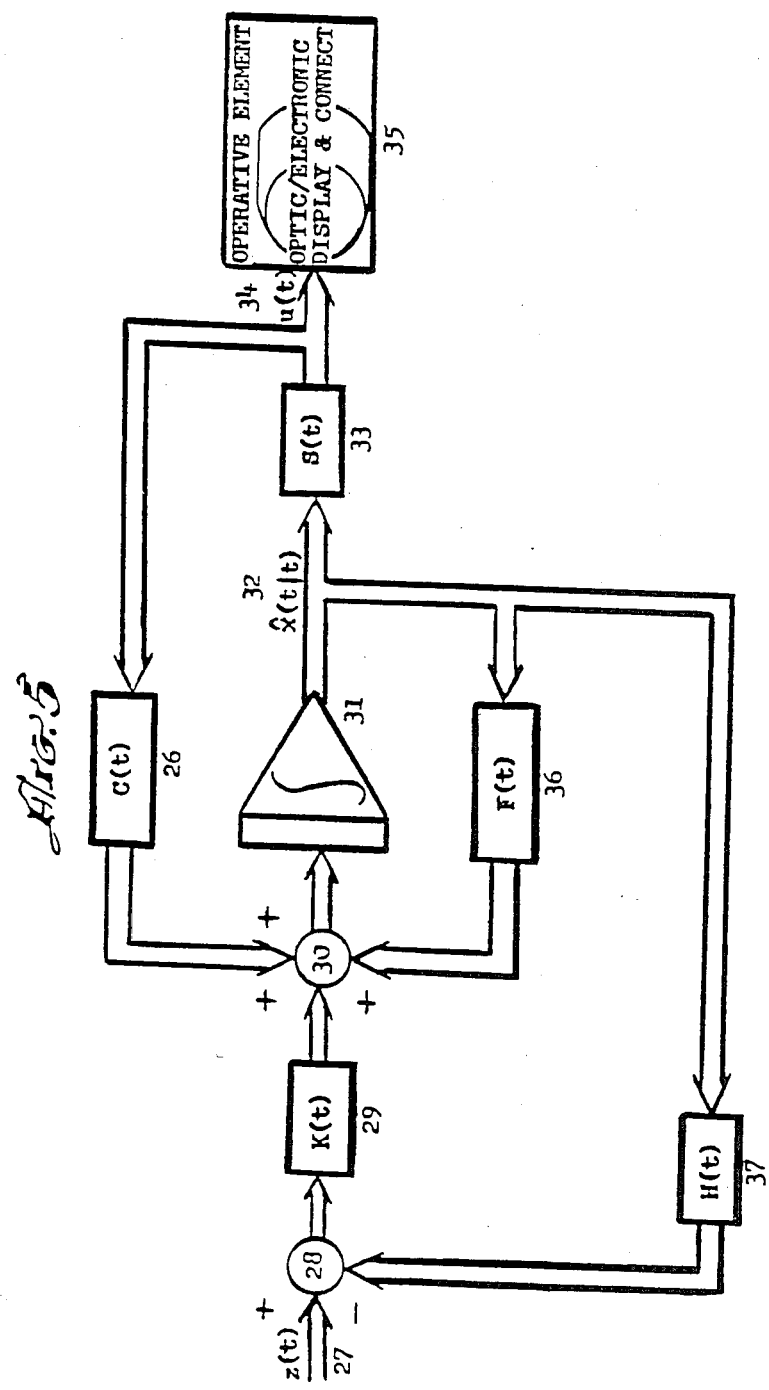
FIG. 5 is a greatly simplified block diagram and schematic representation of a single optimal control system.

FIG. 5 is a simplified illustrative block diagram schematicly depicting a single optimal control system. The modified optimal control system operates continuously on a given linear stochastic regulator problem first described mathematically by Potter, Wonham, Meditch and other authors employed in accordance with the invention set forth hereinbelow:

$$u(t) = S(t)\hat{x}(t|t)$$

$$S(t) = -B^{-1}(t)C'(t)W(t)$$

$$\dot{W} = -F'(t)W - WF(t) + WC(t)B^{-1}(t)C'(t)W - A(t)$$

$$\hat{x} = F(t)\hat{x} + K(t)[z(t) - H(t)\hat{x}] + C(t)u(t)$$

for $t \leq t \leq t$ where $W(t_1) = \Lambda$ and $\hat{x} = \hat{x}(t|t)$ is the optimal filtered estimate of the systems state.

The value of the performance measured for the optimal control is described by $V(t_1 - t_0) = t_r W(t_0) P(t_0) + \alpha(t_0)$ where $\alpha(t_0)$ is derived from a solution of the differential equation $$\alpha = -t_r G'(t)W(t)G(t)Q(t) - t_r[S'(t)B(t)S(t)P(t|t)]$$

for $t_0 \leq t \leq t_1$ where $\alpha(t_1) = 0$ and $P(t|t)$ is the filtering error covariance matrix.

Nonlinear variance undergoing Taylor Expansion and summation such that numeral 26, $C(t) = [Cij(t)]$ where $$Cij(t) = \left(\frac{\partial fi}{\partial uj}\right)_o$$

number 27, $Z(t) = H(t)X(t) + v(t)$ which operates on 28. Numeral 29 predicates continuous Time Estimation where $K(t) = P(t|t)'H(t)R^{-1}(t)$ operating on element 30 simultaneously with elements 26 and 36.

Element 31 provides in part the optimal filtered estimate $$\int_{t_0}^{t} A(t_1 \tau) z(\tau) d\tau$$

and the optimal estimate $$E[x(t_1) z'(\sigma)] - \int_{t_0}^{t} A(t,\tau) E[z(\tau) z'(\sigma)] d\tau = 0$$

for all $t \leq \sigma \leq t$.

Element 32 $\hat{x}(t|t_1) = F(t)x(t|t_1)$ which is the optimal filtered estimate for some $t_1 > t_0$.

Number 33 $S(t) = -B^{-1}(t)C'(t)W(t)$ which drives element 34 u(t) where $u(t) = S(t)\hat{x}(t|t)$.

Numeral 36 is defined by $F(t) = [fij(t)]$ where $$fij(t) = \left(\frac{\partial fi}{\partial xj}\right)_o$$

and F(t) is a positive forcing function on element 30.

H(t) a negative forcing function on element 28 is defined by $$H(t) = [hij(t)]$$

where $$hij(t) = \left(\frac{\partial h i}{\partial x j}\right)_o$$

Numeral 35 denotes an operative element of an optical electronic nature associated with a connector and display means.

Figure 6:
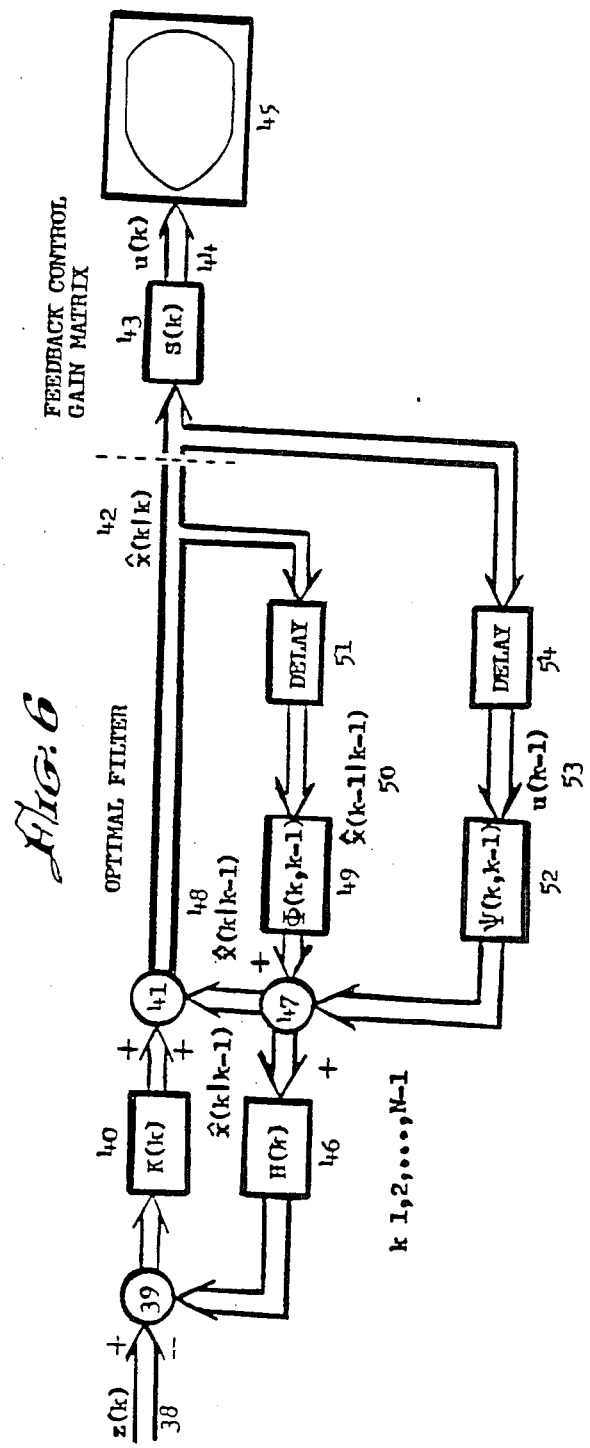
FIG. 6 is a fundamental block diagram and schematic representation of one of several equivalent optimal control systems for any given continuous stochastic linear problems.

FIG. 6 depicts a mathematical construct for discrete time control on an optimal control system. The equations and derivations are employed in accordance with the invention herein below;

x = n vector (state)

u = vector (control)
w = p vector (disturbance)
z = vector (measurement)
ν = vector (measurement error)
Φ = n×n state transition matrix
Γ = n×p disturbance transition matrix
Ψ = n×r control transition matrix
H = m×n measurement matrix Element 38 z(k) is a positive driving function on operator 39. Element 40, $K(K) = P[(K|K-1)P(K|K-1) + R(K)]^{-1}$ operates positively on element 41 which forces the optimal filter for the control system and is governed by relation 42 $\hat{x}(K|K)$.

$$\hat{x}(K|K) = \Phi(K,K-1)\hat{x}(K-1|K-1) + \Psi(K,K-1)u(K-1) + K(K)[z(K) - \Phi(K,K-1)\hat{x}(K-1) - \Psi(K,K-1)u(K-1)]$$

Number 43 denotes a general expression for the feedback gain S(K) which is equivalent to $-1/2\beta + N - K$.

Element 44 denotes u(K) where $u(K) = S(K)\hat{x}\,K|K)$ concerning time indexing for a given deterministic problem wherein $K = N - ju(K) = S(K)\hat{x}(K|K)\hat{x}(K|K-1) = \Phi(K,K-1|K-1) + \Psi(K,K-1)u(K-1)$ which is a consequence of the optimal estimate of X(K).

Element 44 drives numeral 45 which is a given operative element. Two time interrupts are disclosed by numbers 51 and 54 respectively. The optimal estimate of X(K) reflects the fact that the control signal $S(K-1)\hat{x}(K-1|K-1)$ depicted in part by element 50 and as a consequence $\hat{x}(K|K) = \hat{x}(K|K-1) + K(K)[z(K) - H(K)\hat{x}(K|K-1)]$ where as described by element 48 and the like $$\hat{x}(K|K-1) = \Phi(K,K-1)x(K-1|K-1) + \Psi(K,K-1)u(K-1)$$

for the optimal estimate.
Element 49 (K,K−1) where $$\Phi K, K-1 = \frac{\hat{x}(K|K-1) - \Psi(K,K-1)u(K-1)}{\hat{x}(K-1|K-1)}$$

As a further consequence of the above hereto mentioned control segment $$\Psi(K,K-1) = \frac{\hat{x}(K|K-1) - \Phi(K,K-1)\hat{x}(K-1|K-1)}{u(K-1)}$$

where
$u(K-1) = \Psi^{-1}(K,K-1)\Phi(K,K-1)\hat{x}(K-1|K-1)$
which reduces to $\hat{x}(K|K) = K(K)z(K)$ Elements 49 and 52 positively forces element 47, which in turn forces element 41 and 46 respectively. Numeral 46, 1+(K) acts as a forcing function for 39.

Figure 7:
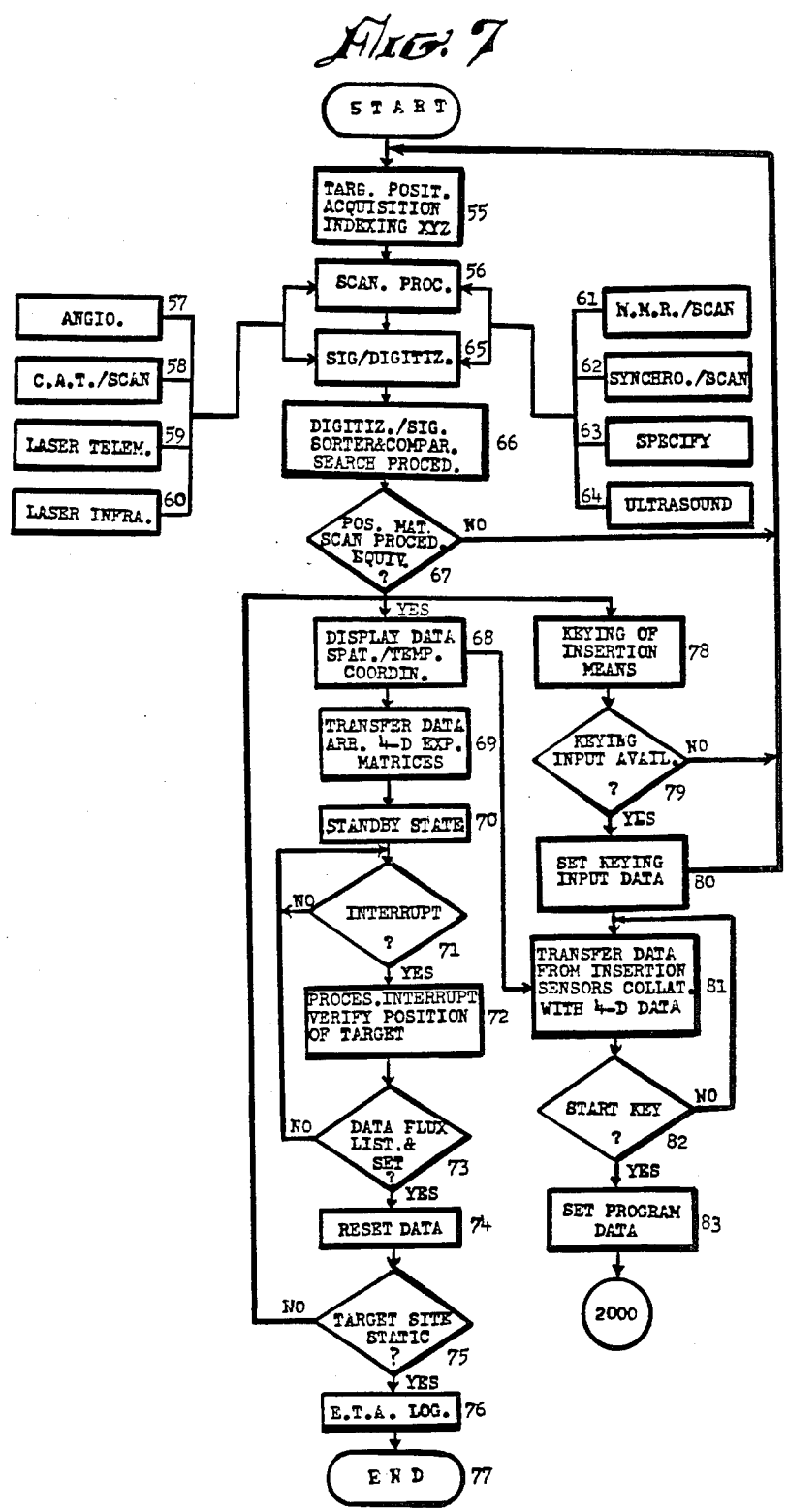
FIG. 7 represents a flow diagram for the targeting and position acquisition means.
Figure 8:
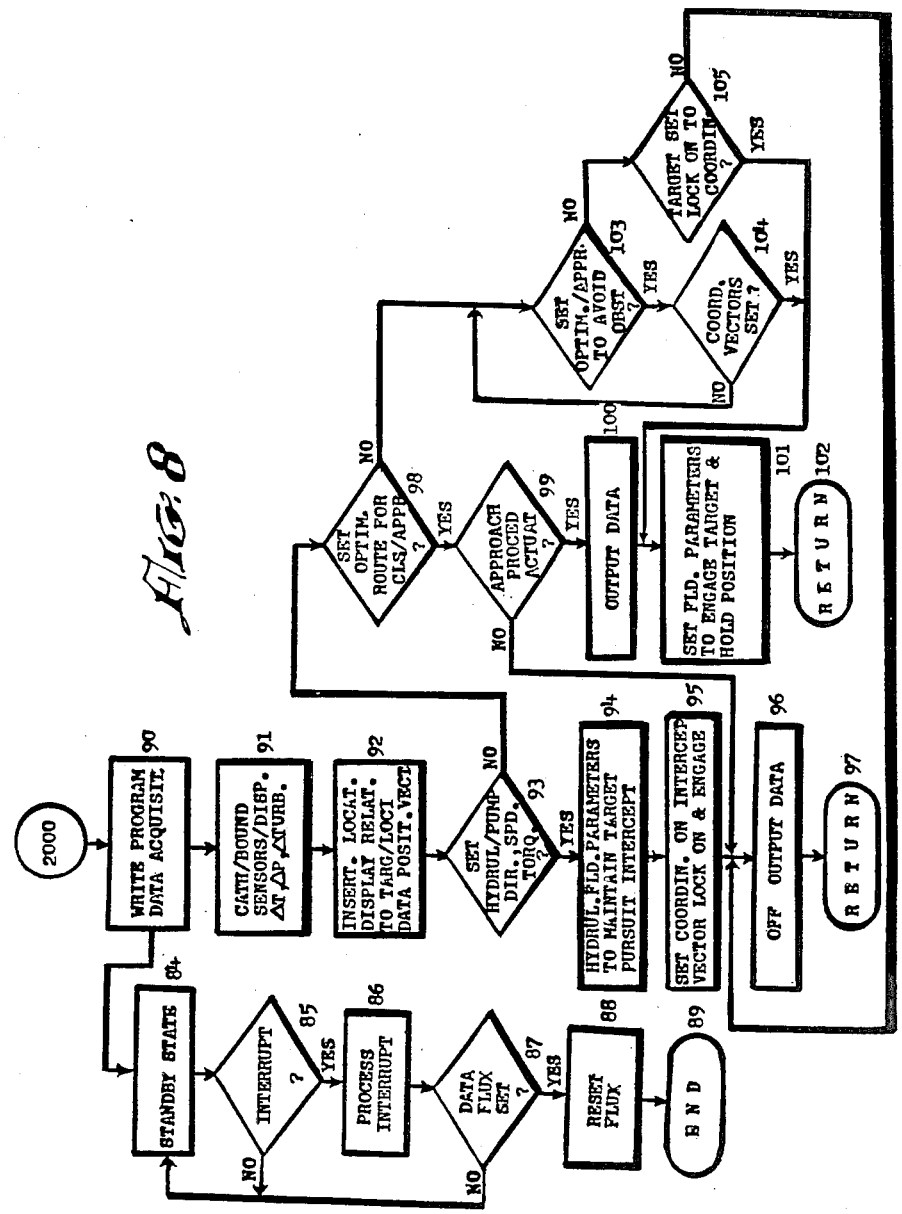
FIG. 8 is a continuation of FIG. 7.

FIGS. 7 and 8 represents a descriptive flow diagram for position acquisition and independent targeting of given sites by various analytical scanning means. A three dimensional axial topography is exacted by a sterotaxic means denoted by numeral 55. Numerals 57 through 64 denotes the various scanning means utilized explicitly for data acquisitions and collectively feed into an optical electronic encoding scanning process 56, which is associated with a signal digitizer number 65. More specifically number 57 denotes angiography, 58 represents CAT/SCAN, 59 defines Laser Telementry which is associated with number 60, which is a Laser Interferometry (INFRA) technique. Numeral 61 denotes a Nuclear Magnetic Resonance technique, whereas 62 depicts a scanning technique employing Synchrontron Radiation. Number 64 discloses an ultrasonic technique for targeting and number 63 is a unspecified ancillary means of exacting a target location. A signal digitizer means is indicated by numeral 65, wherein analog signals are converted into their digital equivalents. All signals are sent to number 66 an online compiler and database which takes the digitized data from two or more different scanning systems attempting to compare and sort data on the basis of comparison for position conformation. Number 67 denotes a data base which repeats the scanning process if no positive matches are found which are equivalent, and then it conveys data for display revealing the spatial temporal coordinates of the target loci in real time at number 68. Data transferred from number 68 is divergently sent to numerals 69 and 81 respectively. The digitized pairs of data signals are converted into their four dimensional binary equivalents, whereby the program is placed in a standby state denoted by number 70, followed by an interrupt at numeral 71. A further search is provided by a subroutine which first verifies the position of a given target denoted by number 72 and then scans repeatively listing data values which are set at number 73, and reset at 74 or returned for further verification. If values change with respect to the position of a given target loci the behavior is noted by element 75 and new positions or patterns are plotted, if not the target loci is considered static and an appropriate E.T.A. of the target loci and a fiber optic member of the Coupler device is computed and duely logged by element 76, wherein the program is terminated at number 77. If the position of the target site is variable due to its being in motion an auto keying sequence is enlisted as is described by number 78 and if determined available 79 is set or augmented as prescribed by numeral 80, or set back to element 55 for further acquisition of the target site. The data from the Couplers insertion sensors is then collated with the spatial temporal position of the target from number 68 by numbered element 81. Number 82 denotes a keying sequence is in progress in order to actuate a subprogram controlling the motion of the insertion means or catheter portion of the Coupler device as described by element 83. Then, as in the case of the step involving data transmission from the position acquisition program described herein by FIG. 7 to the actuation of the insertion catheter program as described in the foregoing FIG. 8 with the continuation or transfer being noted by numeral 2000.

FIG. 8 depicts the necessary logistical commands required to launch the catheter bound emissive fiber optic portion of the Coupler device. Number 90 is an access element allowing either the user or the computer to program a special hydraulic insertion means to engage a given target site. The output derived from element 90 is transferred either to element 84 or 91. If the coordinates of the insertion means and the target site are nearly equivalent, then the target site resides in close proximity to the insertion means wherein the operational mode is put in a standby state, which is denoted by number 84. The data is conveyed from sensor onboard the catheter means and matched with those positional vectors of the target site conducted, when the interrupt 85 and process interrupt numeral 86 are in progress. The data parameters are continuously sampled and are therefore in a state of dynamic flux, and they require that the data flux be set as described by element 87 and be cleared or reset as defined by element 88 prior to the termination of the program, which is denoted by number 89. If the emissive catheter is not in close proximity to the target, as is often the case, the divergent programming then enlists the aid of an onboard sensor array to scan for differences in displacement, temperature, pressure, and turbulence noted by number 91. The data concerning target position relative to the insertion means is indicated by number 92. Based on information instructions auto keying parameters of the hydraulic insertion means is actuated, controlling the delivery of the emissive catheter, as prescribed by number 93. Upon setting the hydraulic parameters, necessary to engage the target site, the hydraulic fluid parameters are sustained to maintain target pursuit and a probable intercept, as indicated by number 94. All coordinates of the insertion means are set to lock the emissive optics catheter on an intercept vector which engages the target site 95, where the data is combined with off output data 96 such as infusion parameters, and number 97 indicates a return to the mainline sequence for further instructions via a high density interlock memory network. If for some reason the hydraulic parameters controlling the direction, speed, and torque of the insertion means cannot be exacted by element 93, then an alternate mode of operation is specified by numeral 98. Element 98 is a subroutine calling for a program strategy specifically to inact the optimum route and the nearest approach necessary to engage a given target, which is hereto unaccessible with such conditions as the target site being located at the end of circuitous corridor or channel. If an affirmative course of action is prescribed then the necessary approach vectors are assigned by element 99 and it is assigned feedback data from onboard sensors denoted by the numeral 100. The combined totality of data derived from the preceding numerals such that the fluid parameters necessary to power the hydraulic means to engage the target and hold position against any and all circumstances alluding to turbulence, reverse flow vectors, and the like as described by number 101. The information and present status of the catheter means are sent to a separate high density data base number 102 for future assessment. A negative response assigned to number 98, then forwards the information flow to element 103, which effects a subroutine on a program, which provides the necessary strategy needed in order to avoid obstructions, between the emissive catheter and the target site. Once the correct pursuit vectors are assigned by element 103 it then becomes necessary to verify the coordinates as prescribed by element 104, before the appropriate parameters are set by element 101, if not the mode of operation is recycled to number 103 for verification, and if a target cannot be engaged without effecting an obstacle, then number 105 must be enlisted.

Figure 9:
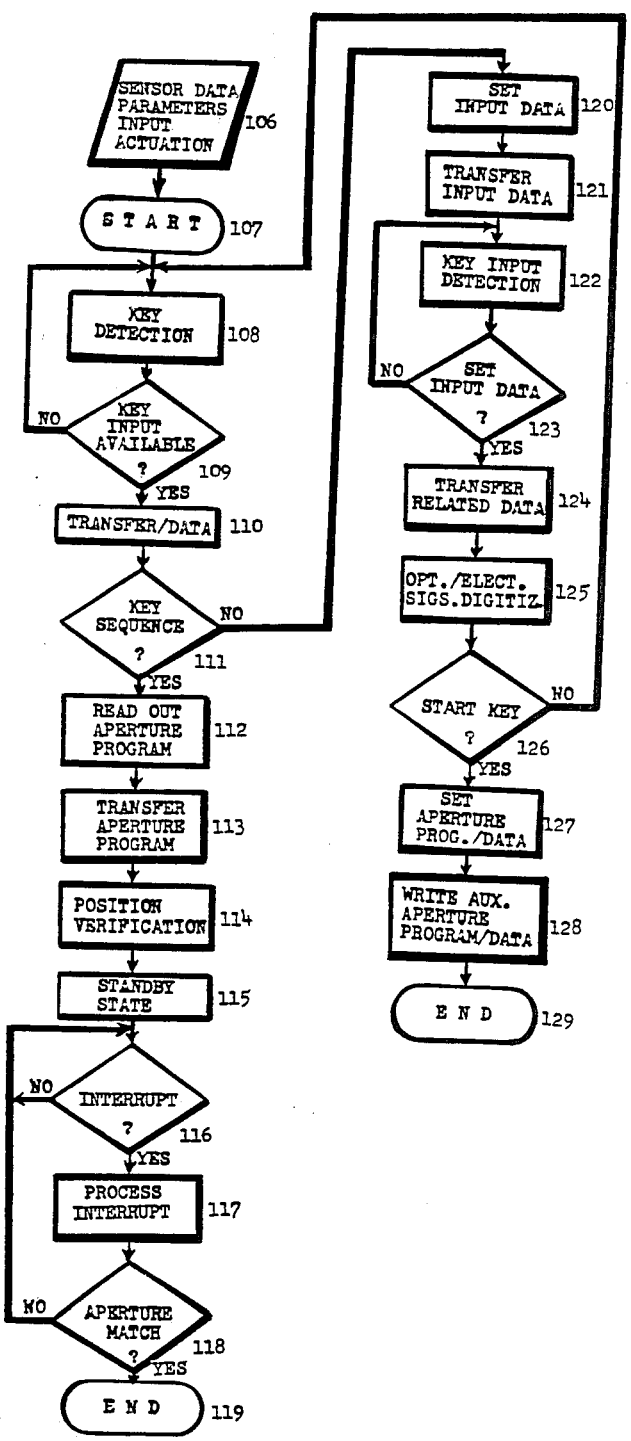
FIG. 9 is essentially a representative flow diagram for the operation of one of the two equivalent electronic diaphragms.

FIG. 9 basically is a representative flow diagram depicting the operative programming for one of two equivalent electronic diaphrams. The start sequence 107 is actuated by impulses derived by feedback sensors 106, and once actuated an auto keying sequence is made available by numeral 108. The conformation of a specific keying sequence is denoted by number 109. The data is then transferred by element number 110, and ready for the actual key sequence denoted by number 111. If the sequence keying takes place then the readout aperture program is initiated by element 112 and if a key sequence is unmatched or unattainable, then the input data must be directly set either manually or otherwise, as described by element 120. The aperture program once initiated is transferred by number 113, and the position verification is enlisted by number 114. During position verification number 114, the subsystem, is then put into a standby state numbered 115, an interrupt occurs, numbers 116 and 117, until the position or size of the diaphragms aperture matches those called for by the specific program element 112. If a positive match can be initiated by 118 then the program is terminated, number 119, and is now ready for new input or is sent back to the interrupt process as is in step 116 until a match can be qualified. Element 120 in effect concerns the programming of complexed and ultrafast operations unlike the previous portion of the program. The complex set of instructions are transferred by number 121 where the key input detection occurs at element 122. Once the data is set by element 123, then additional data related to systems operation, such as duel simultaneous operation of a sister diaphragm or the like is directed by element 124. Optical electronic signals are digitized by operational element 125 and the start keying sequence is initiated by element 126. The complexed sequence of data operations range from sequential dilation to opposing shifts in the rotational oscillations between two or more electronic diaphragm means, as is prescribed by numeral 127. Auxiliary operations on apertures can be either manually keyed or auto keyed to supplement the ongoing program as denoted by element 128, at which point if all requirements are met the process is terminated by element 129, and the entire system is made ready for a restart of the entire process.

Figure 10:
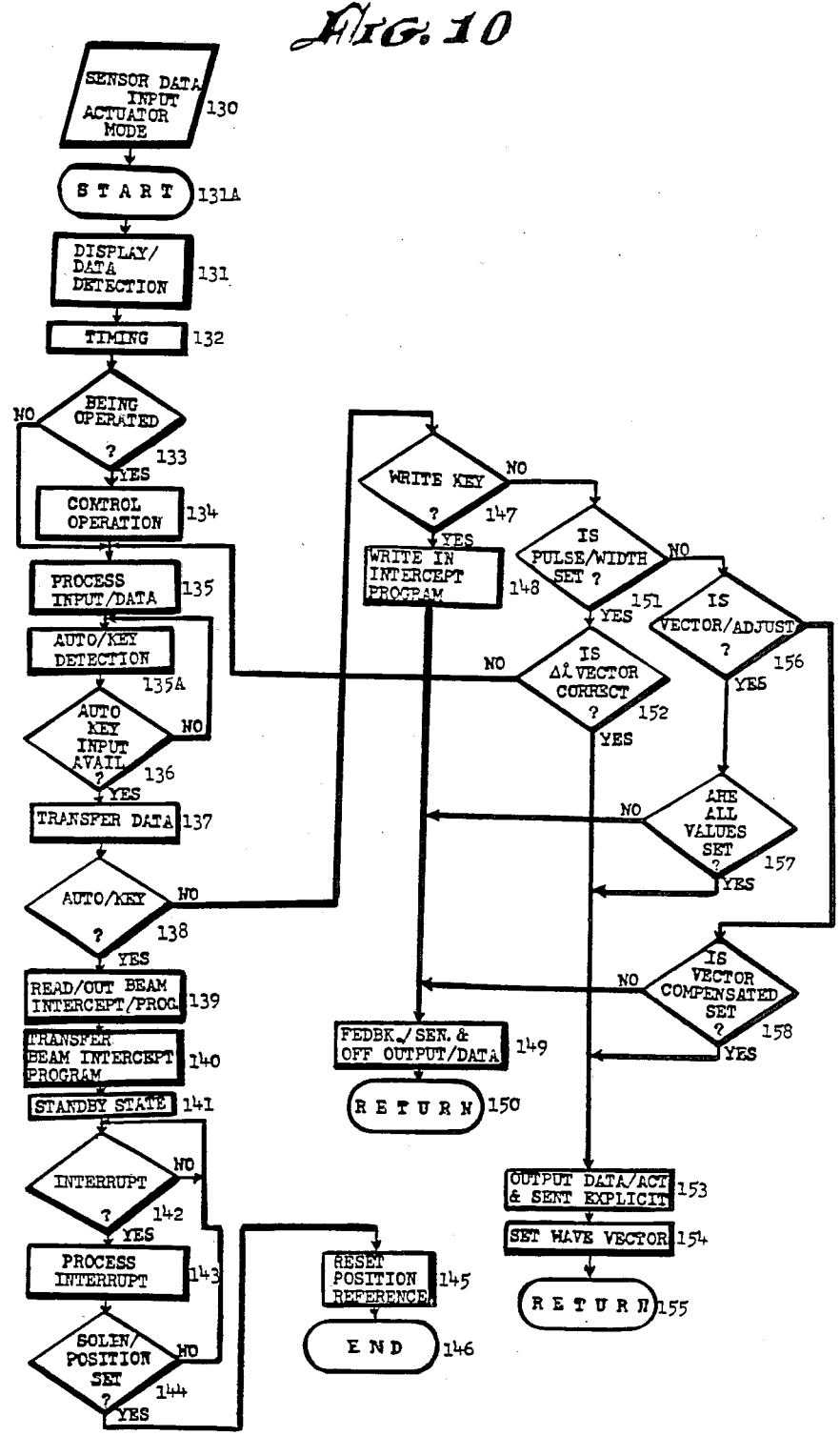
FIG. 10 is a greatly simplified flow diagram for the automated electronic shutter audio acoustic complex.

FIG. 10 is a greatly simplified flow diagram which is indicative of a program providing for the joint operation of an electronic shutter automated chopper complex. Data obtained from sensors actuate the starter mode numbers 130, and 130A respectively. The values are initially displayed as the data undergoes detection number 131, which is completed prior to entering the timing sequence noted by number 132 and is then collectively operated on by element number 133 and controlled by element 134. Process input data number 135 is conveyed to the auto key detection numeral 135A. If the instructions are available then auto keying may be conducted by number 136, wherein the data is transferred by number 137 and auto key verification is enlisted by element 138. The beam intercept is provided by number 139 as it is read into both the chopper and the shutter complex if available or the data is shunted to element 147. Numeral 140 provides for the transfer beam intercept program wherein the data is transferred simultaneously to the two chopper elements and the electronic shutter means. The operational mode is placed in a standby state, number 141 prior to the interrupt process and is denoted by numbers 142 and 143. The internal operation of the shutter means is governed by solenoid operations and each member of a solenoid pair must be monitored, set, and reset during the operations mode as prescribed by numerals 144 and 145, until the operation is completed as indicated by element 146. Number 147 is a subprogram of the main sequence providing auto keying or manual keying and it governs the operation of the chopper complex. Element 148 allows the operator to write in the intercept program. The information is conveyed from 148 and numeral 149 when additional output data and feedback sensory input is collated with numeral 148 output, prior to being returned to the high density memory bank of the main computer which is number 150. If the necessary pulse width of the emissive source is not contained within the present program, width can be set by the EEPROM element to exact the correct wave characteristics as noted by number 151, which is verified by output sensors as disclosed by number 152, or is conveyed to establish whether or not the characteristic vector components need to be adjusted by operations of numeral 156. The output data ia acted upon and sent explicity to the respective operational chopper number 153, which utilizes the output data to set the proper wave vector components, numeral 154, wherein all data can further interact with assimulated data contained in the main computer network via its return number 155, to the main terminal. Numerals 156, 157, and 158 are essentially auxiliary vector verification elements, and will eventually return to the main computer for enhancement or additional instructions.

Figure 11:
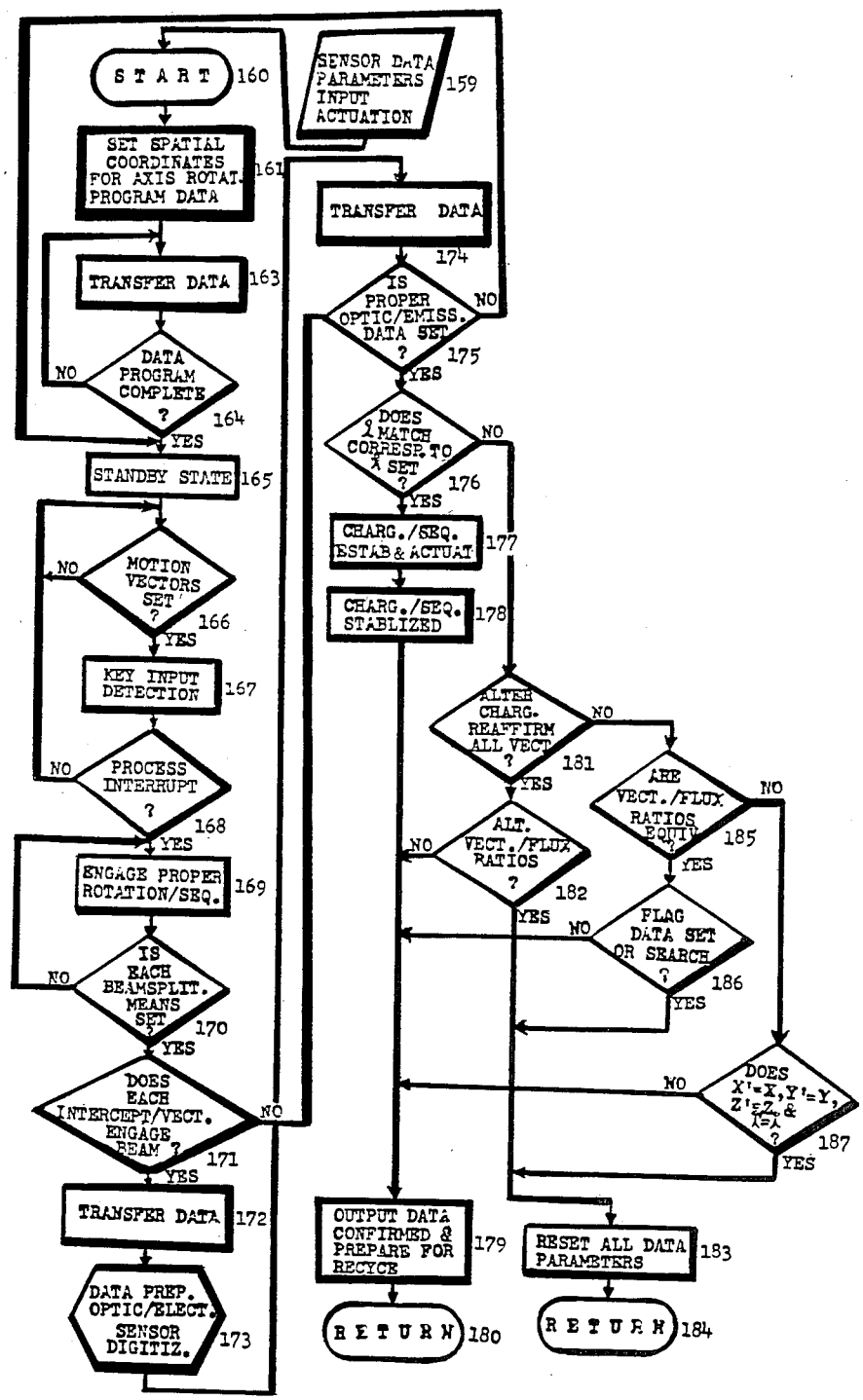
FIG. 11 is a representative flow diagram depicting a program for the operation of one of four equivalent automated beam splitting devices.

FIG. 11 is a representative diagram which depicts a program for the operation of one of four equivalent automated beam splitting devices. The system is activated by numeral 160 which receives sensory data, which is made available by number 159. The spatial coordinates for the axial rotation program necessary to intercept a given emissive transmission are depicted by numbers 161, 162 which both provides for a three hundred and sixty degree rotation in the horizontal plane and a one hundred and eighty degree rotation in the vertical plane of each beam splitting unit. The data is transferred to a microprocessor incorporated into the given beam splitter means as denoted by number 163. The transferred data undergoes verification as determined by its completeness as described by element 164, whereby the entire unit is put on a condition of standby denoted by number 165, wherein conditions for motion are set by element 166. The auto key input detection occurs as denoted by number 167 prior to the process interrupt number 168, whereby the proper rotation sequence is engaged as noted by number 169. Since there are four beam splitting means and more then one of them may act simultaneously or inconjunction with each other, such that all units must exchange positional data, as described by element 170. Onboard feedback sensors incorporated into each beam splitter verify if each intercept vector is properly set to engage a given emissive beam, denoted by numeral 171, prior to data transferral, numeral 172, if not the proper optic emission and verification must be conveyed to auxiliary element 175. The data preparation from optical electronic sensors is digitized and denoted by number 173. It is then transferred to the mainline computer for further instructions, as noted by element 174. Verification of the proper emission denoted by number 175 is established and conveyed to number 176 for additional verification corresponding to the wavelength. While the wavelength is being determined a charging sequence for the capacitor governing the dielectric properties of the mirror is established and actuated, as noted by number 177 and stabilized by numeral 178. Once the dielectric properties of the mirror component comprising the beam splitter unit are confirmed, and prepared to be recycled as described by numeral 179, to be reconveyed to the central computer to be acted upon further, as disclosed by numeral 180. In the wavelength set by the mirror does not match the wavelength which is specified by the program as prescribed by number 176, then the process is shunted to numeral 181, where the dielectric properties of the mirror are altered accordingly and verified before proceding to numeral 182, wherein altered vector flux ratios are examined. If not, a search is made to see if the vector flux ratios are equivalent for both the command impulse and the charge setting, as disclosed by number 185. The data from 182 is if confirmed sent to a systems compiler, whereby all data parameters are cleared or reset as disclosed by element 183, this is done prior to returning to another facet of the mainline computer terminal denoted by element 184. The data derived by element 185 is conveyed to number 186, which flags the data supplement set or searches other parameters. If a negative response is elicited by element 185 then the data is further shunted to number 187, wherein a search and verification of wavelength structures or electronic characteristics is initiated. Numbers 181 through 187 irregardless of their input have thier output collectively sent for future analysis and processing to the main computer.

Figure 12:
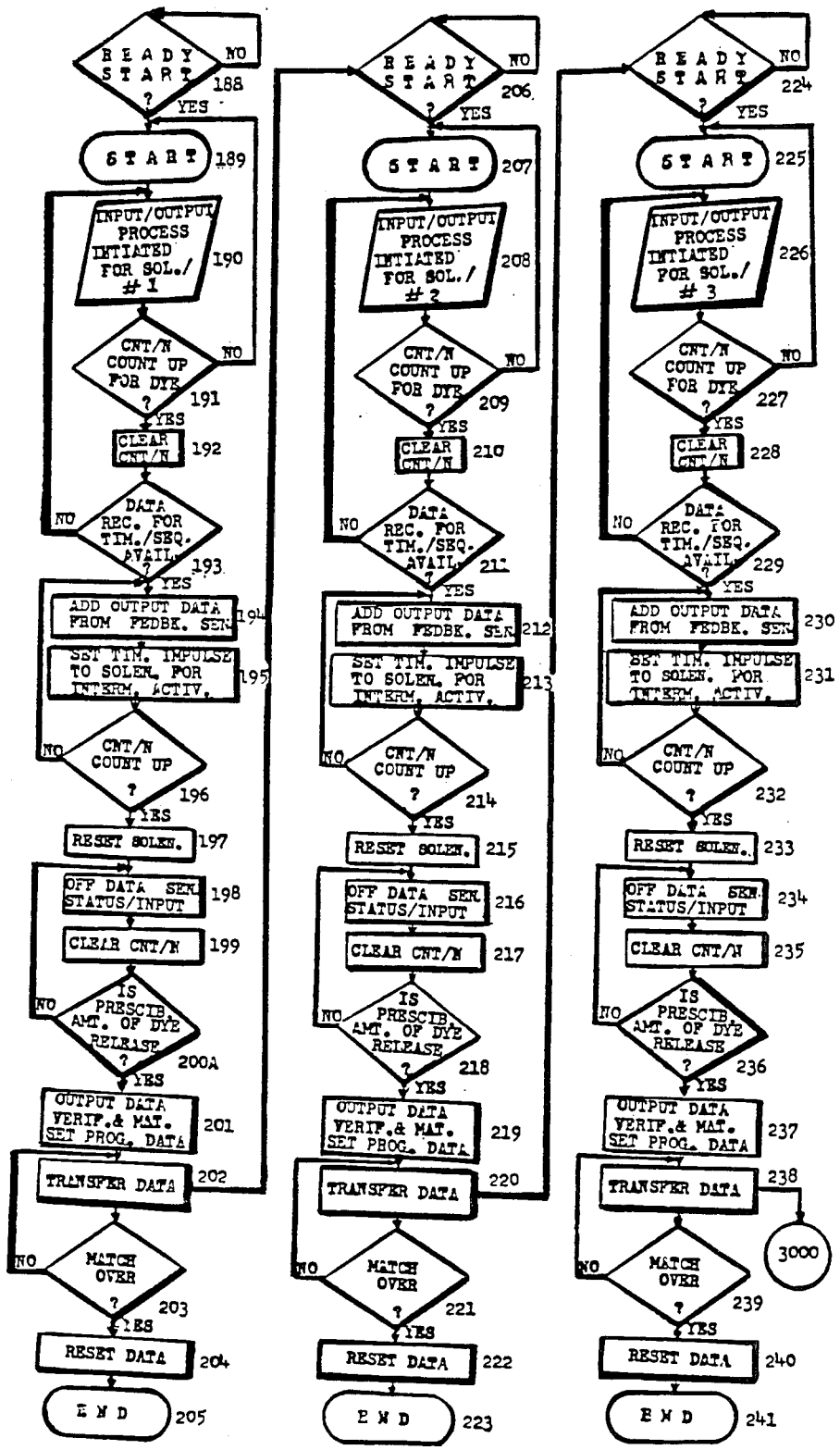
FIGS. 12 and 13 are flow diagrams which pertains to the explicit programmed operation of inlet solenoids governing the flow of dyes into a dye pump.
Figure 13:
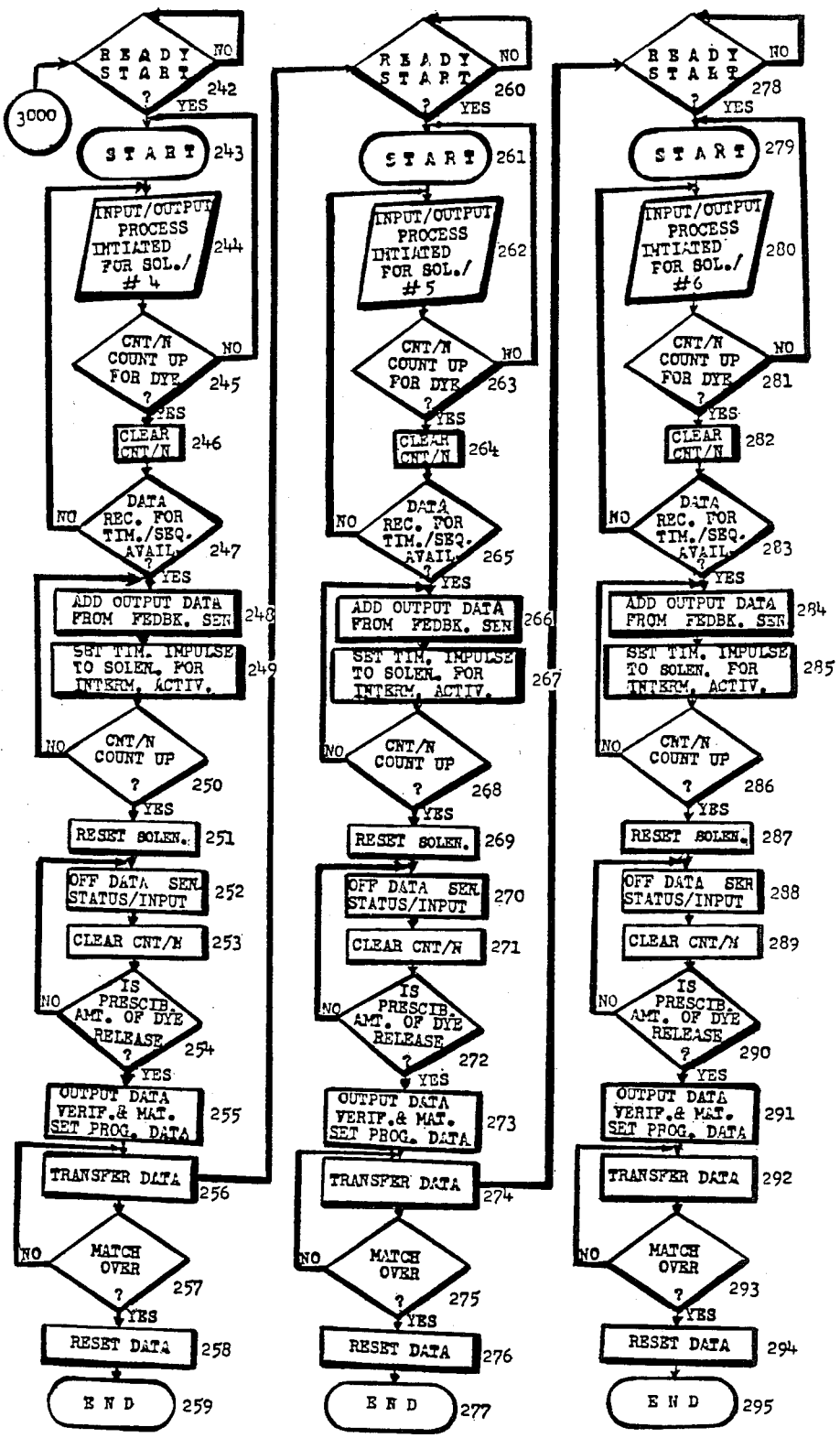

FIGS. 12 and 13 are flow diagrams depicting a program which specifies solenoid operation governing the inlet or flow of pressurized dyes from either reservoirs or dye channels. Impulses directed initially by the on-line computer or keyed manually by the user as is prescribed by number 188, which elicits the start sequence 189. Numeral 190 a input/output sensory feedback process intiates movement for solenoid #1. The rate of firing for a given solenoid is entered by number 191, which counts up to a value for a given dye release, and once the value is established it is cleared, as denoted by numeral 192, so that data can be recited for the timing sequence if available, denoted by number 193. It is then collated with additional output data from feedback sensors, as noted by number 194. The timing sequence needed for controlled release of a given dye is sent as a series of digital electronic impulses to initiate intermediate activity, or the operation of the solenoid as noted by numeral 195. A secondary count up sequence for repeated solenoid firing is initiated by numeral 196, if more of a given dye is needed for a given wavelength characteristic. The seleniod is reset for further operation by number 197. Off line data concerning dye status, chemistry, pressure, and temperature effect solenoid operation, as depicted by number 198. The solenoid system is cleared of count N as noted by element 199, whereby data verification of the quantity of dye released is properly assessed by element 200. The output data is verified and matched as further program data is compiled by number 201. The data is then transferred by numeral 202 to elements 203 and 206, while the verification of the programs equivalency is assessed against the actual operation of dye release as noted by numeral 203. All data values are reset as denoted by number 204, when a positive match has been effected. If all events of solenoid operation are satisfactory then the solenoid operation is terminated for the solenoid in operation, and are made ready for the next phase of the operation, as noted by numeral 205. The operation of the remaining five solenoids are equivalent to the solenoid operation described herein the above. Each solenoid supplies the next with additional data to bring it to a ready state. Solenoid one through three control the release of separate dyes from thier respective reservoirs, whereas solenoid four controls a nitrogen purging system and the remaining solenoids govern entery or exit of the dye complex into the mixing chamber and the dye cell proper. Number 206 through 223 depict a repetitive sequence of events which are equivalent in nature to those exemplified by numbers 188 through 205. Numerals 224 through 241 are equivalent to 206 through 223 preceding it, and data is transferred by element 238 of FIG. 12 to element 242 of FIG. 13 as indicated by numeral 3000. Number 242 through 259 are equivalent to numbers 224 through 241 preceding it. Operative modes governing solenoid five and six are like the preceding solenoids and are equivalent to numerals 260 through 277, which are exactly the same as elements 278 through 295. The only differences between one solenoid operation to the next are the impulses or command instructions specifying the release of given dyes, which call for different quantities of each respective dye to be released at any given time.

Figure 14:
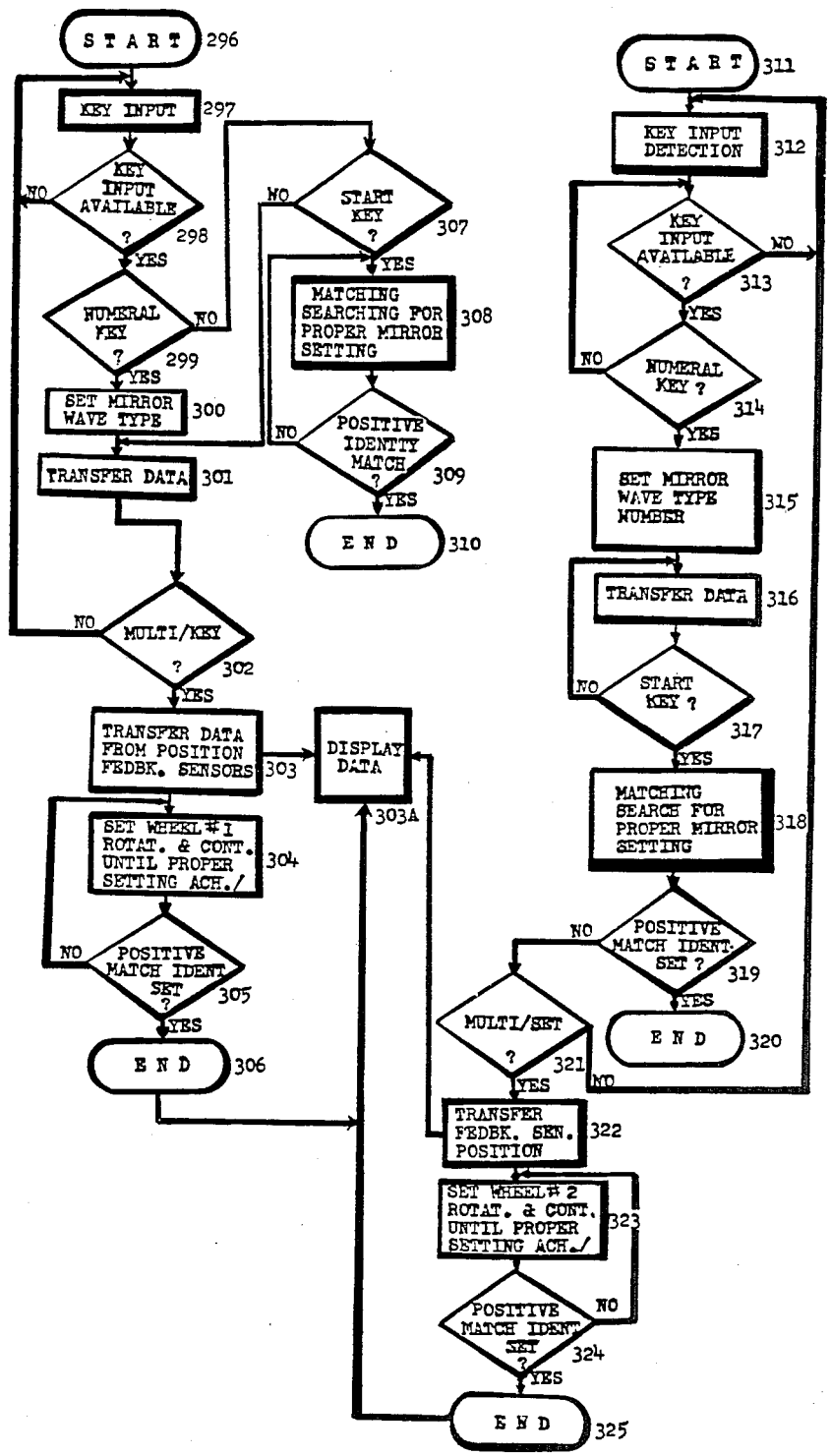
FIG. 14 is a flow diagram representing the necessary programming for positioning specified mirrors of the dye cell pump to engage the emissive source.

FIG. 14 is a flow diagram specifying the programming necessary for positioning a single pair of partially reflective emissive mirrors, which intercept an emissive source prior to entering the dye cell chamber, and upon exiting the said chamber. There are two rotating wheels, each containing its own equivalent mirror complement and rotating independently of the other, requiring separate but equivalent programs. Start sequence numeral 296 is activated by the operation of solenoid elements as is start sequence 311. The input is then keyed either manually or automatically to a given setting, as noted by numerals 297,298, and it undergoes verification by element 299 of the keying process. Upon verification the data signal is sent to numeral 300, wherein the mirror wave type is explicity set, if not the data signals are shunted to element 307 for another attempt to initiate the key starting sequences. The data is transferred from element 300 by number 301 to element 302, which determines if multiple keying of a sequence is available. Numeral 303 initially transfers data from position sensors which are conveyed to 303A for display, and the electronic motorized unit governing the rotation of the first of two wheels, until a proper mirror setting is achieved as determined by numeral 304. If a positive or exact match between the position which is specified by element 304 and the actual position of a single specified mirror element, then the process of wheel rotation, search and alike is terminated, as denoted by number 306 and displayed by 303A. The data from 305 is recycled to 304, until an exact match is found. The data obtained from 307 is conveyed to number 308, a separate microprocessor, which actually searches for and then matches the proper wave characteristic of a specified mirror element, with a said beam source. The data output from 308 is sent to element 309, which verifies whether or not an identical match has occurred and the program is terminated as shown in number 310, or is recycled back to number 308 for data confirmation. The second start sequence depicted by number 311 governs the motion of the second rotating wheel containing an equivalent circular array of mirrors. Key input detection is described by numeral 312, which conveys data into element 313. Element 313 determines whether or not keying input is available and conveys its information to element 314, which determines if a numeral keying sequence is in progress. Both elements 313 and 314 return to the preceding element if a negative condition occurs. The given mirror specified for the emissive beam as it exits from the dye cell is determined by the wave type number previously determined, as prescribed by numeral 315. The data from numeral 315 is pooled and transferred to number 316. The data which has been transferred by 316 is acted upon by element 317, which gives either a positive affirmation of the keying sequence or reconveys its output to be recycled with data continuously transferred by numeral 316. Number 318 is a separate subroutine which independently searches for the proper mirror setting. Element 319 verifies if a positive match is infact identified and set, whereby the program is terminated for the second wheel element, as noted by number 320. If a positive match can not be identified, then element 319 will convey its output to element 321. If multiple settings are specified by element 321, then data is conveyed to number 322 and if a negative response is elicited the data output is recycled to the start sequence. Data transferred from feedback sensors concerning the position is simultaneously sent to 303A to be displayed, and to numeral 323, which governs the position of wheel #2. Number 323 provides electronic impulses which set the wheel into motion, until the proper setting can be achieved. The data derived by number 323 is sent to element 324 for further verification of data, if a positive match occurs and the correct mirror setting is established, then the program concerning the second wheel is terminated, as noted by numeral 325 and it is sent to element 303A for display.

Figure 15:
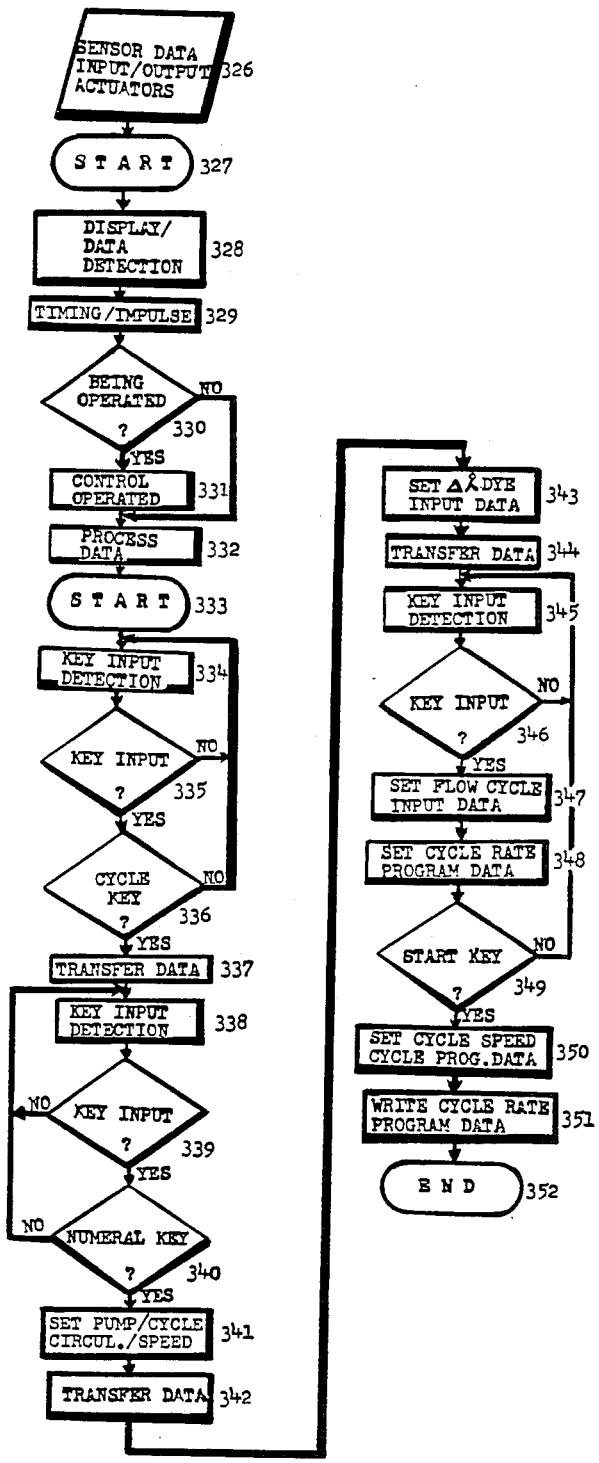
FIG. 15 depicts the flow diagram for a program which controls the direction, speed and torque values of the dye pump.

FIG. 15 represents a flow diagram depicting a program which controls the direction, speed and torque values of the dye pump means, in the dye cell complex. The sensory input and output data denoted by numeral 326 actuates the start cycle, as denoted by number 327, for the electronic centrifugal pump means of the dye cell unit. The operation of the pump means regarding all functions are continuously detected and displayed, as noted by numeral 328. Parameters controlling timing of electronic impulses for either the continuous or intermediate operations is described by number 329. Element 330 indicates whether input is being acted upon and conveys its input to numeral 331, for the sequencing of controlled operations. Number 332 consists of a series of command instructions, which process the incoming data and then activating the secondary start cycle, as denoted by numeral 333. Keying input detection is depicted by number 334, which directs its input to element 335, wherein the key input is verified or recycled back to number 334 for reprocessing. Element 336 denotes a specific cycling sequence inactment for the dye pump. The data is conveyed from element 336 to numeral 337 which transfers the data to a key input detection means, which is denoted by numeral 338. Key input is verified by element 339, and the numeral keying sequence is verified by element 340, both elements return to key input detection if verification is for some reason not possible. From the preceding elements the direction of the pumps flow and its speed are determined as set by numeral 341, which then transfers its data via numeral 342 to element number 343. Number 343 then sets the wavelength difference by specifying the dye type and its quantity. The data is transferred from number 343 by number 344 to the key input detection unit, which is denoted by number 345. The input availability from number 345 is verified by element 346, which sends the data if available to number 347. Numeral 347 sets the flow cycle based on incoming data and conveys the data to number 348, wherein a cycle rate program is elicited. The program data from 348 is then relayed to element 349, which establishes if an additional key starting sequence is available. If a keying sequence is available element 349 conveys its input to numeral 350, and if no keying sequence is available then the data is returned to numeral 345 for further processing. Number 350 once again sets the cycle speed, its direction and torque values via the cycle program data. An additional cycle rate program can be automatically written if the conditions warrent it, as noted by number 351, at the end of the sequence prior to the pump cycle ending, as denoted by numeral 352. The repeatative keying procedure is necessary in the program's execution, if events specifying wavelength characteristics are undergoing rapid fluctuations.

Figure 16:
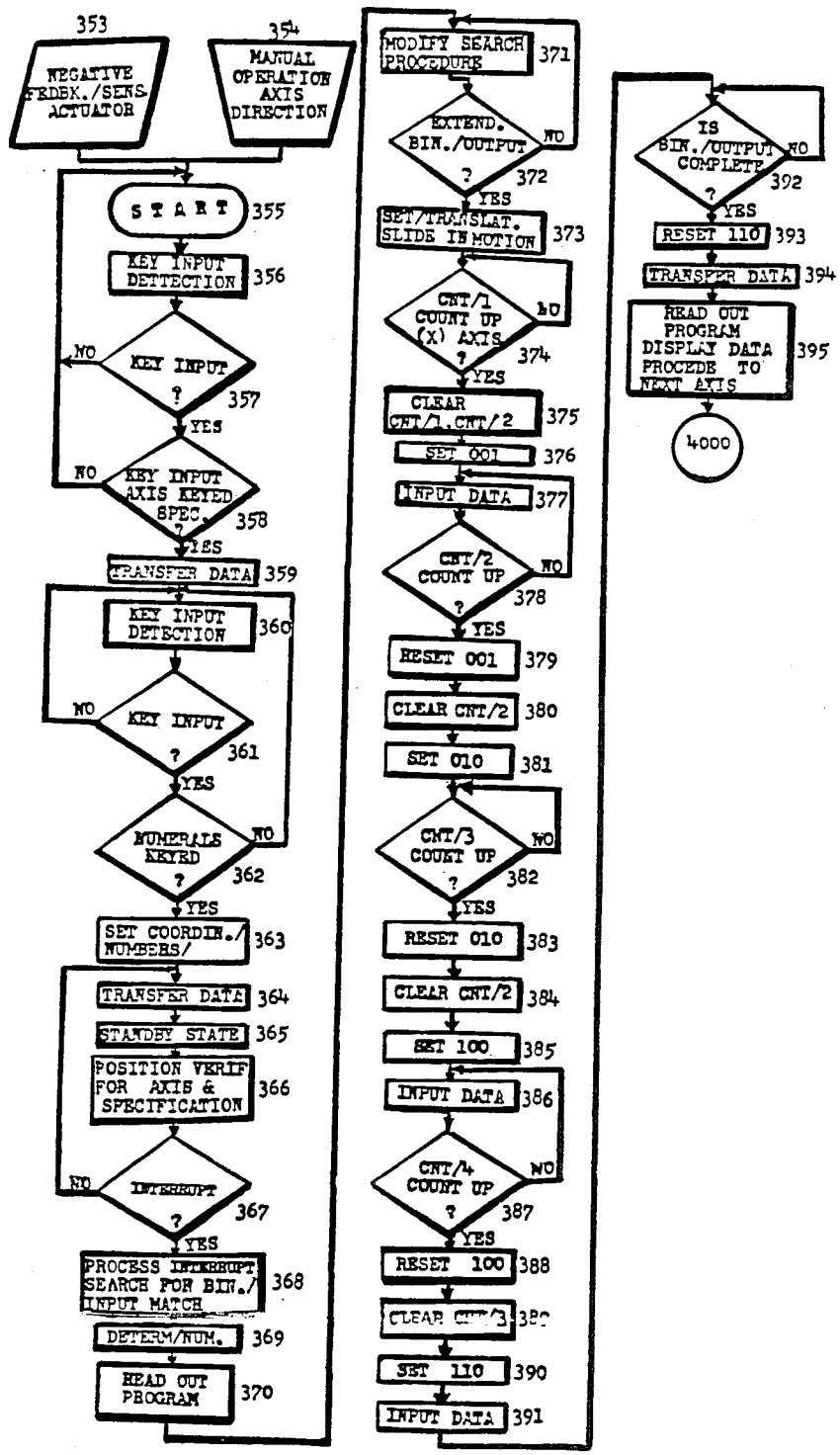
FIGS. 16 through 18 are representative of flow diagrams which specify a program sequence calling for three dimensional motion for an X, Y, Z translational stage.
Figure 17:
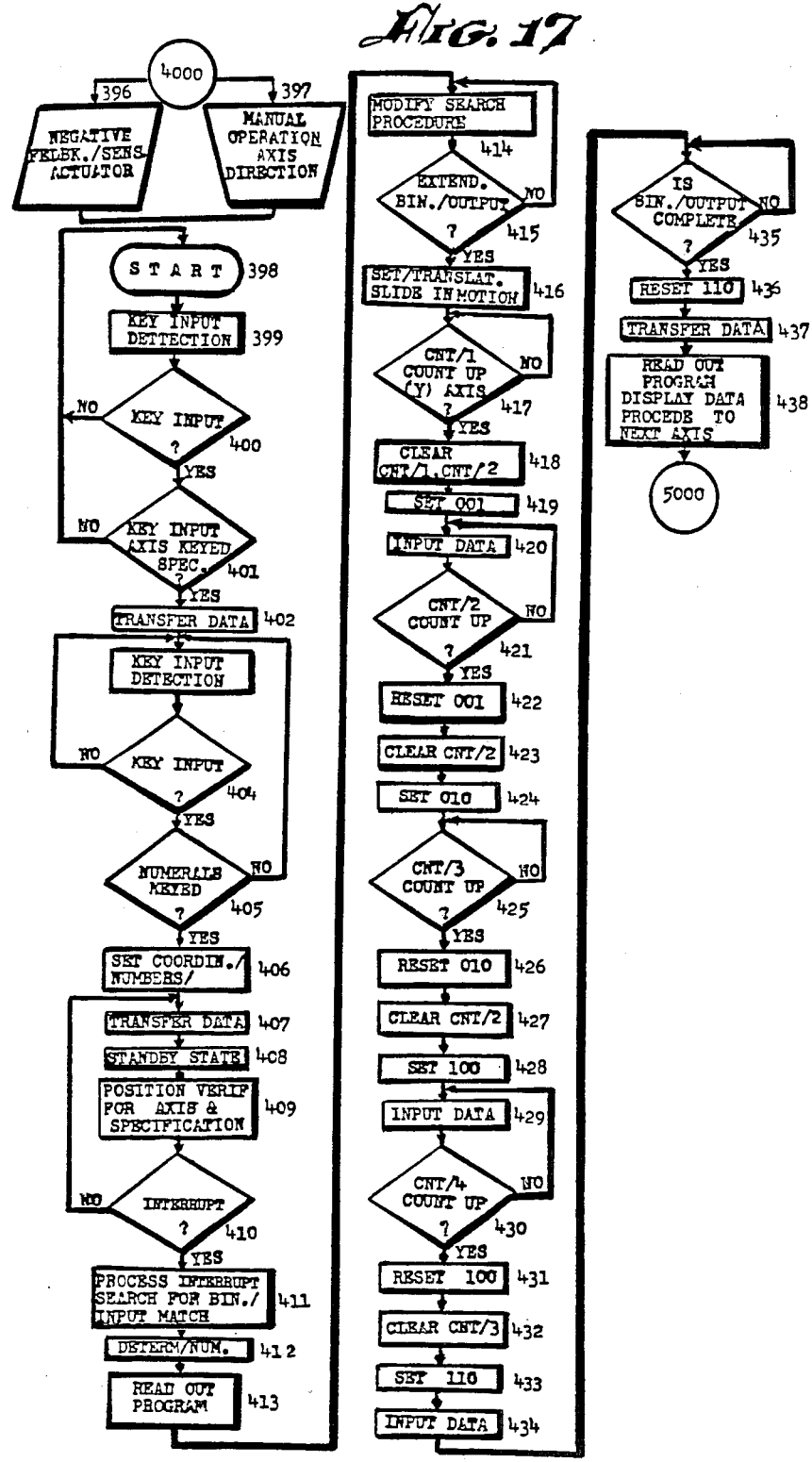
Figure 18:
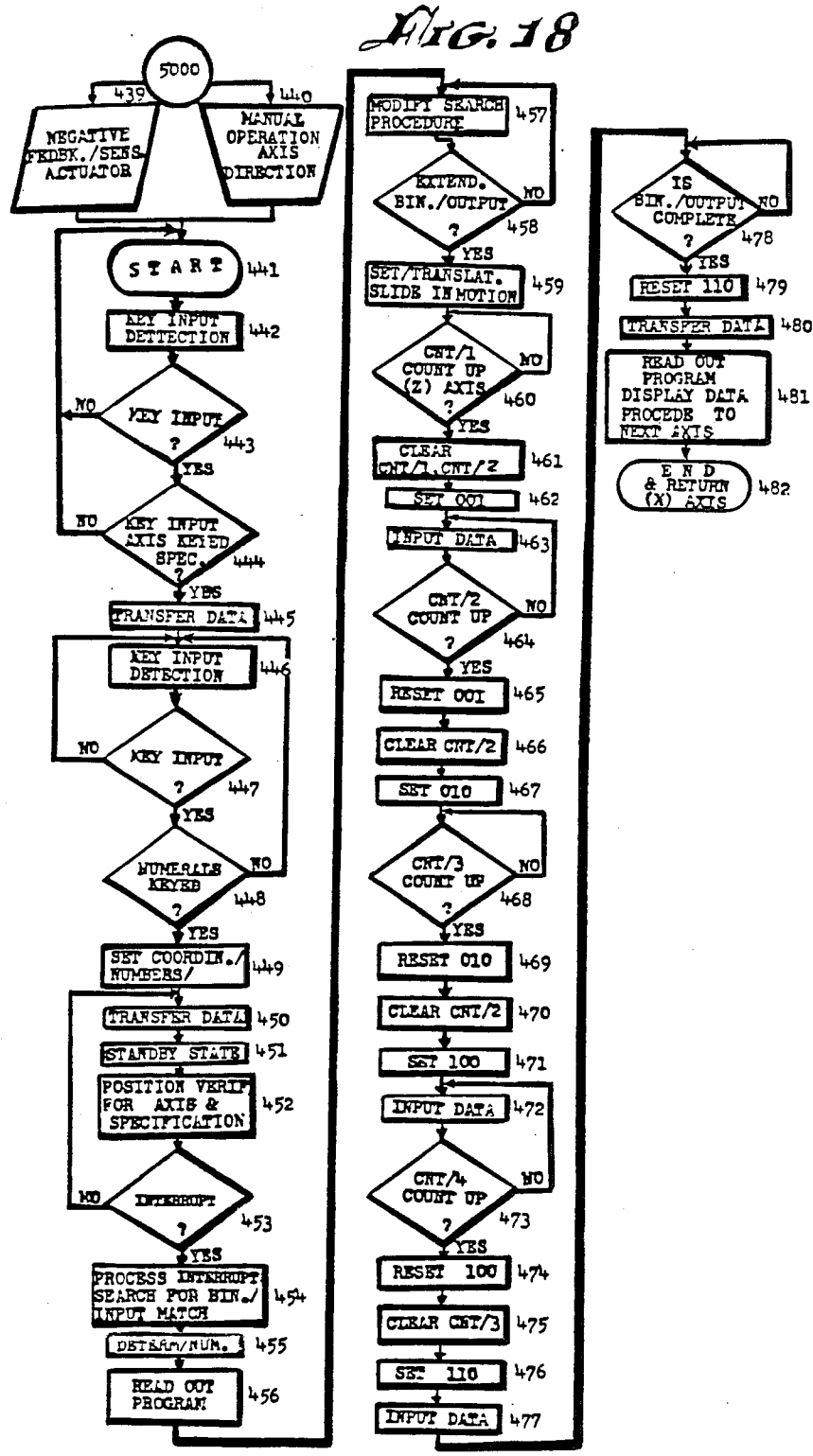

FIGS. 16, 17 and 18 are flow diagrams which collectively specify a program sequence calling for coordinated three dimensional motion of axial components, of an automated X,Y,Z, translation stage means. Each of the three subprograms governing the translational motion of the separate axial component structures are equivalent and repetitive. The initial onset and completion of a program governing motion of the X axis activates the program of the Y axis component structure, and upon completion of the programming of the Y axis the Z axial component is completed. Once all three programs are effectively executed the entire translational stage system is ready to repeat the cycle described herein the above. The start sequence numeral 355 is actuated by, either or both, the electronic negative feedback from an array of the sensors which is designated by number 353, and or the manual rotating of a separate Krul knob, 354, which provides linear motion of a translational slide along its track. The keying input undergoes data detection as described by number 356, prior to entering element 357, wherein the key sequence is verified. If the data keying is verified by element 357, then the information is conveyed to element 358, whereby specifications for keyed input determining initial axial motion is prescribed, or like numeral 357 returns its output to the start mode, number 355. Informational data transmitted to numeral 359 is transferred to a second keying input detection means denoted by number 360. The data from number 360 is received by element 361, wherein the keyed sequence is verified and sent to element 362 for numeral keying and clarification. The proper coordinate numerical data is set by element 363, and then transferred to the proper designated location by number 364. During the transferal of data by number 364 to its designated location the entire system is placed in a standby state, as denoted by numeral 365. The position verification for the axis and further specifications are depicted by number 366, which is set in operation while the slide means is in motion. A process interrupt occurs, as indicated by element 367, and procedes until the search for the proper binary input is matched between the program coordinates and the optical electronic sensors in the axial track. Once the proper coordinates are determined by number 369 the data is read in its entirety and executed, as determined by number 370. Data leaving number 370 enters number 371, which provides a modification in the search procedure, if new instructions are auto keyed in the time lag needed to put the slide in motion along its respective track. Current data from number 371 is conveyed to element 372, wherein its extended binary output is confirmed prior to sending the data to numeral 373. Numeral 373 places the slide into a maximum velocity mode. Once maximum velocity is reached the slide begins to arrive at its ultimate destination, whereby three binary count subroutines are enlisted for each binary impulse of the translational motion vector. The first counting subroutine is depicted by element 374, which specifies the given translational axis (X). The output data from number 374 is conveyed to number 375, wherein the affirmed data from count/1 is cleared and count/2 is set. Numeral 376 indicates the setting of binary code 001, which has its data input transferred by number 377 to element 378. Element 378 provides a counting interlock and verification for count/2 and conveys its output to numeral 379, which then resets binary code element 001. Number 380 clears count/2 and a number 381 sets binary code 010. Element 382 initially counts a third component from the translational vector of the X axis, and conveys its data to numeral 383. Numeral 383 resets binary element 010, and count/2 is cleared by number 384. Numeral 385 sets binary code 100 and transfers its data to number 386, where it is then conveyed to element 387. Element 387 is the fourth and final set of binary code components for the translational vector, and it confirms that an actual count up is in progress. Once the count is confirmed element 387 conveys its data to numeral 388, wherein binary element 100 is reset. Number 389 explicitly clears count/3, and numeral 390 sets binary element 110. The data from number 390 is transferred to element 392 via number 391. Element 392 verifies if the sequence of binary code elements is complete, and also that the actual absolute translational vector corresponds to or is equivalent to the translational vector called for by the program. Number 393 resets binary code 110, and numeral 394 transfers all pertinent data to numeral 395. Numeral 395 automatically reads out the specified program, displaying pertinent data on a video terminal and then signals an auto keying sequence, which instructs the system to procede to the next axis, where an equivalent series of operations will be performed. Numeral 395 of FIG. 16 transfers data to operative elements numbers 396 and 397 of FIG. 17, as indicated by numeral 4000. All functional operations, subroutines, or programming and alike are equivalent to those disclosed by FIG. 16, with the exception that the Y axis instead of the X axis is represented in FIG. 17. Numerals 396 through 438 of FIG. 17 are equivalent in every aspect to numbers 353 through 395 of FIG. 16. Data obtained from numeral 438 of FIG. 17 is conveyed to numerals 439 and 440 of FIG. 18 as indicated by number 5000. Numerals 439 through 481 of FIG. 18 are equivalent to those depicted in FIG. 17 with two important exceptions. FIG. 18 discloses equivalent data operations, subroutines, programming and alike as do FIGS. 16 and 17, however the translational vector computed and executed is for the Z axis. Another exception contained within the confines of the flow diagram depicted by FIG. 18 is that the terminal element as denoted by numeral 482 signals or flags a return to the X axis, wherein the entire cycle is repeated until all requirements are satisfied.

Figure 19:
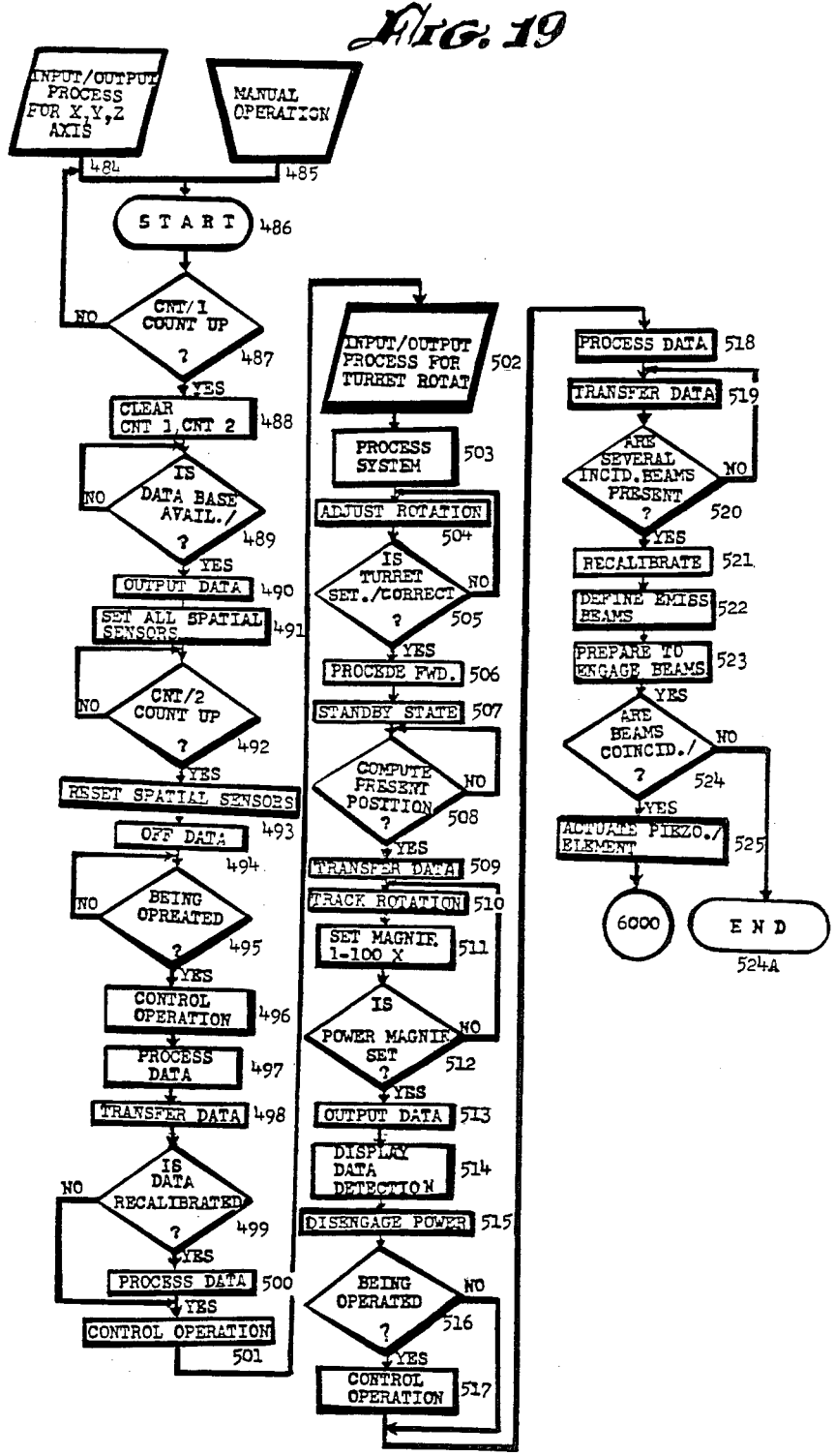
FIG. 19 is a flow diagram exacting the rotation of a multiple lense turret into a precise position.

FIG. 19 represents a flow diagram for a program which specifies the exact rotation of an automated turret structure, where one or more lense structures intercept one or more emissive beams. The initiation of start sequence number 486 is elicited by online input from either numerals 484 or 485. Numeral 484 denotes the online data received collectively by the programs governing the computation and execution of the X, Y, and Z translational vectors. Numeral 485 transfers data derived from manual operations. Element 487 is indicative of a count sequence actuating an electronic motorized unit, which is utilized to rotate the turret structure. Once the motor is activated the initial actuation input denoted by count/1 is cleared and count/2 is initiated, for the protacted operations as is prescribed by number 488. The data conveyed from number 488 is intercepted by element 489, which then verifies whether or not a data base is available and if the data is available then the output data is transferred to numeral 491 by the data output means number 490. all spatial sensors are calibrated and set by number 490 before the data is sent to element 492, which then assesses whether or not count/2 count up is available. The spatial sensors are reset in numeral 493, once the count up process has been established, and information from number 493 is then added to number 494. All incoming data is operated on by element 495, which assesses whether or not the data is being operated on. Various operational modes are enlisted by numeral 496 to perform a specific task or control operation prior to processing the data as denoted by number 497. The data is tranferred from number 497 to element 499 by way of number 498, wherein the data is recalibrated. Data from element 499 is once again processed as described by number 500, and then the data enters another control operation which is denoted by numeral 501. The data compiled by numeral 501 provides both programmed instructions and sensor feedback, which in turn initiates rotation of the turret structure, as indicated by number 502. The output derived from number 502 is processed by system 503, which transfers its data to operation 504 to perform any rotation adjustments of the turret if required. The position of the turret is monitored and verified by element 505. The turret means precedes with motion as described by number 506, whereby the entire system is put in a standby state denoted by number 507, until the present position of the turret can be verified. The data from 508 is transferred by operative number 509, so that the rotation of the turret structure can be tracted continuously, as noted by numeral 510. The lense magnification which ranges from 1:1 ratio to a 100:1 ratio is determined and set by numeral 511, which inputs into element 512. Element 512 verifies that the proper magnification has been set by optical electronic sensors, if not then the data is returned to number 510, where the turret is tracted once again. If data verification is forth coming from element 512, then the output data is read and transferred from element 512 to numeral 514, for data detection and display by number 513. Once the correct lense setting is achieved the power supplying the rotational means is disengaged, as is indicated by number 515. Data is still being operated on after the motorized unit is disengaged, locking the turret into position, as denoted by element 516. The data from 516 is collectively directed to number 517, which consists of a number of interactive operational modes, irregardless of whether a positive or negative reponse is elicited by element 516. The output derived from number 517 is processed by numeral 518, which transfers its data to element 520 by way of systems number 519. Element 520 assesses if several incident beams are present from one or more emissive sources via an array of optical electronic and positional sensors. If several incident beams are present directly, then the entire turret subsystem will undergo recalibration, as noted by number 521, or the data is returned to number 519 for further data. After the turret subsystem undergoes recalibration, then the emissive beams are defined by the operative system depicted in numeral 522. Once the emissive source is clearly defined a subroutine denoted by number 523 prepares the turret means to engage the emissive beams. If the beams are determined to be coincidental by element 524, which is incidenting on both the optical quartz lense position, along the central axis of the Coupler device 000, and also incidenting on the reflective piezoelectric means adjacent to central axis 000, then a lense element of the piezoelectric means is actuated. If multiple beams are not coincidental then the program is terminated, as denoted by number 524A. The data obtained from number 525 from FIG. 19 is conveyed to element 526 of FIG. 20 as indicated by numeral 6000.

Figure 20:
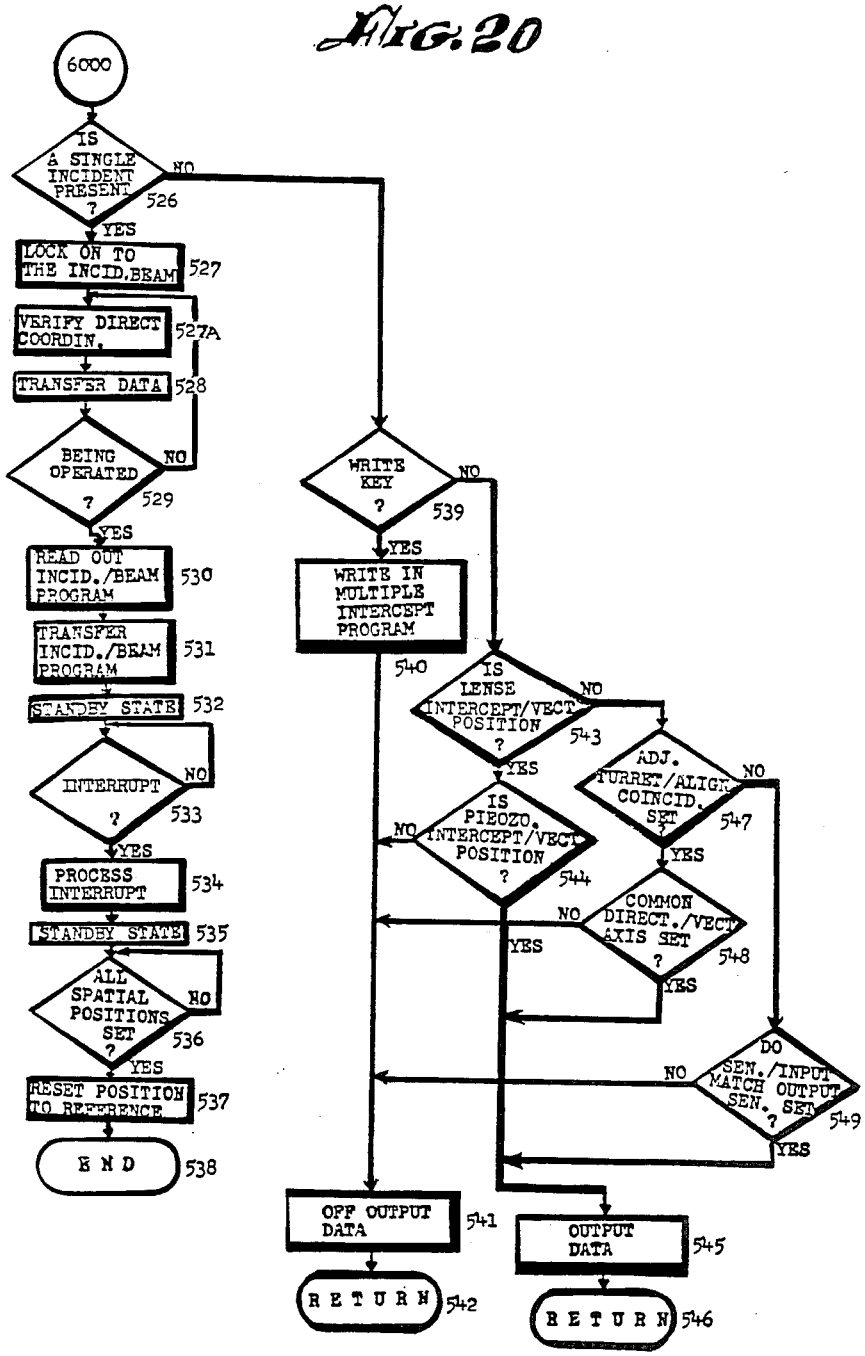
FIG. 20 is a flow diagram depicting the electronic focusing of one or more incident beams by a piezoelectric lense.

FIG. 20 is a flow diagram depicting the electronic focusing from one or more incident beams by a multifaceted reflective piezoelectric lense system. The lense system consists of a number of highly reflective parabolic mirrors, and is mounted on a rotational pivot, which is powered by the electronic motorized means previously described in this disclosure herein. The data from number 525 of FIG. 19 is intercepted by element 526 of FIG. 20, which determines whether or not a single or multiple incident beams are present. If a single beam is present the output data then precedes from element 526 to numeral 527, or the output data is shunted to element 539 when engaging multiple beams. The incident beam is engaged and locked onto a specified parabolic facet of the piezoelectric means by number 527, and the coordinates are directly verified by number 527A. Upon verification of the data derived from number 527A the transferal of data is conveyed to element 529 via number 528. Element 529 asseses if the data is being operated on, and if not then the data is sent back to number 527A, where it is acted upon further. The incident beam program which is necessary for continuous engagment of the said beam is denoted by the number 530. The data is transferred to the appropriate microprocessor element of the piezoelectric focusing means as determined by numeral 531, whereby the entire piezoelectric subsystem is put in a series of standby states and process interrupts, as denoted herein by numerals 532 through 535, until the focusing process is completely executed. Element 536 confirms that all spatial positions are correctly set via an array of optical electronic sensors located around the periphery of each focusing element. Once confirmation of positional data has occurred and the focusing process is completed, then the position and or electronic state of the piezoelectric subsystems is established, as described by number 537 prior to ending the program procedure, as noted by element 538. If multiple emissions are to be intercepted as described earlier then a new program or a modified program must be coded for the EEPROM element, which is provided for by element 539. The multiple intercept program can either be keyed manually or auto keyed as described by number 540. Number 540 conveys its data output to a compiler means denoted by number 541 prior to returning to the main computer for further instructions, as indicated by number 542. If for some inexplicable reason the keying can not be successfully written, then the data from element 539 is shunted to element 543, wherein a subroutine is enlisted establishing whether or not a specified optical lense is correctly positioned along the central axis, 000, with a systems check run on all sensor elements of the array. If all sensor elements are operational and the optical lense intercept vector coincides with the central axis position, then the data is conveyed from element 543 to element 544. Element 544 provides the necessary means to confirm the exact intercept vectors required for the piezoelectric element to be correctly positioned. If the piezoelectric element is incorrectly positioned, then the output data is shunted to computer unit 541, and returned to the main computer for further instructions. If the piezoelectric means is in the correct intercept position, then the output data is transferred to numeral 545, where it can be established whether more than one emissive beam is present. The output data receives special processing by numeral 545, whereby output data is returned to the main computer for further analysis and instructions, which is provided by numeral 546. If a negative response is elicited by element 543 then the data is shunted to element 547, which provides the necessary condition to adjust the turret and align the optical lense with the central axis, and also correcting the orbital position of the piezoelectric means. The output of element 547 is either sent to element 548 or shunted to element 549. If the proper turret adjustment can be made, then the output data is conveyed to element 548, in order to verify that a common directional vector has been set. If the necessary turret adjustments cannot be performed, then elements 547 output data is shunted to element 549, wherein the output of each sensor element is correspondingly matched with the expected output listed for each sensory means. In any event all data output derived from elements 539 through 549 are returned to the main computer complex for further analysis, information and or program implementation.

Figure 21:
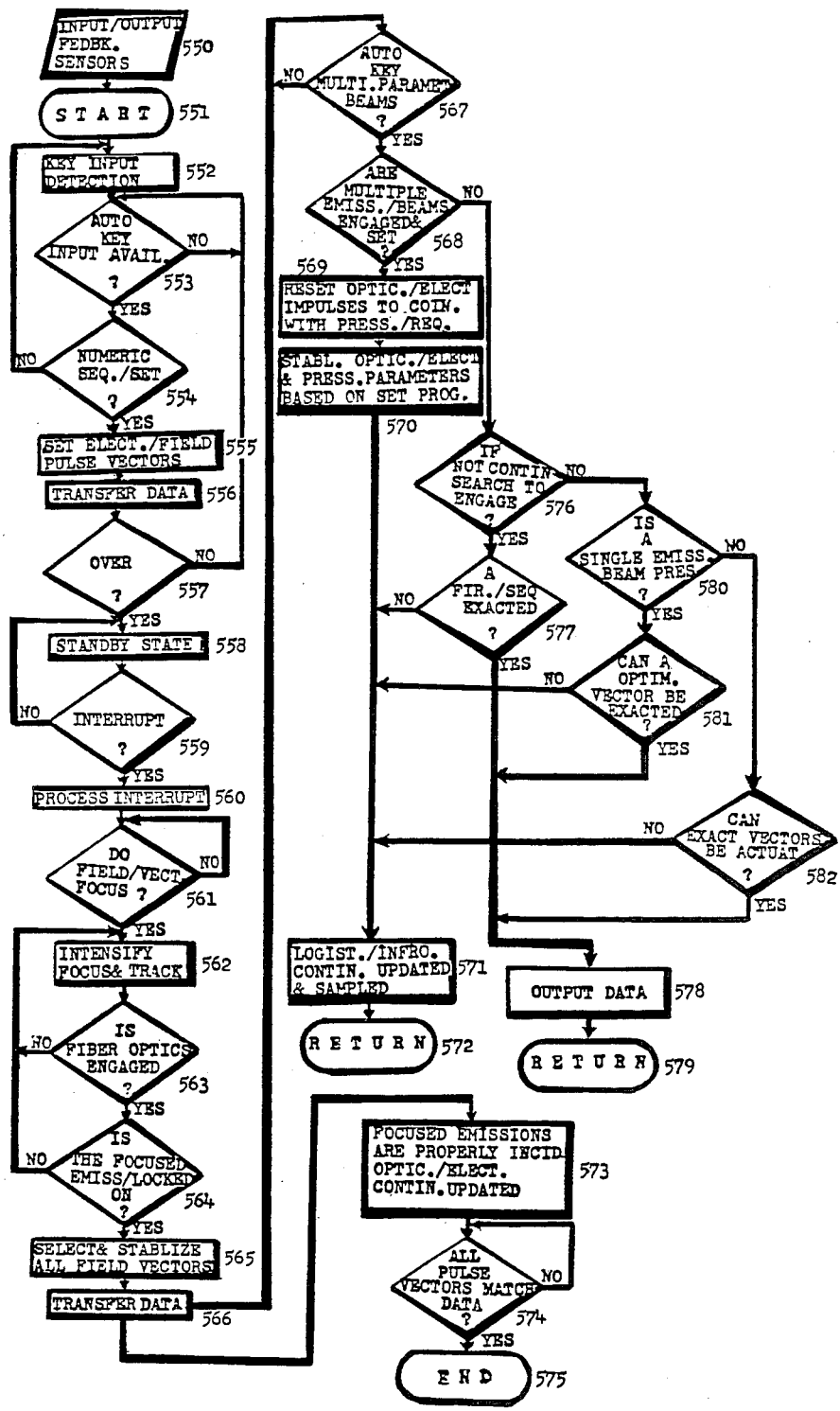
FIG. 21 is a flow diagram which encapsulates a continuation of FIGS. 19 and 20 involving the feedback acquisition of secondary targets, specifically the fiber optics directional subsystem.

FIG. 21 depicts a flow diagram specifying a program which enhances the directional and focusing capabilities of the lense turret system. Three levels of sensory feedback are available and can obtained from either electromechanical or optical electronic sensors. Sensors located on the rotational element of the turret, the piezoelectric means, and fiber optics unit provide the necessary feedback sensor data, denoted by numeral 550. The sensory input/output signals from numeral 550 actuates start sequence 551, which engages the auto key detection means described by numeral 552. Element 553 verifies if auto keying input is actually available and if so conveys its output to element 554, establishing whether or not numeric sequencing is available. If data is available for either element 553 or 554, then output is recycled to the data detection mode. Element 554 conveys its output data to numeral 555, wherein the electrical field generator component of the piezoelectric means pulse vectors are set. The data from numeral 555 is then transferred to element 557, by numeral 556. Element 557 detects whether or not the delivery sequence is over, and then the data is channeled to either element 553 or placed in a standby state, as denoted by number 558. The standby state, numeral 558 is followed by interrupt 559 and process interrupt 560. Element 561 establishes whether the electronic field vectors will provide an adequate focusing of emissions onto the fiber optics unit. The focus intensification and tracking of the emission source onto the fiber optics unit is prescribed by number 562. A optical electronic sensor network surrounding each optically emissive element of the fiber optics unit determines whether or not a specified fiber optics element is engaged, as denoted by numeral 563. If the proper fiber optic elements are engaged, then it becomes necessary to detemine if the emission is not only focused onto a given fiber optic element, but completely locked onto the said fiber, as exacted by element 564. Both elements return their outputs to numeral 562 if a negative response is elicited. Once the emissive sources are adequately focused and locked onto a specified fiber optics element, the field vectors selected are stabilized, as expressed by number 565. The data from number 565 is then transferred to element 567 by numeral 566. It is in element 567 wherein multiple parameter beams are auto keyed and set. The output data from numeral 567 is either returned to number 566 for further supplementation with additional data, or sent to element 568, whereby the multiple emissions are assessed on the basis of whether or not they are engaged or not. If the beams are engaged the data is then sent to numeral 569. However, if the beams are not engaged data is then shunted to element 576, wherein the piezoelectric element, and if warranted the entire turret structure are set in a predetermined search mode pattern, until the proper vectors are engaged. Upon confirmation that the beams are correctly engaged, focused and targeted, the optical electronic impulses are altered to coincide with the pressure or torque requirements of the piezoelectric menans, as described by numeral 569. Numeral 570 enlists a stablization procedure which maintains various optical electronic and pressure parameters to optimize the focusing of specified emissions. Data from number 570 is conveyed to numeral 571 which then supplies logistical information, which is continuously obtained from an array of sensory devices before its returned to the main computer for further instructions as required. The data transferred from numeral 566 is also sent simultaneously to element 567, as previously stated and numeral 573, wherein it is established that all emissions are incidenting properly on their respective targets. The data from numeral 573 is sent to element 574 where all pulse vectors must match those values contained within the prescribed program, and then once exacted, the program is abruptly terminated, as denoted by number 575. As previously noted data from 566 is transferred to element 567, which conveys its data to element 568. However, if the emissive beams can not be engaged for targeting, then the data is shunted from element 568 to element 576, where it is detemined that if the emission sources are not continuously engaged by either the piezoelectric means or a quartz lense element of the turret structure; then a search is engaged involving program data collectively received by the main computer complex from other subsystems of the Coupler device. If the data conforms to that which is specified by other programs, such as those programs which govern the time interruptions by the shutter means or modulated characteristics specified by the chopper complex, then the data is conveyed to element 576. The data from element 576 is then conveyed to either element 577 or to element 580 depending on the condition encountered by subroutine 576. Element 577 determines if a directional firing sequence is exacted and executed by other ongoing programs. If a firing sequence is exacted then the data is transferred to compiler means 578, which sends its data back to the main computer complex, where it is enhanced and acted upon further as prescribed by element 579. The data which can not be acted upon by element 576 is then shunted to element 580, which determines whether or not a single electronically complexed emission beam is present, and if so conveys its data to element 581. However, if a single complex beam is not present, then the data is shunted to element 582. Element 581 establishes wheter or not an optimal vector can be exacted for the said complexed emissive beam. Element 582 assesses whether an exact set of vectors can be actuated or not. As the observer can readily see from the flow diagram depicted in FIG. 21 that irregardless of whether or not a positive or a negative response is elicited by elements 576 through 582, the output of data is ultimately conveyed to the main computer complex, as denoted by numerals 572 and 579.

Figure 22:
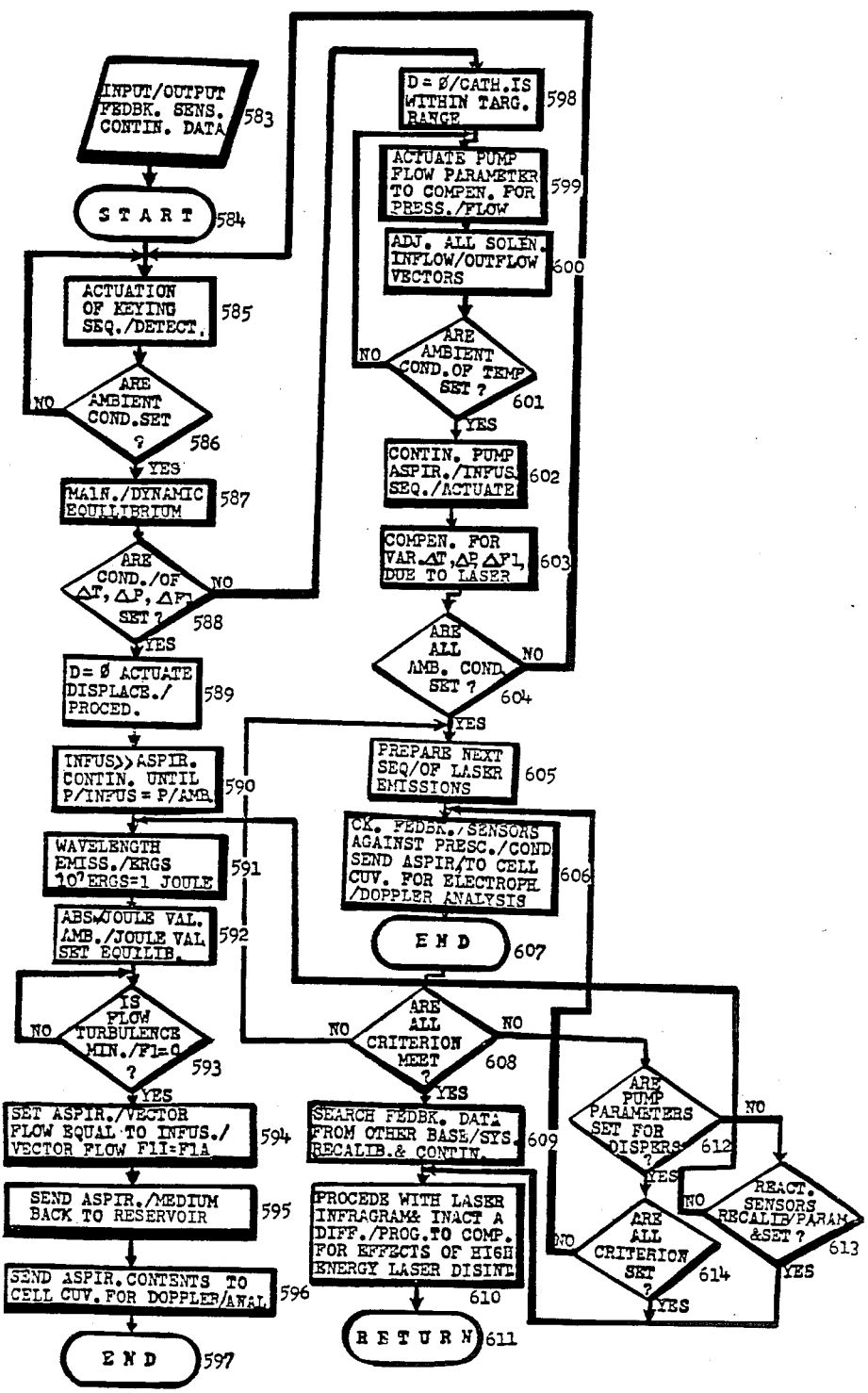
FIG. 22 is a greatly simplified flow diagram which provides a series of compensatory actions in response to alterations in the ambient pressure, temperature and flow of the target region.

FIG. 22 depicts a simplified flow diagram denoting a complex program sequence, which provides for a series of compensatory actions that are initiated in response to alterations in the ambient pressure, temperature, and the flow or turbulence for a given primary target region. Data derived from numerous sensors, which arrive continuously at the aspiration infusion pump are, denoted by numeral 583. Numeral 583 actuates the start sequence 584, which elicits the actuation of a keying sequence detector as noted by numeral 585. The data from number 585 to element 586 determines whether or not ambient conditions are set, and then the data is sent to number 587. However, if a negative response is elicited, then the data is recycled back to number 585 for further processing. Element 588 verifies if the difference in temperature $\Delta T$, the difference in pressure $\Delta P$, and the difference in flow $\Delta Fl$ are set. If values $\Delta T$, $\Delta P$, and $\Delta Fl$ are ascertained, then the data is channeled to numeral 589. If verification is however not attainable, then the data is shunted to number 598. Numeral 589 actuates the displacement procedure, whereby infusiate displaces hemoglobin or a similar such medium. Once displacement is properly executed the rate of infusion exceeds the rate of aspiration; and the process continues until the pressure of the infusiate equals that of the ambient conditions, which are denoted by number 590. The temperature of the infusiate which is caused by the emissive source is calculated either in ergs or joules as, indicated by numeral 591. The absolute joule value of the infusiate undergoing laser bombardment versus the ambient joule value are both duely noted, set and equilibrated, in number 592. During a lasing sequence temperature directly effects pressure, which inturn directly effects flow; therefore the flow parameters must have a verifiable minimum flow differential as prescribed by element 593. Once displacement is completed the aspiration flow vector is set equal to the infusion flow vector, establishing dynamic equilibrium, as noted by numeral 594. The aspiration medium is tranferred back to a holding reservoir, which is described by number 595. The aspired contents are further transferred to a cell cuvette for doppler analysis, which is indicated by numeral 596; then when completed it terminates the operation denoted by number 597, until the cycle is reinstituted. In the event that the conditions prescribed by element 588 are not meet, then the data is conveyed from element 588 to number 598. Then the distance of the catheter from an operative target site is computed, and the proper displacement is exacted. The pump is actuated to alter flow parameters in a specific manner, as to compensate for discrepancies in pressure or the flow induced by the displacement process, as described by number 599. Adjustment of inflow/outflow vectors are initiated by numeral 600. Data from numeral 600 is transferred to element 601, which assess conditions of ambient temperatures, which must be maintained or set through the entire operation of the pump means. If the temperature is not set, then data from 601 is transferred to numeral 599. However, if confirmation for element 601 is established, then the data is conveyed to number 602, which maintains pump operation and actuates subroutine, number 603 wherein $\Delta T$, $\Delta P$ and $\Delta Fl$, due to laser bombardment can be duely compensated. Element 604 receives data transferred from number 603, and then confirms whether or not ambient conditions have been meet. If these ambient conditions have not been meet by element 604, then the data is shunted back to the start sequence. However, if confirmation occurs then the data is conveyed to numeral 605. Numeral 605 prepares the pump means for compensatory measures concerning laser bombardment. The data from 605 is conveyed to number 606, wherein a systems check is performed on the feeback sensors, and aspirant transferred to curvettes for doppler analysis and microelectrophoresis, prior to program termination as denoted by number 607. Once the program ends, as indicated by number 607, the termination flags element 608, where it is determined if all criteria has been met. If all criteria has not been met, then the data re-enters the program and is recycled to numeral 605 for reassessment. If confirmation in element 698 occurs then the data is sent to number 609 however; if unconfirmed, then it is sent to element 612. It is in number 609 wherein sensory feedback data which is derived from other base systems augments the data, which is transferred from element 608. The data from 609 is conveyed to number 610, wherein laser infragrams are exacted and a subprogram is initiated, to further compensate for the effects of high energy disintegration. The data from number 610 is transferred to numeral 611, which depicts the main computer complex, where further instructions and analysis occurs. Element 612 confirms whether or not the pump unit is provided with the necessary parameters, which allow the target site to undergo the correct dispersal procedure. If a positive response is elicited by element 612, the data is then conveyed to element 614. However, if a negative response is elicited, then the data is shunted to element 613. Element 614 establishes whether or not all criterion is set, if not, the data is then sent to be reprocessed, and is added to the output of numeral 609. It is within element 613 wherein reactions are monitored by sensors, which set thermal and convective flow parameters. When data is verifed by element 613, then its output is channeled like that of element 614, to be collectively added to the output of number 609, which eventually will be sent back to the main computer for further action. If a negative response is elicited by element 613, then the data output is conveyed back to the mainline to be combined with the output data of numeral 590.

Figure 23:
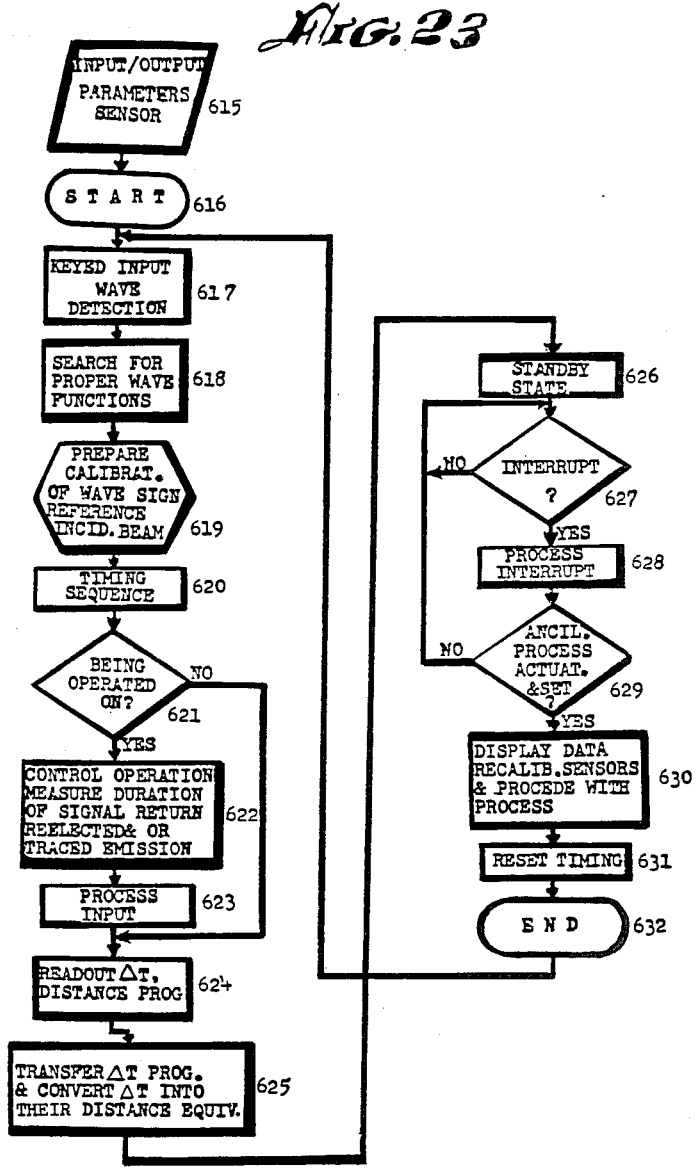
FIG. 23 is a flow diagram for a basic program which measures distance of the emissive fiber optics element from a specified target on the basis of signal time differentials.

FIG. 23 is a representative flow diagram for a basic program, which precisely measures the distance of the emissive fiber optics element from a given target, on the basis of signal time differentials. The input/output parameter is a low level emission signal which is bounced or reflected from the target site, and it can be effectively assessed by onboard catheter based sensors, as denoted by numeral 615. The input/output parameters actuate the start sequence indicated by numeral 616. The initiation of the start sequence actuates the auto keyed wave detection spectrum analyzer number 617, which then engages number 618. Number 618 represents a single optical electronic memory chip, which is incorporated into the catheter structure, and which is keyed to search for unique and properly specified wave functions. The data received from number 618 is further prepared and calibrated, such that the wave sign of the reference beam which incidents on the specified target is logged, as described by number 619. Once the data is properly logged, then it is set into an on going timing sequence denoted by numeral 620. The data output derived collectively from numerals 617 through 620 is acted upon, and verification of this continuous process is established by numeral 621, where if a negative response is elicited the data is then shunted to number 624. If confirmation is established such that the data is being operated on, then the collective data is conferred to numeral 622. It is in numeral 622 wherein the control operation measuring the duration of a signal, which is returned by either reflection or traced re-emissions derived from the target site is assessed. The input is processed by a priority compiler means which is described by number 623. The wave differential ΔT is read out in relation to a deterministic subprogram, which defines distance as a function of time, as noted by numeral 624. An ancillary subroutine of numeral 624 is denoted by number 625; and the transference of all ΔT program data is then converted into their digitized binary distance equivalents. As the various operations are performed on the data in number 625, the entire system is placed in a standby condition denoted by number 626, which is then followed by an interrupt/process interrupt condition, described by numbers 627 and 628. This is done until an ancillary process of gauging data is actuated, set and confirmed by element 629. The data is then conveyed from element 629 to number 630, where it is displayed continuously to denote vector position of the specified target site relative to the catheter means; while sensors undergo repeated recalibration after each measurement is exacted. Once the process denoted by numeral 630 has completed one phase of the operation, an output signal reseting the timing sequence is inacted and duely noted by numeral 631; and then the entire program is terminated, as indicated by number 632. At the point of program termination, number 632, a termination signal is sent to numeral 617 to flag its operation.

The following mathematical equations derivations are employed in accordance with the invention herein below: A subprogram yield Δt difference between a reference beam and the emissive return or reflection of a said beam, both taken over time yielding the absolute target distance.

$$<I(\tau_1, t_1) I(\tau_2, t_2)> = <|F(\tau_1, t_1)|^2 |F(\tau_2, t_2)|^2>$$
$$= <F^*(\tau, t_1) F^*(\tau_2, t_2) F(\tau_2, t_2) F(\tau_1, t_1)>$$

Gausian light for the cycles average intensity is $$I(\tau,t) = F^*(\tau,t) F(\tau,t) = A^2 \left[ N + \sum_{\substack{m,n=1 \\ m \neq n}}^{N} e^{i(\phi m - \phi n)} \right]$$

For a relatively long duration of time the product of the two intensities becomes $$I<(\tau_1, t_1) I \cdot (\tau_2, t_2)> = A^4 \left[ N^2 + <\sum_{\substack{m,m=1 \\ m \neq n}}^{N} e^{i[\phi m(t_2) - \phi n(t_2)]}\right.$$

$$\left. \sum_{\substack{i,j=1 \\ i \neq j}}^{N} e^{i[\phi i(t_1) \phi i(t_1)]} > \right]$$

where the cross terms average to zero Let $$<\sum_{\substack{m,n=1 \\ m \neq n}}^{N} e^{i(\phi m - \phi n)}> = 0$$

Condition when m=j and n=i the product of sum is as follows:

$$A^4 < \sum_{\substack{m=j=1 \\ m \neq n}}^{N} e^{i[\phi m(t_1+r) - \phi n(t_1)]} \sum_{n=j=1}^{N} e^{-i\phi n(t_1+r) - \phi n(t_1)} >$$

∴ time averages are taken for each sum independently such that $$<F^*(r_1,t_1)F(r_2,t_2)>$$

producing the final value $$<I(r_1,t_1)I(r_2,t_2)> = <I>^2 + <F^*(r_1,t_1)F(r_2,t_2)>^2$$

By the process of normalizing the averages a second order correlation function is exacted the derived value being:

$$g_{12}^{(2)} = \frac{<I(r_1, t_1)I(r_2, t_2)>}{I<(r_1, t_1)><I(r_2, t_2)>}$$

When sampling data from wave fields from any four space-time points the second order of correlation becomes:

$$g^{(2)}(r_1\ t_1, r_2\ t_2; r_3\ t_3, r_4\ t_4) =$$

$$\frac{<F^*(r_1\ t_1)F^*(r_2, t_2)F(r_3, t_3)F(r_4, t_4)>}{(<|F(r_1, t_1)|^2><|F(r_2, t_2)|^2><|F(r_3, t_3)|^2><|F(r_4, t_4)|^2>)^{\frac{1}{2}}}$$

Figure 24:
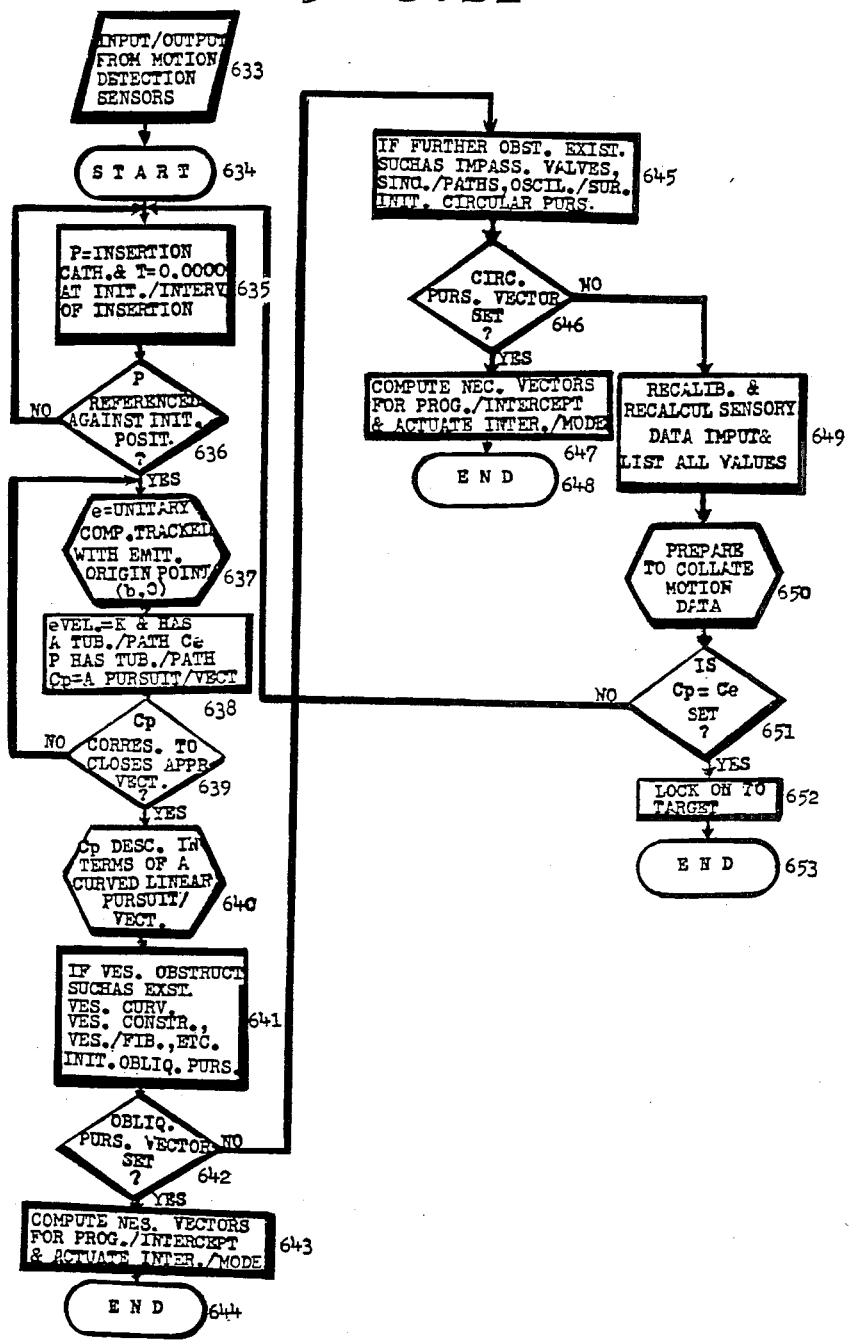
FIG. 24 depicts a flow diagram for a program specifying the optimum path needed to reach a given target.

FIG. 24 depicts a flow diagram for a program which specifies the optimum path needed to reach a given target site. The input/output derived from motion detection sensors is signified by number 633, which actuates start sequence, number 634. The insertion of the catheter means P occurs initially at time T, which equals 0.0000 seconds, the initial interval of insertion, as indicated by number 635. The data from number 635 is conveyed to element 636, wherein P the insetion catheter is referenced against its initial position at time T equals 0.0000 seconds. A preparatory operation is enlisted, whereby e is defined as the unitary component and a tracked emitter with origin point (b,0) of the specified target site is prescribed by numeral 637. Numeral 638 is a definative process which describes the vector component eVeL=k, which has a tubular path, Ce and P also has a tubular path, Cp, a specified pursuit vector. Element 639 verifies whether or not Cp corresponds to its closest approach vector, and if a positive correlation is exacted, then the data from element 639 is conveyed to number 640 or reconveyed to numeral 637 for further processing. Cp is then described in terms of a curved linear pursuit vector, as defined by numeral 640. Numeral 641 is a prescribed avoidance subprogram in the eventuality that a given vessel or corridor is being constricted severely curved, undergoing fibrilation, or otherwise obstructed, such that an oblique pursuit rather than a curved linear pursuit is needed. Element 642 establishes whether or not a oblique pursuit vector satisfies the optimum targeting requirements, or if it has to be shunted to another mode of engagement prescribed by numeral 645. If the oblique pursuit vector can be exacted, then element 642 conveys its data to numeral 643, where the necessary vectors for programming an optimum intercept is activated in a data interactive mode. Once the data passes from the interactive mode, number 643, then all values are exacted and the target is engaged. The program's operation in regards to oblique pursuit is then terminated, as denoted by number 644. As previously noted if an oblique pursuit pattern is deemed ineffectual or unsatisfactory for engaging a said target, as determined by element 642, then the data is shunted to numeral 645. Numeral 645 is a subprogram which determines if further obstacles exist such as impassible valves, sinuous paths, or oscillating surface parameters, with a circular pursuit pattern initiated or in effect. Element 646 establishes whether or not a circular pursuit vector is set. If the circular pursuit is in effect then the data from 646 is sent to numeral 647, wherein the necessary vectors for a circular pursuit and intercept program is computed, and an interactive mode is actuated. If the subprogram is properly executed, whereby all conditions are satisfied as denoted in numeral 647, then the program is abruptly terminated as indicated by number 648. If however, as noted earlier a negative response is elicited from element 646, then the data is shunted to numeral 649, where the sensors are recalibrated, the sensory data is recalculated and all values are listed. Numeral 650 is a subroutine which prepares and collates all motion data. The data from number 650 is then conveyed to element 651, where it is determined whether Cp equals Ce. If Cp does equal Ce, then the catheter locks onto target and engages it as noted by numeral 652, whereby the program is once again abruptly terminated, as indicated by number 653. If a negative response is elicited, such that Cp≠Ce, then the data is shunted from element 651 to the mainline start sequencing mode, number 634. The motion of the insertion means relative to targeting, as it concerns laser telemetry and tracking behavior. The following definitions, mathematical equations and derivations are employed in accordance with the invention as described by the following pages herein;

MOTION OF INSERTION MEANS, LASER TELEMETRY & TRACKING BEHAVIOR

Let an arbitrary point P represent the insertion means and t equal 00.0000 for the initial insertion starting time from the origin of the X,Y,Z axis.

Let a group of arbitrary points denoted by e consist of the unitary components to be tracked and its starting point or origin is at a designated location (b, 0).

e is assumed to move at a constant ambient speed k, along a tubular path as denoted by Ce.

P moves along the tubular path Cp. Cp pursuit curve will be linear an correspond to Ce unless specified otherwise. Cp described in terms of an X,Y,Z axis, or n axis corresponds to a geodesic pursuit on a curved surface, pursuit may be cyclic or otherwise.

Let $Y = f(X)$ represents the initial equation of Cp. For Cp utilize arc length proportional curve to give condition $|Be| = ks$. Where s equals length of pursuit or the distance between target loci and insertion means then;

$$(b-X)Y' = ks - Y$$

$$(b-X)Y'' = k(i+Y^2)^{\frac{1}{2}}$$

Set initial conditions $Y(0) = Y'(0) = 0$ Since Y is inferred the order is reduced by taking Y, such that Y' is now dependent and Y' is independent. Then solve for Y $$Y = \frac{b}{2}\left[\frac{(1-X/b)^{1+k}-1}{1+k} - \frac{(1-X/b)^{1+k}-1}{1-k}\right], k \neq 1$$

$$\frac{b}{2}\left[\frac{(1-X/b)^2}{2} - \log(1-X/b)\right], k = 1$$

Second condition:

If pursuit cannot be achieved by linear means then try an oblique pursuit pattern $$(b - X + ks \cos \alpha)Y' = Ks \sin \alpha - Y$$

$$Y(0) = Y'(0) = 0$$

b sin α replaces b and initial condition are $Y(0) = 0$, $Y'(0) = COt\alpha$.

e is engaged by P if and only if K<1 with X=b the engaging area is denoted by (b, Kb/(1−K²)) When K>1, e is further away from P and the insertion means is moving away from the target site.

If K=1 the distance is asymptotically attained between panel P and e such that $$\lim_{x \to b}(s - y) = \lim_{x \to b}(b - x)y' = \frac{b}{2}$$

If pursuit is circular then Cp is a circular path and the polar coordinates are defined by $P = P(\theta)$, $\phi(\theta)Cp$ and the systematic path is described by $$\phi' \frac{a}{p} \cos \phi - 1$$

$$P' = a \sin \phi - \frac{a}{K}$$

such that, $$\frac{dP}{d\phi} = P\frac{a(\sin \phi - 1/K)}{a \cos \phi - P}$$

$$K < t$$

Figure 25:
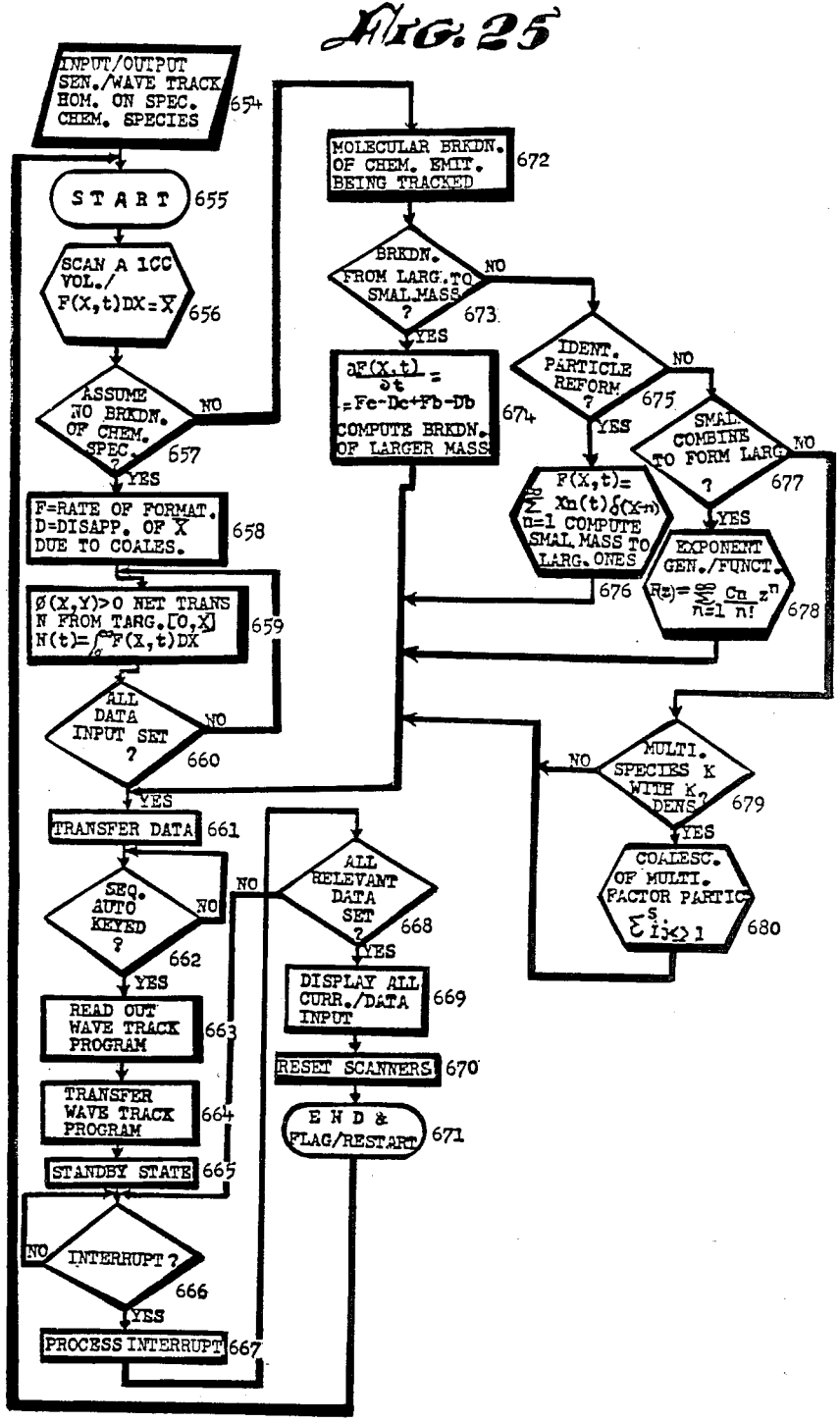
FIG. 25 is representative of a flow diagram which calls for a program that continuously scans complex chemical species.

FIG. 25 is a representative flow diagram calling for a program which continuously scans for complex chemical species. The input output sensory data locks onto the specified chemical species they were designed to home in on, as denoted by number 654. The data from number 654 activates start sequence 655, which initates the repeatative scanning of a one cubic centimeter volume of homogenate for values of $F(X, t)DX = X$, in dynamic flux, as described by number 656. The data from number 656 is channeled to element 657, where it is assumed that no breakdown of chemical species occurs from larger complexed molecules to their smaller constituent parts, which is then verified. If verification occurs then the data is sent to numeral 658, and if unsubstantiated the data is then sent to number 672, for further analysis. The data that is confined to number 658 establishes the rate of formation, F, and the rate disappearance, D, due to coalescence from mass X. Numeral 659 the net transport of mass N from a specific target loci [O,X] such that $$N(t) = \int_0^\infty F(X,t)\, dX.$$

The data from 659 is conveyed to element 660, where it is determined whether or not all data input is set. The data from element 660 is ultimately transferred to element 662 via numeral 661. A sequence of subroutine is auto keyed by element 662. Numeral 663 initiates a subprogram, which readsout a wave tracking procedure. The data is then transferred by element 664, prior to entering standby state 665, and the interrupt and process interrupt, as denoted by element 666 and 667. Element 668 establishes whether or not all data is relevant, and if its determined irrelevant the output is recycled to interrupt element 666, otherwise the data is channeled to numeral 669. Numeral 669 displays all current data received and updates its status. The scanning subprograms and sensors are reset in numeral 670, whereby the impulses exiting from numeral 670 terminate the program. Number 671 indicates a program termination, which when completed sends a signal that flags a restart of the start sequence. As noted earlier in this disclosure a negative response elicited by element 667 actuates a subprogram, which is specified by number 672. Within the confines of number 672 is computed a program to track, a chemical emitter, which undergoes molecular breakdown or degradation. Element 673 considers whether the degradation occurs due to a breakdown of a large chemically complexed species into smaller masses. Data from element 673 is either conveyed to element 675 if a negative response is elicited, or to number 674 if a positive confirmation is established. Number 674 computes and monitors the breakdown of a large complexed molecule to its smaller constituent parts, such that $$\frac{\partial F(X,t)}{\partial t} = Fc - Dc + Fb - Db.$$

The data from number 674 when fully computed re-enters the mainline program, wherein it is collated with data transferred from number 661 to element 662. If however, the breakdown process is undergoing reintegration or reformation of the smaller constituent parts into a larger complexed mass, then the data from element 673 is sent to element 675. Element 675 establishes if the process whereby particle reformation occurs can be identified, or not, based on subprograms. If identification occurs and is confirmed by element 675, then the data enters number 676 or the data will be shunted to element 677. Number 676 denotes a prepartory operation, which computes the formation of specific large masses from a number of smaller masses, as is described by the equation $$F(X,b) = \sum_{n=1}^{\infty} Xn(t)\, \delta(X-n),$$

where n=1. All data which is processed by either elements or numbers 674 through 680 re-enters the main program sequence, via a single transfer compiler means, which is designated by numeral 661. Element 667 denotes if the smaller component chemical species congregate, and then they adhere or coalesce to form larger chemically complex molecular masses. If a negative confirmation occurs then the data is shunted from element 677 to element 679, however if a positive affirmation of data occurs, then the data is channeled from element 677 to numeral 678. Numeral 678 denotes a prepatory process, where transport function F is an expoental generating function, such that $$F(Z) + \sum_{n=1}^{\infty} \frac{Cn}{n!} Z(n).$$

The data is conveyed from number 678 along a common channel with 676 to number 661, and thereby re-enters the main program sequence. The data is shunted from element 677 and enters element 679, where it is assessed whether or not if multiple species K exists with a K number of densities. If multiple species do in fact exist, then the data from 679 is first processed by preparatory operation 680, prior to being recycled to the main program sequence. However, if a negative response is elicited by element 679, then the direct transferral of data occurs at number 661. Numeral 680 determines a preparatory operation which assess the transport of multifactored particles, which are undergoing coalescene as prescribed by $$\epsilon^s i j <> 1.$$

The mathematical basis for tracking certain specified chemical species by thier spectral identity is provided by variations of well established mathematical equations, derivations and the like are employed in accordance with the invention herein below;

Homing in on specified chemical species by laser telemetry. Large numbers of mass particles are described randomly mixing, such that certain pairs of particles meet and coalesce. Let f (x,t) dx be the mean (X̄) number of particles per unit volume of particles in a mass range from X to x+dx at time t. Let the randomness of coalesing its dependence on masses of coalesing be described by f (x,t) f (y,t) φ (x,y) dx dy dt assume no breakdown from large species to smaller parts $$\partial F\frac{(x,t)}{\partial t} = F - D$$

F=rate of formation of masses x out of pairs y and x−y, while D is the rate of disappearence of masses x due to coalescence with y to form mass x+y, such that $$\frac{\partial F}{\partial t} = \tfrac{1}{2} \int_0^x f(y,t) f(x-y,t)\phi(y, x-y)\,dy - f(x,t)\int_0^\infty f(y,t)\phi(x,y)\,dy$$

If φ (x,y)>0 there is a net transport of mass N from a specified target loci [o,x], such that $$N(t) = \int_0^\infty f(x,t)\,dx$$

-continued $$\frac{dN}{dt} = \int_o^\infty \int_o^\infty \phi(x,y) f(x,t) f(y,t) \, dxdy \, N,$$

unless $\phi = 0$ when $\phi(x,y) = c(x+y)$ c=positive constant
then $N' = -2cMN$
M is the constant total mass $$M = \int_o^\infty x f(x,t) \, dx$$

such that N(t) N(o) e−2 Mct
if $\phi(x,y) = cxy$
then $N' = -cM^2$
$N(t) = N(o) - cM^2 t$
target particle breakdown $$\frac{\partial f(x,t)}{\partial t} = Fc - Dc + Fb - Db$$

Fc=F Dc=D Fb=rate of particle formation of masses x from the breakdown of larger ones
Db=rate of disappearance of x's due to breakdown $$\frac{\partial F}{\partial t} = \tfrac{1}{2} \int_o^x f(y,t) f(x-y,t) \phi(y,x-y) \, dy -$$

$$f(x,t) \int_o^\infty f(y,t) \phi(x,y) \, dy +$$

$$\int_o^\infty f(y,t) \psi(y,x) \, dy - \frac{f(x,t)}{x} \int_o^x y\psi(x,y) dy$$

$$\frac{\partial F}{\partial t} = A_2(F) + A_1(F) - B_2(F) - B_1(F)$$

where A's and B's are all positive operators. $A_2$ and $B_2$ equal quadratic breakdown operators. $A_1$ and $B_1$ are linear.

$$\frac{\partial F}{\partial t} = A(F) - B(F,$$

$$A(F) = \sum_{n=1}^\infty A_n(F), \, B(F) = \sum_{n=1}^\infty B_n(F)$$

If identical particles of equivalent masses form with one another to double, triple ... n triples mass at time t as in the case of certain papillary tumors, or cholesterol then:

$$X'n(t) = \tfrac{1}{2} \sum_{K=1}^{n-1} X K(t) X n - K(t) - X n(t) \sum_{K=1}^\infty XK(t)$$

where n=1, 2 ...
$XK(0) = 0$
$K > 1$
$X_1(0) = N$ $$F(X,t) = \sum_{n=1}^\infty Xn(t) \delta(X-n)$$

four pairs of masses combine to form single larger ones, n triples of masses coalesce to form protienoids $$N(X_1 \ldots X_n \, t) \, dX_1 \ldots dX_n \, dt = \phi(X_1 \ldots Xn) \, dt \prod_{i=1}^n [f(Xi,t) \, dX_i]$$

n=transport $$\frac{\partial F(X,t)}{\partial t} = \frac{1}{n!} \int_{o \leq Xi} \ldots \int N(x1, \ldots Xn,t) \, dX_2 \ldots dXn -$$

$$\frac{1}{(n-1)!} \int_n^\infty \ldots \int_n^\infty N(X_1 X_2 \ldots Xn \, t) dX \ldots dXn$$

transport function F an expoental generating function $$F(Z) = \sum_{n=2}^\infty \frac{Cn}{n!} Zn$$

where Cn=CnK if n is the sequence $n_1, n_2 \ldots nK$

A condition a transport model with K different species, with K different density functions Fi(X,t), i=1, ... K particle of mass X and type i can coalesce with a particle of mass Y and type j to yield a particle of mass X+Y and type S model for suspension of molecules.

$\epsilon^s ij = 1$ or 0

$\epsilon^s ij \geq 0$ and $\sum_5 \epsilon^s ij \leq 1$ for fixed i, j $$\frac{\partial g}{\partial t} = \sum_{i,j} \epsilon^s ij \, d \, ij \, C \, ijgi \, j \, (P,t) gj \, (P,t) -$$

$\sum_{ij} e^j$ is $C$ isgi $(O,t)$gs $(P,t)$ $s = 1, 2 \ldots K$ total number of individuals of the sth kind at time t $$gs(O,t) = \int_\infty^o Fs(X, t) \, dx = Ns(t)$$

$N^1 s = \sum_{ij} \epsilon^s ij \, d \, ij \, C \, ij \, N \, i \, Nj - \sum_{i,j} e^j$ is $Cis \, Ni \, Ns$ s=1, ... K chemical Kinetics=K, K species N i binary interactions of reacting molecules.

Figure 26:
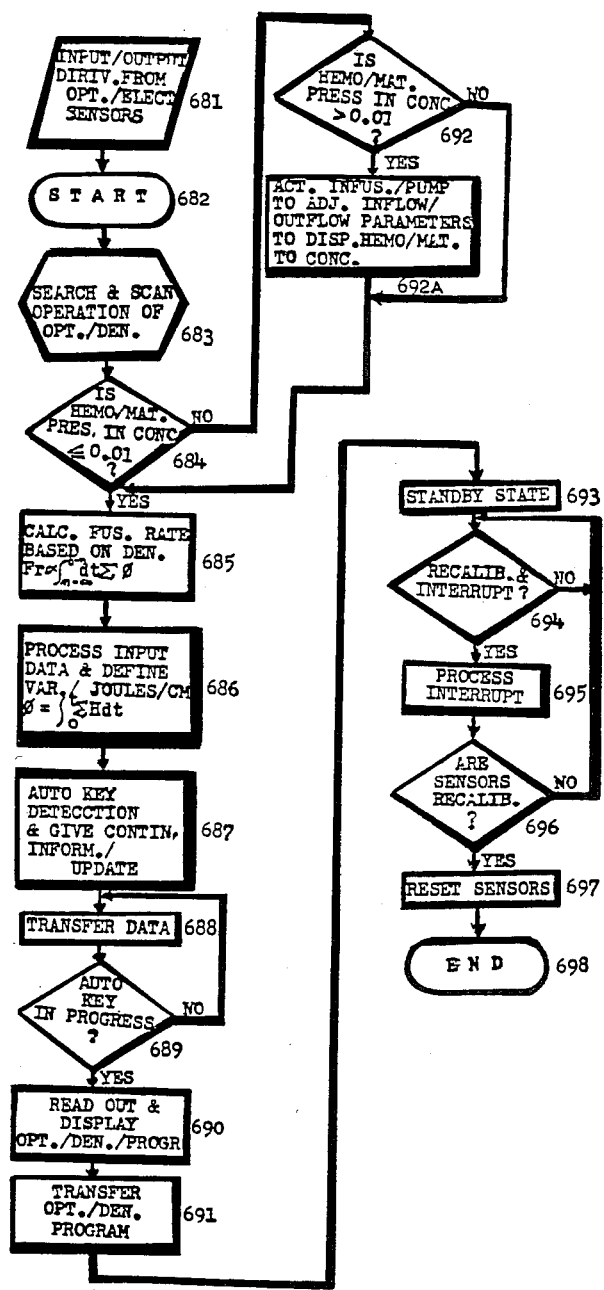
FIG. 26 is a flow diagram calling for a program which specifically compensates for alterations in the intrinsic viscosity pressure, and the thermal parameters as a result of the departiclization process.

FIG. 26 specifies a flow diagram designed for a program which monitors the presence of hemopoetic material, which might impede the lasing process. A continuous stream of input/output derived from optical electronic sensors located onboard the catheter complex is denoted by numeral 681. The data received from numeral 681 initiates start sequence 682, which in turn activates numeral 683, a preparatory scan and search operation measuring the optical density. Element 684 denotes a subroutine which establishes whether or not the level of hemopoetic material is less than or equal to 0.01 of a percent per volume, in the lasing corridor. If the hemopoetic concentration exceeds the 0.01 of a percent per volume value then the data is shunted to element 692, which determines if the concentration of hemopoetic material or an unknown opaque material exceeds 0.01 of a percent per volume, then the data is conveyed to numeral 692A. Numeral 692A embodies a subprogram and subroutine which actuates the infusion pump means to adjust inflow/outflow parameters, to displace the hemopoetic material to a null concentration level, irregardless of the temperature pressure and flow parameters, equal to the ambient condition. If the output from 692 elicits a negative response, then it and that of 692A are both channeled along a common route to the program sequence entering at the level of numeral 685. Numeral 685 calculates the fusion rate Fr, such that $$Fr\alpha \int_{n-\infty}^{0-n} dt\, \phi$$

Number 686 processes input data and defines variables in joules/CM evaluating $\phi$, such that $$\phi = \int_0^t \Sigma H\, dt.$$

The cumulative data from numbers 685 and 686 are feed directly into numeral 687, wherein auto key detection and continuous information is updated. The data from numeral 687 is transferred to 689 via numeral 688. An additional auto key program is actuated as prescribed by element 689, in order to activate a readout and display of the optimum density program, as denoted by numeral 690. The optical density program is transferred to an appropriate prescribed designation. The entire system is put in a standby state, as denoted by number 693. Recalibration and a process interrupt occurs in element 694 and number 695. Element 696 determines whether or not sensors are recalibrated. However, if recalibration occurs then the data is conveyed to numeral 697, or reconveyed to element 694, until recalibration can be instituted. The sensors are reset by number 697, at which point the program is terminated, as described by numeral 698. A more exacting description fusion rate of hemopoetic constitute can be described in accordance with the invention and is set forth herein below;

Seach for cellular, hemopoetic or metabolic constituents if positive identification then calculate fusion rate Fr $$Fr\alpha \int_{n-\infty}^{0-n} dt\, \phi$$

dt = interval of laser exposure
$\Sigma\phi$ = the total emission output in joules for interval dt $$\phi = \int_0^t H dt$$

whereby $\phi$ represents the energy impacting per unit area in joules/cm
Once the calculation is completed transfer data and return to search procedure.

Figure 27:
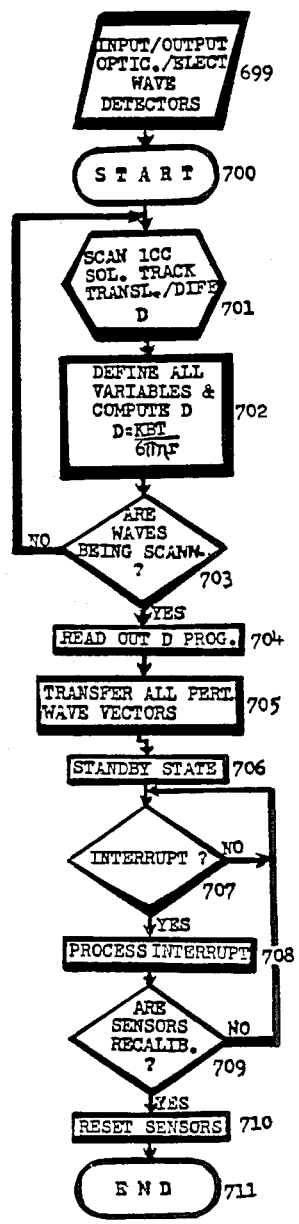
FIG. 27 entails a flow diagram for a program which determines the translational diffusion.

FIG. 27 entails a flow diagram which actuates a program wherein the translational diffusions of specific chemical species can be exacted. Numeral 699 denotes the input/output data previously derived from an array of optical electronic sensors, which are keyed specifically for wave detection. The sensory data of numeral 699 actuates the start sequence, which is denoted by numeral 700. The start sequence enlists a scanning procedure, which repetitively tracks the translational diffusion, D, of chemical species in a volume of one cubic centimeter at a time as prescribed by number 701. The data output conveyed from number 701 is intercepted by numeral 702, wherein all D values are computed based on variations in the Einstein Stoke Equation $$D = KBt/6\pi\eta r$$

Relative mass and composition of the target site is defined in part by the translational diffusion D $$D = KBT/6\pi\eta r$$

KB = Boltsmanns constant
r = radius of a given scatter
$\eta$ = the absolute viscosity of ambients
T = the absolute temperature
$\pi$ = 22/7

All wave data undergoes analysis by a multichannel analyzer means, wherein numeral 702 cycles its data to the analyzer means, which then reconveys the processed data to an element of number 702. All waves are scanned simultaneously and each must be verified by element 703. If the data is verifiable the data from element 703 is conveyed to numeral 704, if not the data is recycled back to operative process 701 for further scanning. Numeral 704 specifies that the D readout program be actuated. Numeral 705 denotes a subroutine which transfers all pertinent wave vectors to their appropriate designated operative sites. While the data is undergoing transferral the entire system is placed in a standby state, as indicated by numeral 706. Numeral 706 is followed by an interrupt and process interrupt sequence, as denoted by numerals 707 and 708. Once the process interrupt has been completed the sensors are recalibrated and verified by element 709. If recalibration of sensors is unverifiable, then the data is sent back to the main program sequence. However, if the sensors are recalibrated, then the data from element 709 is sent to numeral 710, wherein all sensors are reset prior to program termination which is indicated by numeral 711.

Figure 28:
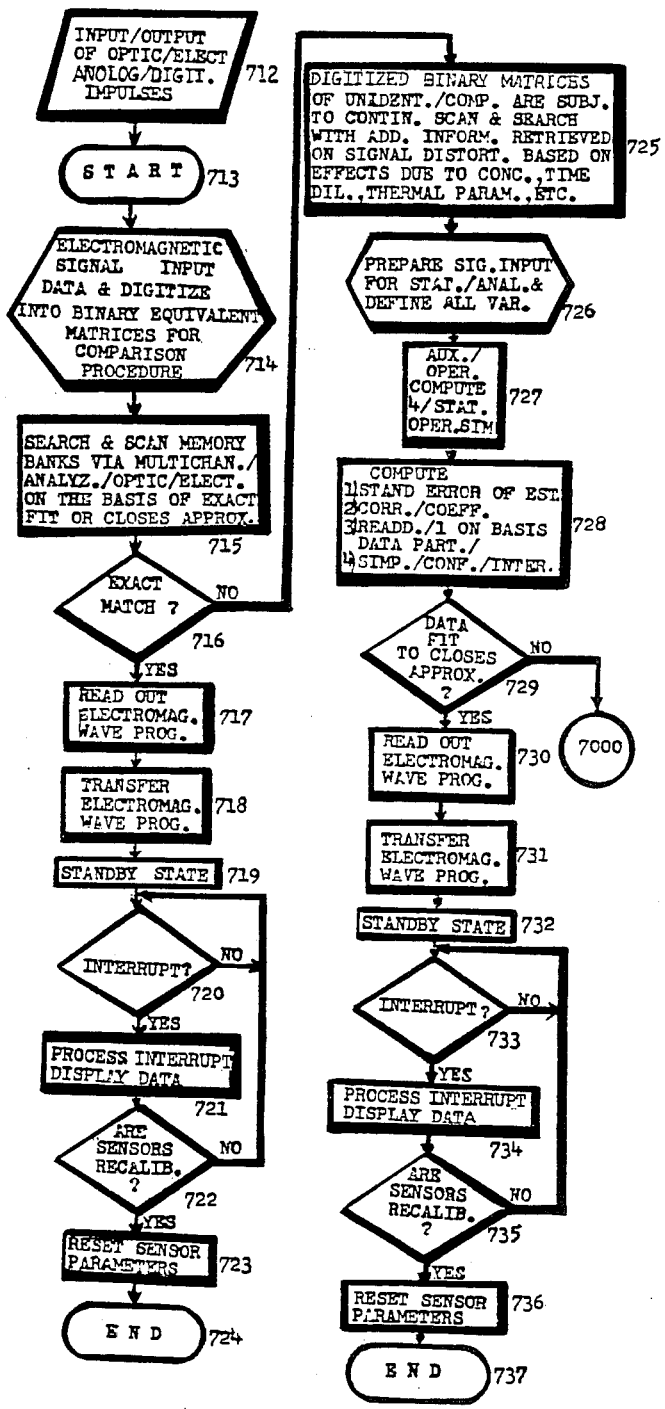
FIGS. 28 through 30 are flow diagrams exacting a statistical program which matches and identifies incoming optical electronic data.
Figure 29:
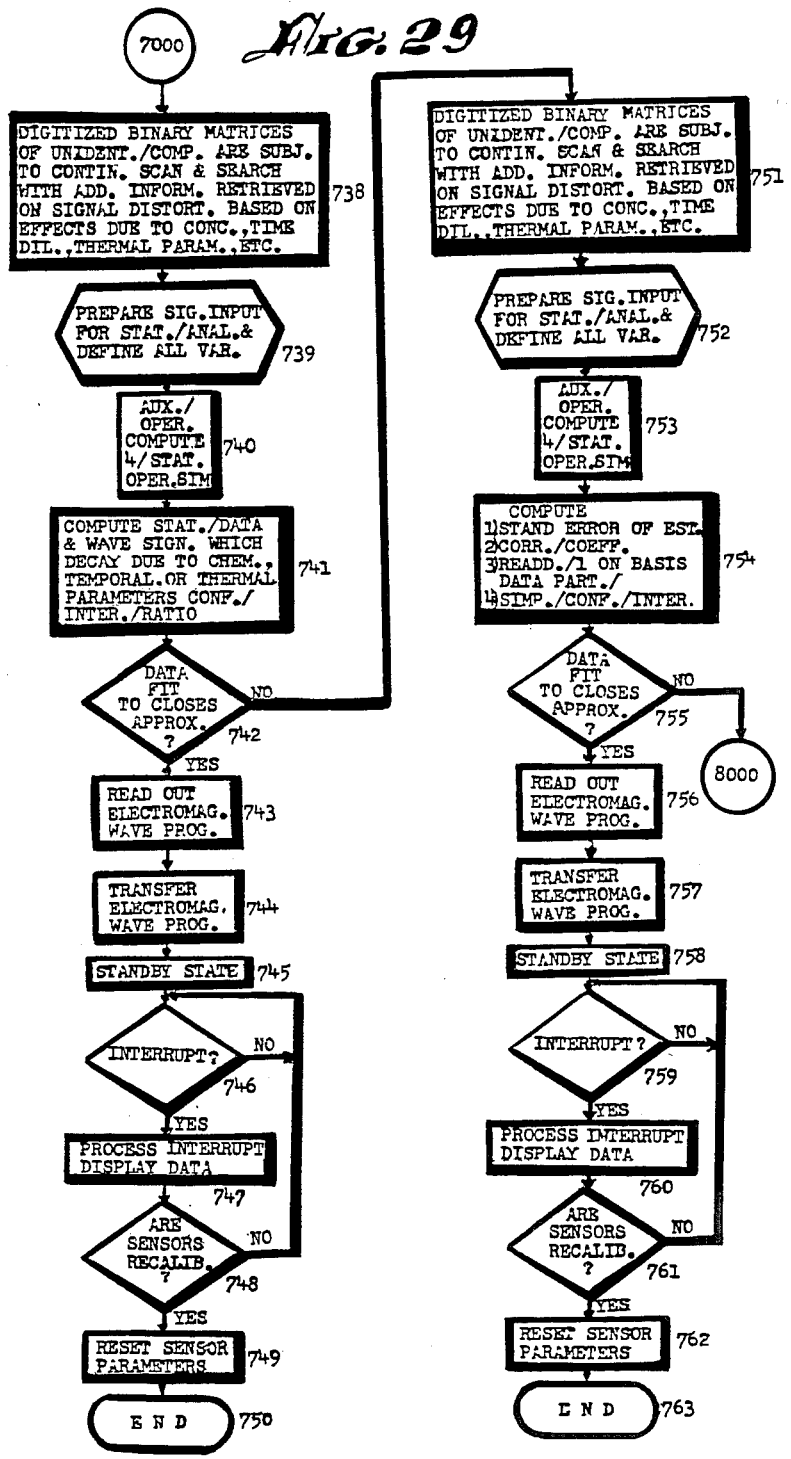
Figure 30:
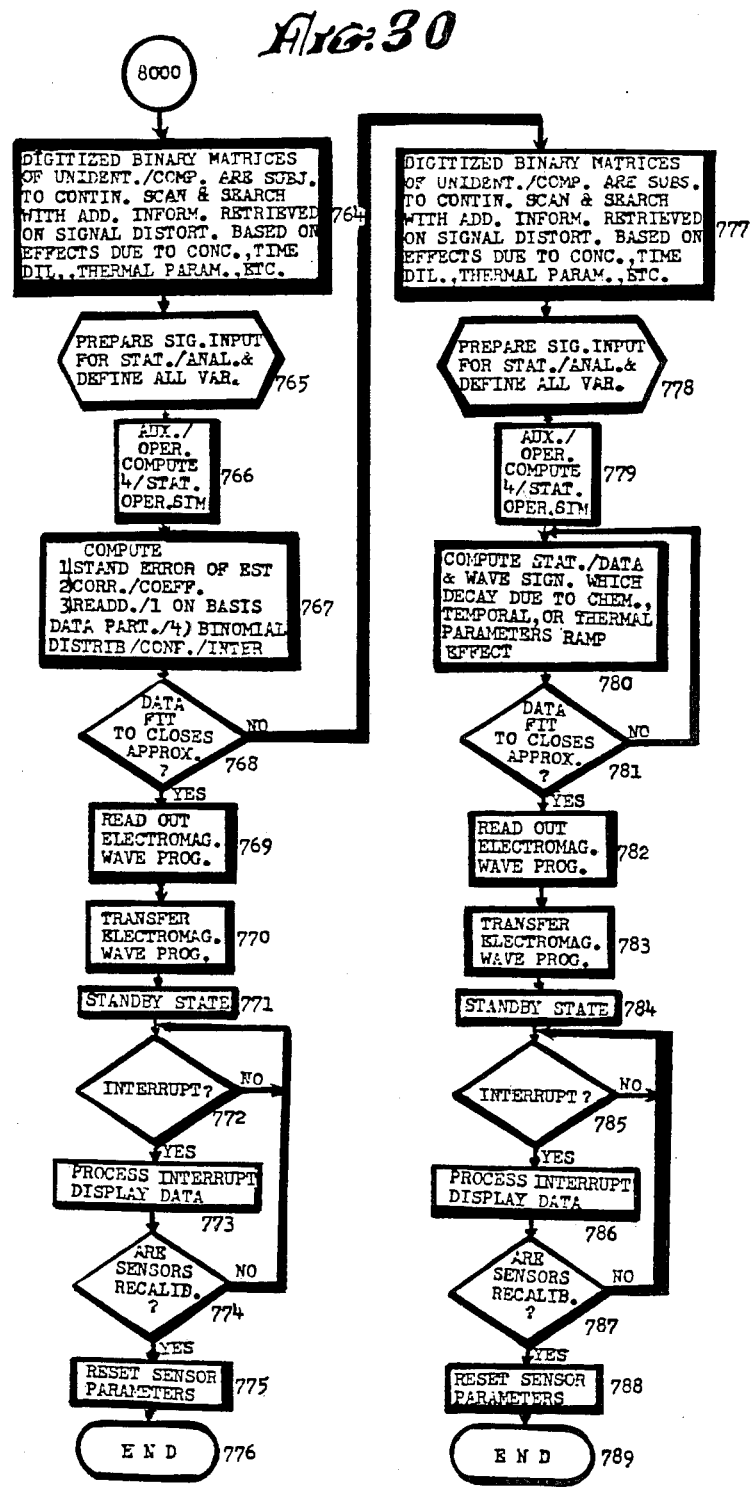

FIGS. 28 through 30 are flow diagrams exacting a program which identifies and matches all incoming optical electronic data and the like obtained from the sensors. The computational procedures consist of a series of repetitive statistical processes. Optical electronic analog impulses designated by number 712 actuates the start sequence 713. Number 714 is a preparatory operation, wherein electromagnetic signals input data and are digitized and converted into their binary equivalent matrices for a specified comparison procedure. The data which is channeled from numeral 714 enters number 715, wherein a search and scan indexing procedure that matches data exclusively on the basis of an exact fit or closest approximation of those values, which are already listed and readily assessable from the memory banks of the analyzer means. If an exact match can be ascertained then the data is channeled to number 716, and if an exact match can not be verified, then the data is shunted to numeral 725. The electromagnetic wave program is read out as indicated by numeral 717. The data from numeral 717 is transferred to a designated operative mode by number 718. While the actual transferral of data is in progress the statistical program is put in a standby state, as numeral 719 indicates and a predetermined interrupt step is elicited, as described by element 720, until a process interrupt and data display can be properly effected as prescribed by number 721. Once the data has been displayed by number 721 then the sensors undergo recalibration, which is verified by element 722. If verification by element 722 is immediate, then all sensor parameters are reset as denoted by numeral 723, which occurs prior to the programs termination as indicated by numeral 724. If the data is not verifiable then it is merely shunted back to the main program sequence, where the data is cycled once again. As described earlier in the above herein disclosure if an exact match from element 716 is unavailable, then the data from 725 is shunted to numeral 725 for further processing. Numeral 725 is a computerized statistical process, whereby digitized binary matrices of unidentified compounds are subjected to a continuous scanning and search procedure; and are inacted with several supplemental subroutines correcting for signal distortions due to variations in concentration of a specified chemical species, the effects of temporal dilation, the effects of thermal convective parameters, and the like. The output data exiting numeral 725 is conveyed to number 726, which is a preparatory operation, whereby signal input undergoes statistical inference and all variables are defined. The data conveyed from number 226 enters numeral 227 an auxiliary operative element, which commands the main computer to compute four different statistical operations simultaneously. The four different statistical operations are defined by number 728, and consist of the statistical error of estimate, the correlation coefficient, readdressible operations such as linear regression, standard error of estimate or like operations, and the computation of a simple confidence interval. The data is conveyed from number 728 to element 729, where it is determined whether or not the data input fits to the closest approximation of those values estimated or otherwise contained within the accumulative memory of the main computer complex. If however, the data from element 729 can not be determined on the statistical format listed in the preceding, then the data is channeled into a new, but equivalent statistical format. The data from element 729 of FIG. 28 is conveyed to numeral 738 of FIG. 29, as described by numeral 7000. Once it has been established that the data received from various sensors can be categorized, then the electromagnetic wave program is read by number 730 and transferred by numeral 731 to one more designated locations, such as a display terminal or the memory of the main computer complex. While the transferal data is occurring the entire statistical format is put in a standby state, denoted by number 732, which is followed by an interrupt due to the time lag and a process interrupt as data is displayed and made available to the user, numbers 733 and 734. The sensors are recalibrated automatically after being displayed as indicated by numeral 735. After recalibration of sensors are completed, then the sensory parameters are reset, which is denoted by number 736, prior to terminating the statistical operations of the program, as indicated by numeral 737.

FIG. 30 is a continuation in part of the statistical program proposed by flow diagrams depicted in FIG. 29. Numerals 738 through 750 and numerals 751 through 763 of FIG. 29 are equivalent to numbers 725 through 737 of FIG. 28 inclusive. The statistical procedures disclosed herein above concerning FIGS. 28 and 29 are equivalent with two important exceptions. The first exception as denoted by numeral 741 of FIG. 29 computes statistical data and wave sign, which computes alterations in wave functions on the basis of signal decay due to chemical lability, due to temporal instability or thermal degradation, via variations of confidence intervals having exponential parameters. The second exception is that element 755 transfers the data from FIG. 29 to numeral 764 of FIG. 30, as indicated by numeral 8000. FIG. 30 differs from FIGS. 28 and 29 in two aspects. Numbers 764 through 776 and numeral 777 through 789 are equivalent to those of the preceding FIGS. 28 and 29 with the exception of numbers 767 and 780 respectively. Component statistical program four of numeral 767 provides for a binomial distribution confidence level, which denotes one exception to the rule. The second exception of FIG. 30 lies in the numeral 780, wherein the computed statistical data is computed on the basis of the ramp effect. It is the accumulative effect of the statistical subprogram and subroutines which allow the data to be categorized and identified on the basis of a cumulative method described herein, as the best fit method. Variations of the following well known annexed statistical formulas manipulates data in accordance with the specific objectives set forth in the invention herein below;

Data Best Fit Method For Known Wavelengths And The Like

1. Linear Regression for a regression of y on x $$E(y/x) = B_o + B_1 x_1$$

where $E(y/x)$ is $\overline{X}$ of distribution y for a given x
Standard Error of Estimate $$S_x = \sqrt{\frac{E[y_i - (b_o + b_1 x_i)]^2}{n-2}}$$

where $$b_1 = \frac{\Sigma m\, x_i y_i - (\Sigma x_i)(\Sigma y_i)}{n \Sigma x^2 i - (\Sigma x_i)^2}$$

$$b_o = \frac{\Sigma y_i}{n} - b_1 \frac{\Sigma x_i}{n}$$

$$= Y - b_1 X$$

2. Correlation

An estimate of a given population of readings correlation coefficient p is given by $$r = \frac{\Sigma(x_i - \overline{X})(y_i - \overline{Y})}{\sqrt{[\Sigma(x_i - X)^2][\Sigma(y_i\, Y)^2]}}$$

$$r = \frac{n \Sigma x_i y_i - (\Sigma x_i)(\Sigma y_i)}{\sqrt{[n \Sigma x_i^2 - (\Sigma x_i)^2][n \Sigma y_i^2 - (\Sigma y_i)]^2}}$$

For grouped data $$r = \frac{n \Sigma f x_i y_i - (\Sigma f x\, X_i)(\Sigma f y Y_i)}{\sqrt{[n \Sigma f x\, X_i^2 - (\Sigma f x\, X_i)^2][n \Sigma f y\, Y_i^2 - (\Sigma f_y\, Y_i)^2]}}$$

where fx and fy denote the frequencies corresponding to the class marks x and y and f denotes the frequency of the corresponding cell of the correlation.

If the data is coded $$r = \frac{n\Sigma fuv - (\Sigma fu\, U)(\Sigma fv\, V)}{\sqrt{[n\Sigma fu\, U^2 - (\Sigma fu\, U)^2][n\Sigma fv\, V^2 - (\Sigma fv\, V)^2]}}$$

where u's and v's denote coded class marks and frequencies fu=fx and fu=fy

3. Check Standard Error of Estimate $$Sy \cdot x = \sqrt{\frac{\sum_{i=1}^{N}(Yi - \overline{Yi})^2}{N}}$$

then partition total variance into predictable and error portions of wave form $$\frac{\sum_{j=1}^{J}\sum_{i=1}^{nj}(Yji - \overline{Y})^2}{\sum_{j=1}^{J} nj} = \frac{\sum_{j=1}^{J}\sum_{i=1}^{nj}(Yj - Y)^2}{\sum_{j=1}^{J} nj} + \frac{\Sigma\Sigma Yji - Yj)^2}{\sum_{j=1}^{J} nj}$$

4. Compute Confidence interval for a series of wavelength variance $$\frac{(N-1)Sx^2}{X^2\, 0.95} < \sigma x^2 < \frac{(N-1)\hat{S}x^2}{X^2\, 0.05}$$

where $$\hat{S}x = \frac{Sx}{\sqrt{N-1}}$$

$$\hat{S}x^2 = \frac{N}{(N-1)} Sx^2$$

$$X^2 = \frac{(N-1)\hat{S}x^2}{\sigma x^2}$$

$$\sigma x^2 = \Sigma P(X - \mu)^2 = \frac{\sigma^2}{n}$$

$\sigma^2$=population variances of individual values of X, n=sample size

All data must fall into catagories of 1–4 or else procede to calculate confidence interval for binominal wave proportions Probability $\Phi$, errors occurance $1-\Phi$ X=positive observation mean $n\Phi$ and variance $n\Phi(1-\Phi)$ observed frequency=$Po=xo/n$ $Pr\{\Phi(Po) \leq \Phi \leq \Phi(Po)\} = 1 - \alpha$ upper confidence limit $\Phi$ described as $$\sum_{x=o}^{xo} \binom{n}{x} \overline{\Phi}^x (1 - \overline{\Phi})^{n-x} = \alpha/2$$

lower confidence limit $\Phi$ described as $$\sum_{xo}^{n} \binom{n}{x} \Phi^x (1 - \Phi)^{n-x} = \alpha/2$$

$u = (2 \arcsin \sqrt{p} - 2 \arcsin \sqrt{\Phi}\sqrt{\eta})$ $p = x/n\overline{X} = \Phi$ variance $= \Phi(1-\Phi)/n$ unless adjustments are made for a confidence interval for $2 \arcsin \sqrt{\Phi}$ is $$Pr\left\{\left[2 \arcsin \sqrt{p} + \frac{u - \alpha/2}{\sqrt{n}}\right] < \arcsin \sqrt{\Phi} < \left[2 \arcsin \sqrt{p} + \frac{u\alpha/2}{\sqrt{n}}\right]\right\} = 1 - \alpha$$

half width of confidence interval $\Phi$ is $$\delta^* = \tfrac{1}{2} E\left\{\sin^2\left[\arcsin \sqrt{p} + \frac{U\alpha/2}{2\sqrt{n}}\right] - \sin^2\left[\arcsin \sqrt{p} + \frac{U - \alpha/2}{n}\right]\right\}$$

$U - \alpha/2 = -U\alpha/2$ in symetrical distribution to obtain a confidence interval with expected width $=2\delta^*$ at a probability level of $1-\alpha$ with a real but unknown $\Phi$ the required sample size of data must be $$n \simeq \left[\frac{U\alpha/2}{\arcsin\left(\frac{\delta^*}{\sqrt{p}\cos(\arcsin \sqrt{p})}\right)}\right]$$

where $U\alpha/2$ is lower limit of cumulative standard normal probability integral if $\Phi$ is undiscernable then $$n\, \max \simeq \left(\frac{U\alpha/2}{\arcsin 2\, \delta^2}\right)^2$$

confidence interval for wave signals, which decay or which have exponential parameters Chi Square distribution with 2r degrees of freedom $$2\left[\sum_{i=1}^{r} ti + (n - r)\, tr\right]$$

let T equal the total time
$\theta = \overline{X}$ and variable t is expoentially distributed with $\theta$ then $$T = \sum_{i=1}^{r} t_1 + (n - r)\, tr$$

then the two sided confidence interval Ramp Effect for the expoential scale parameter is described by $$Pr\left\{ \frac{2T}{X^2\alpha/2} < \theta < \frac{2T}{X_1^2 - \alpha/2} \right\} = 1 - \alpha$$

maximum % deviation of $\theta$ from the midpoint of the confidence interval will be described as $$r^* = 1 - \frac{2T}{\theta'C} = \frac{2T}{\theta'D} - 1$$

where $C=X^2\alpha/2$, $D+X^2-\alpha/2\theta$ is the midpoint of confidence interval, $r^*$=midpoint interval at a probability level $1-\alpha$ $$\frac{C-D}{C+D} = r^*$$

ordered observation $=r, f=2r$
if $f>30$, $r>15$, then an accurate approximation of $f$ can be obtained by assuming $\sqrt{2x^2}$ as a normal distribution with mean $\sqrt{2f-1}$ and variance unit, such that when $r^*$ is given $$f \simeq \tfrac{1}{2} + U\alpha/2 \left[ \frac{1}{r^*} \left( \frac{1}{r^*} + \sqrt{\frac{1}{r^{*2}} - 1} \right) - \tfrac{1}{2} \right]$$

and $r \simeq \tfrac{1}{4} + \dfrac{U\alpha/2}{2} \left[ \dfrac{1}{r^*} \left( \dfrac{1}{r^*} + \sqrt{\dfrac{1}{r^{*2}} - 1} \right) - \tfrac{1}{2} \right]$ when $U\alpha/2$ is the lower limit of the cumulative standard normal probability integral
confidence interval for the ratio of two expoential parameters wavelength decay/electric field mobility
let $V_1$, $V_2$ have independent Chi Square distribution with $f_1$ and $f_2$ degrees of freedom,
then ratio $V_1 f_1^{-1}/V_2 f_2^{-1}$ with $f_1/f_2$ as a Fishers F distribution such that $$2r_2 \left[ \sum_{i=1}^{r} t_1i + (n_1 - r_1)t_1r_1 \right] / 2r_1 \left[ \sum_{j=1}^{r_2} t_2j + (n_2 - r_2)t_2r_2 \right]$$

$\theta_1/\theta_2$ is a multiple of Fishers F distribution with $f_1=2r_1$ degrees of freedom and $f_2=2r_2$ degrees of freedom, such that $f_1/f_2$ if $t_1$ and $t_2$ are expoentially distributed with means $\theta$ and $\theta$, and $$T_1 = \sum_{i=1}^{r} t_1i + (n_1 - r_1)t_1r_1$$

$$T_2 = \sum_{j=1}^{r} t_2j + (n_1 - r_2)t_2r_2$$

then the ratio of the two exponential scale parameters are denoted by $$Pr\left\{ \frac{r_2 T_1}{r_1 T_2} \frac{1}{F\alpha/2} \frac{\theta_1}{\theta_2} < \frac{r_2 T_1}{r_1 T_2} \frac{1}{F - \alpha/2} \right\} 1 - \alpha$$

midpoint confidence interval $$r^* = 1 - \frac{r_2 T_1}{r_1 T_2 C} \lambda'^2 = \frac{r_2 T_1}{r_1 T_2 D} \lambda'^2 - 1$$

where $C=F\alpha/2$, $D=F-60/2$ and $\lambda'^2$ is the midpoint of the confidence interval maximum deviation of the variance ratio from midpoint$=r^*$ at $1-\alpha$ probability level so that $$\frac{C-D}{C+D} = r^*$$

Figure 31:
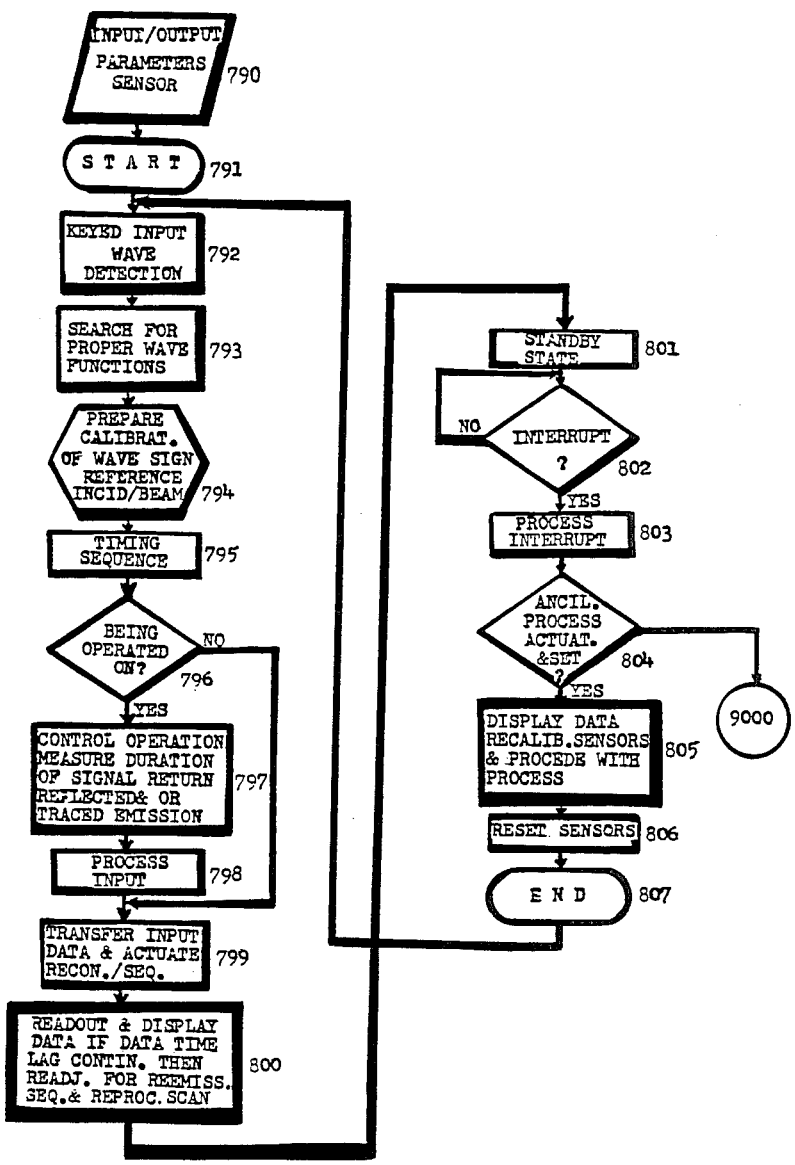
FIG. 31 is a flow diagram exacting a program for continuous wave calibration.

The shortest confidence interval for a given aggregate number of degrees of freedom where $f_1=f_2$ is $$f_1 = f_2 \simeq 16 \left[ \frac{U\alpha/2}{\ln\left(\frac{1+r^*}{1-r^*}\right)} \right]^2$$

and $$r_1 = r_2 \simeq 8 \left[ \frac{U\alpha/2}{\ln\left(\frac{1+r^*}{1-r^*}\right)} \right]^2$$

where $U\alpha/2$ is the lower limit of the cumlative standard probability integral FIG. 31 is a flow diagram exacting a program for continuous wave calibration for one or more specified emission sources. Numeral 790 denotes the input/output sensory parameters which actuate the main start sequence 791. The activation of start sequence numeral 791 actuates an auto keyed input wave detection means defined by number 792. The data from number 792 initiates number 793, which provides a means wherein a search for the proper wave functions are exacted. The output signal conveyed from number 793 is intercepted by numeral 794. Numeral 794 is a preparatory operation, whereby calibration of wave signals for both the incident and reference beams occur simultaneously, as each is differenced against the other. A specified timing sequence is enlisted by numeral 795. Element 796 determines if the wave differencing is being adequatly operated on or not. If a positive response is elicited by element 796 then the data is conveyed to number 797, and if a negative response is elicited, then the data is channeled from element 796 to numeral 799. Numeral 797 designates a control operation wherein the duration of a signal return is measured, whether it is reflected by a target or reemitted by the said target. The input derived from numeral 797 is processed by number 798, and the transferal of the data input occurs in numeral 799. As the transferal of data progresses it automatically triggers a recognition sequence. The data received from numeral 799 is readout and displayed by numeral 800, which readjusts its values to compensate for a time lag continuation due to prolonged reemission sequence, while the data is being processed, reevaluated and readjusted by numeral 800. Then the entire program is put in a standby state as indicated by number 801. the standby state number 801 is immediately interrupted, as described by element 802, and set in a process interrupt mode, as prescribed by number 803. The data exiting number 803 enters element 804, where it is established whether or not certain coded ancillary processes are actuated and set. If a negative response is elicited by element 804, then the data is shunted from element 804 of FIG. 31 to numeral 808 of FIG. 32, as indicated by numeral 9000. If a positive response is elicited by element 804, then the data is conveyed to numeral 805, whereby the data is displayed and the sensors are recalibrated, so that the ongoing process can procede. The sensors are reset by number 806, prior to the programs termination, which is denoted by number 807.

Figure 32:
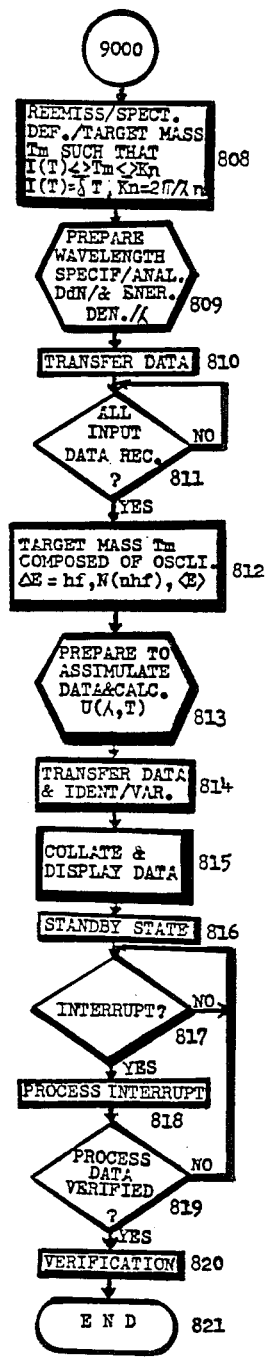
FIG. 32 is a flow diagram for re-emission which specifies a program analyzing the spectra for a given target mass.

FIG. 32 is a flow diagram specifing a program for analyzing the spectra reemission of given target loci, which undergoes high energy laser bombardment. FIG. 32 is a continuation in part of FIG. 31, since a negative response from element 804 of FIG. 31 channels data output to numeral 808 of FIG. 32 as previously noted. Numeral 808 defines target mass Tm reemission spectra for all T (T) values. The wave specification derived by numeral 808 is conveyed to numeral 809, wherein a preparatory operation is enlisted to deduce wavelength specifications, analysis of DdN values, to define energy parameters and define the overall density of Tm per wavelength. Transferal of data from numberal 809 to element 811 is conducted by number 810. Element 811 establishes whether or not all input data is received; and if a negative response is elicited, then the data is recycled from element 811 back to itself and is added to the data, which is transferred from numeral 810. Occassionally data is recycled by an element back to itself, when confirmation can not be exacted due to a weak data signal. The data from element 811 is transmitted to numeral 812, when confirmation is exacted. Numeral 812 is a process wherein target mass Tm is assessed based on the fact that it is composed of oscillators defined by $<E>N(nhf)$, such that $\Delta E=hfj$. Number 813 is a preparatory process utilized to assimilate data and calculate all values of $U(\lambda,T)$. The data from number 813, once being operated on is then conveyed to numeral 814, whereby the data is transferred and the variables are identified in a prescribed manner. The data from numeral 814 is transferred to numeral 815, where the data is collated and displayed for the user. A certain specified time must elapse before the data to be collated and displayed. The system must also have time to recover and clear some of its circuits. The entire program is put in a standby state, as noted by number 816 and a interrupt/process interrupt is effected, as described by numerals 817 and 818; all of which allows for a finite recovery period for the system. Element 819 establishes whether or not the process data is verified. If a negative response is elicited by element 819, then the data is recycled back to be reentered into element 817. However, if the data confirmation occurs, then the data is sent to numeral 820. It is in numeral 820, wherein all values undergo verification. Once verification has taken place the program is abruptly terminated as indicated by numeral 821.

The mathematical equations depicting reemission and or reflection of an emission source are well established and are employed in accordance with the invention set forth herein below; reemission spectrum total intensity radiated by ideal black body is expressed as:

$$I(T) = \int_0^\infty I(\lambda,T)d\lambda$$

$$I(T) = \sigma T^4$$

where T is absolute temperature and $\sigma = 5.67 \times 10^{-8} W/m^2 K^4$ $$I(\lambda,T) = \frac{a_1 e^{-a_2/\lambda T}}{\lambda^5}$$

assuming an ideal perfectly reflecting surface area generalized the resultant value to three dimensions with the allowed modes corresponding to wave numbers given by $$Kn = \frac{\pi}{L}(n^2x + n^2y + n^2z)^{\frac{1}{2}} = \frac{2\pi}{\lambda n}$$

where $n = (n^2x + n^2y + n^2z)^{\frac{1}{2}}$
modes following within concentric spheres of radius n and n+dn of target area is described as:

$$dN(\tfrac{1}{8})4\pi n dn$$

radius in soft lattice configuration $$n = \frac{2L}{\lambda n}$$

and is differentiated with respect to a specified wavelength $$dn = \frac{2L}{\lambda^2 n} d\lambda n$$

then $$dN = (\tfrac{1}{8})4\pi \frac{(2L)^3}{\lambda^4 n} d\lambda n \quad (2)$$

$$\frac{1}{L^3} \frac{dN}{d\lambda n} = \frac{8\pi}{\lambda^4 n}$$

$$\frac{\text{energy density}}{\text{wavelength}} \rightarrow U(\lambda,T) \frac{8\pi}{\lambda^4 KT}$$

Each oscillator has a discrete energy state as denoted by $$En = nhf$$

h is found fitting results with experimental data i.e. best fit method*

$$\Delta E = hf$$

large numbers of thermally excited oscillators are distributed among the allowed energy levels described by $$N(nhf) = Noe^{-nhf/KT}$$

The average energy of oscillators distributed over quantum states is listed a series of expressions such as:

$$<E> = \frac{\sum_{n=o}^{\infty} N(nhf)En}{\sum_{n=o}^{\infty} N(nhf)} = \frac{\sum_{n=o}^{\infty} Noe^{-nhf/KT} nhf}{\sum_{n=o}^{\infty} Noe^{-nhf/KT}} =$$

$$\frac{hfx(1 + 2x + 3x^2 + \ldots)}{(1 + x + x^2 + \ldots)}$$

where $x = e^{-hf/KT}$ yielding $$<E> \; hfe^{-hf/KT} \frac{(1-x)^{-2}}{(1-x)^{-1}} = \frac{hf}{e^{hf/KT} - 1}$$

for $$\frac{\text{density modes}}{\text{wavelengths}}$$

depicted by the expression $$U(\lambda, T) = \frac{8\pi hc}{\lambda^5} (e^{hc/KT} - 1)^{-1}$$

Figure 33:
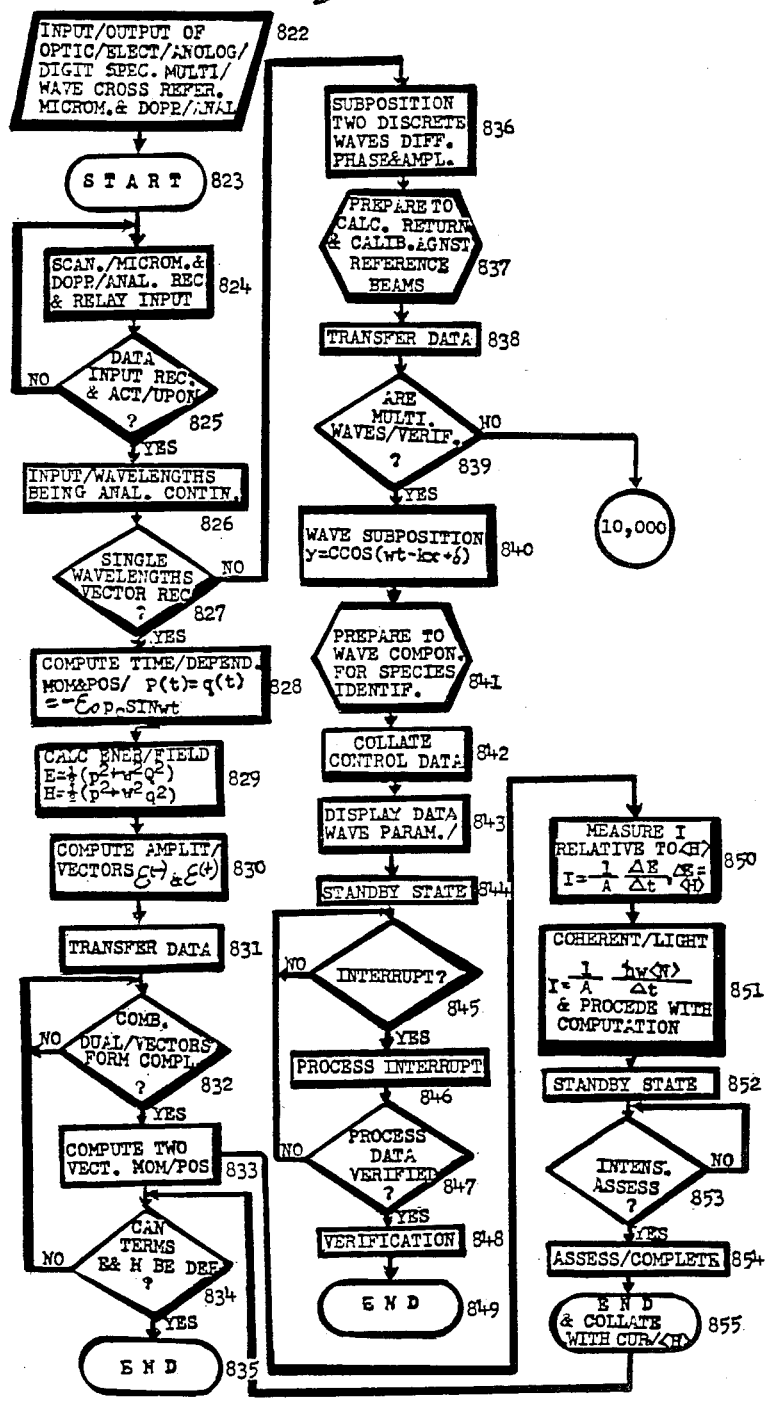
FIGS. 33 and 34 are flow diagrams exacting a detailed program for wavelength doppler analysis.
Figure 34:
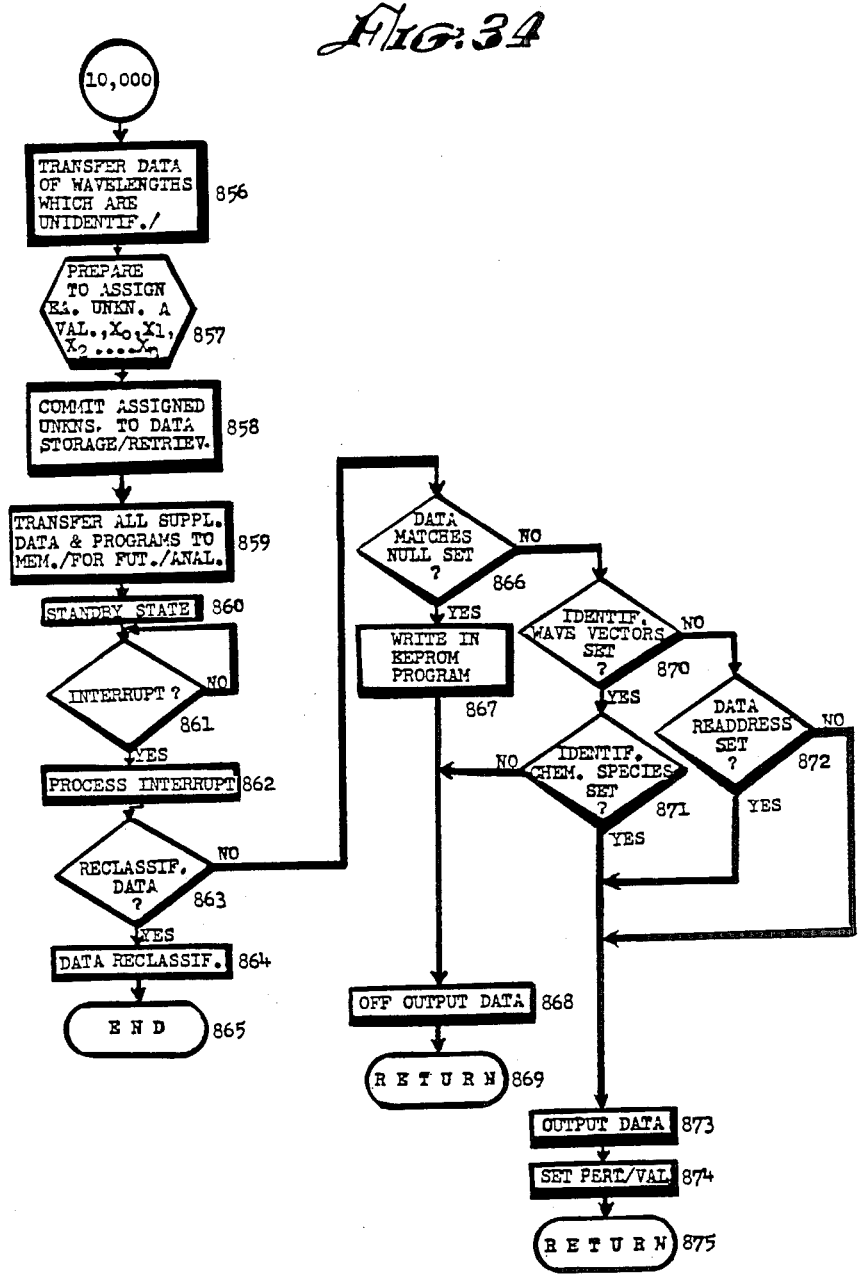

FIGS. 33 and 34 are flow diagrams exacting a detailed program specifying doppler analysis. Numeral 822 contains analog/digital input/output optical electronic data which has been processed by such analytical means as a multichannel analyzer, microdensometer, light beating spectrometer, and similar such means. The digitized wave signals derived by numeral 822 actuate the start sequence denoted by numeral 823. The output signal sent from numeral 823 auto keyed a sequencer number 824, which activates an automated scanning micrometer multichannel analyzer complex, whereby data is simultaneously exchanged between all operative systems. Element 825 verifies whether data recognition has occurred, and whether or not the information can be acted upon by the data processing system. The high density or compact optical electronic input wavelengths are under continuous analysis, as determined by number 826. All signals wavelengths are identified by virture of specific wave functions, and each and every wavelength vector must be recognized. The recognition sequence is verified by element 827, whereby the data is conveyed to number 829 upon confirmation, or if a negative response is elicited the data from element 827 is channeled to number 836. After wavelength recognition is established the time dependent momentum and position are computed on the basis of $p(t) = q(t) = -\epsilon_o po \sin wt$, which is indicated by number 828. The energy field specification is denoted by numeral 829 and is described on the basis of two equations $$H = \tfrac{1}{2}(p^2 + w^2 Q^2), \; H = \tfrac{1}{2}(p^2 + w^2 q^2)$$

amplitude vectors are computed $\epsilon(-)$, $\epsilon(t)$ on the basis of wave gating, in numeral 830. The data from numeral 830 is transferred to element 832 via mode number 831. Element 832 combines duel wave vectors forming a complexed multiphasic wavelength. If data is not capable of being combined, then the data is reconveyed back to element 832 by superimposing the signal on the signal which is generated by number 831. This provides the necessary clearification needed for signal verification and coupling. Numeral 833 computes two vectors of momentum and position computed as closely together as possible, remembering that the continuous data input is repetitive and equivalent. Element 834 assess whether or not components E and H can be defined, and if the components are identified the program is effectively terminated as designated by number 835. The data is reconveyed from element 834 back to element 832 if a negative response is elicited by element 834. As noted earlier if a single progression of wavelength vectors is unrecognizable, then the data is shunted to numeral 836. Numeral 836 provides a tactical strategy which identifies a subposition of two discrete waves, within a real time frame differing in both phase and amplitude from one another. The data from numeral 836 is channeled to numeral 837, wherein complexed data waves enter a preparatory operation. Each wave component of the return emission is calculated and calibrated against its respective reference beam so that differencing can occur. The data from number 837 is conveyed to element 839, via transfer, as denoted by numeral 838. Element 839 specifically determines whether multiple waves are present. If multiple waves are present and identifiable, then the data is transferred to numeral 840. If however, the data is unidentified, then the data is shunted from element 839 to numeral 856. Once the data is infact verified then calculations are made by numeral 840 on the basis of wave subposition, such that several variations of subposition are calculated, one of which is exprressed by the equation $y = \cos(wt - kx + \delta)$. The data from numeral 840 is upon specification sent to numeral 841, wherein a preparatory operational mode readies each deciphered wave component, which is classified or indexed against known wave parameters, and each altered wave characteristic corresponds to a specific identifiable chemical species. The data derived from numeral 841 is collated with control data, as noted by number 842, and it is displayed for the user as described by number 843. During the display period the entire system is put in a standby state, as indicated by number 844, and an interrupt verification and process interrupt numbers 845, 846 procede the process data verification designate element 847. Once verification is established the program is terminated and made ready for the next phase of the operation, as is described by numbers 848 and 849. The data from numeral 833 as indicated in FIG. 33 is divergent, such that the same information leaving number 833 is conveyed to numeral 850, as well as element 834. Numeral 850 measures I relative to $<H>$, such that $$I = \frac{1}{A} \frac{\Delta E}{\Delta t} \; \Delta E = <H>.$$

Coherent light is further processed on the basis of $$I = \frac{1}{A} \hbar w \frac{<N>}{\Delta t}$$

as indicated by numeral 851. Number 852 is a standby phase and element 853 assesses intensity of the light beating spectrum. Once the assessment process is completed as noted by numeral 854, then the entire program is terminated as indicated by element 855, wherein the data of the termination signal is collated with all current $<H>$, and this information re-enters the main program sequence at the level of element 834. Information from element 839 of FIG. 33 enters element 856 of FIG. 34 as warrented. The continuity between FIGS. 33 and 34 is denoted by numeral 10,000. Numeral 856 transfers data of wavelengths which are otherwise unidentifiable. The data is then placed in a preparatory mode number 857, which assigns each unknown a designated value or label, such as the binary equivalent of $X_0, X_1, X_2, \ldots X_n$, so that glitches do not develop in the program. The unknowns are all listed and committed to memory to be retrieved later for further analysis, as described by numeral 858. Numeral 859 is indicative of a transferal process, which forwards all supplementary data and auxiliary programs to the memory mode of the main computer complex for further analysis, as is prescribed by number 859. As the transferal process occurs a standby state is elicited, number 860, and an interrupt/process interrupt is noted by element 861 and number 862 respectively. Data reclassification is assessed by element 863. A positive response elicited by element 863 allows the data to undergo data reclassification as described by numeral 864, prior to termination of the program as denoted by 865. As described earlier a negative response elicited by element 863 shunts the data to element 866, wherein it is determined whether or not the data matches a null set, that is if the data vector is orthogonal with all known waves, or are defined mathematically as a singularity. If a singularity is established, then a separate program must be auto keyed by the main computer complex via an EEPROM module, as indicated by number 867. Off line output data is supplied as indicated by number 868, in order to supplement the output data derived from number 867. The combined data output sent from number 868 is returned to the main computer complex as noted by number 869, wherein the data undergoes further analysis to determine whether some unknown element initially causes the singularity condition; or if differences are caused by thermal kinetic parameters, or chemical instability not accounted for in the original computer program. If a negative response is elicited by element 866, then the data is shunted to element 870, where it is determined whether or not wave vectors which are identified can be set. If the data identification and wave vectors can not be set, then the output data from element 870 is shunted to element 872. Element 872 confirms whether or not the data readdress is set, and irregardless of the response elicited the data is conveyed to number 873. The data from element 870 is conveyed to element 871 if confirmation occurs, and it is in element 871 where identification of a given set of chemical species are established either to be set or confirmed. If the unidentified species are set then the data from element 871 is conveyed to numeral 873, which is a data compiler means. The output from 873 is channeled to number 874, which is a process that automatically sets and lists all pertinent values. The listed values are returned to the main computer complex, as denoted by number 875, were further analysis, definitions, and instructions are exacted.

Subposition of two individually distinct single frequency waves traveling in the same direction, in the same absolute time frame, but differing in both their phase and amplitude.

$$y = A \cos(wt - kx + \phi)$$

$$y = y_1 + y_2 = A_i \cos(\theta + \phi_1) + A_2 \cos(\theta + \phi_2)$$

Let $\theta = wt - kx$ and $\cos(\theta \pm \phi) = \cos\theta \cos\phi \pm \sin\theta \sin\phi$
the sum is $$y = (A_1 \cos\phi_1 + A_2 \cos\phi_2) \cos\theta - (A_1 \sin\phi_1 + A_2 \sin\phi_2) \sin\theta$$

if two new constants are specified as $$C \cos\delta = A_1 \cos\phi_1 + A_2 \cos\phi_2$$

and $C \sin\delta = A_1 \sin\phi_1 + A_2 \sin\phi_2$ the super subposition of the two waves becomes $$y = C \cos(wt - kx + \delta)$$

where
$$C^2 = (A_1 \cos\phi_1 + A_2 \cos\phi_2)^2 + (A_1 \sin\phi_1 + A_2 \sin\phi_2)^2$$

and $$\tan\delta = \frac{A_1 \sin\phi_1 + A_2 \sin\phi_2}{A_1 \cos\phi_1 + A_2 \cos\phi_2}$$

multiple wave effect subposition of more than two sinusoidal waves $$y = \sum_i y = \sum_i A_i \cos(wt - kx + \phi_i)$$

$$C \cos\delta = \sum_i A_i \cos\phi_i \text{ and } C \sin\delta = \sum_i A_i \sin\phi_i$$

the sum over n sinusoidal components yields $$y = C \cos(wt - kx + \delta)$$

$$C^2 = \left( \sum_{i=1}^{n} A_i \cos\phi_i \right)^2 + \left( \sum_{i=1}^{n} A_i \sin\phi_i \right)^2$$

$$\tan\delta = \frac{\sum_{i=1}^{n} A_i \sin\phi_i}{\sum_{i=1}^{n} A_i \cos\phi_i}$$

let A be a physical property A which is measured repetitively yielding a series of eigenvalues operating on various states generating data a-an-1

$$xf(x) = 8(x)$$

$$\partial/\partial x f(x) = 8(x)$$

$$A = \partial/\partial x$$

$$Af(x) = 8(x)$$

$$A<S> = |S>$$

A plane traveling electromagnetic wave generating an electric field $$\epsilon = wq(t) \sin kx + p(t) \cos kx$$

where p(t) and q(t) are time dependent amplitudes each having the form $$p(t) = q(t) = -\epsilon_o \sin wt$$

The correspond time dependent momentum and position for the oscillator of unit mass
where $q(t) = q_o \cos - wt$
and $po = qow$
$p(t) = q(t) = -po \sin wt$
The energy of the field in terms of functions such as
$P = (\epsilon_o L)^{\frac{1}{2}} p$ and $Q = (\epsilon_o L)^{\frac{1}{2}} q$ to yield
$E = \frac{1}{2}(p^2 + w^2 Q^2)$
and position is determined by $H = \frac{1}{2}(p^2 + w^2 q^2)$
If the amplitudes are completed $$a(t) = (2\hbar w)^{-\frac{1}{2}}(wQ + iP) = (\phi)e^{-iwt}$$

$$a^*(t) = (2\hbar w)^{-\frac{1}{2}}(wQ - iP) = a(\phi)e^{iwt}$$

the positive field element is denoted by $$\epsilon(-) = i\left(\frac{\hbar w}{2\epsilon_o L}\right)^{\frac{1}{2}} [a^*(t)e^{-ikx}]$$

the negative field element is denoted by $$\epsilon(+) = i\left(\frac{\hbar w}{2\epsilon_o L}\right)^{\frac{1}{2}} [a(t)e^{ikx}]$$

the combining of two vector components momentum and position to form complex functions $$a(t) = (2\hbar w)^{-\frac{1}{2}} (wq + ip)$$

$$a^*(t) = (2hw)^{\frac{1}{2}} (wq - ip)$$

$$q = \left(\frac{\hbar}{2w}\right)^{\frac{1}{2}} [a(t) + a^*(t)]$$

$$p = i\left(\frac{\hbar w}{2}\right)^{\frac{1}{2}} [a(t) + a^*(t)]$$

the field energy in terms of $$E = 2\epsilon_o \int_o^L \epsilon(-) \epsilon(+) dx = \hbar wa^* a$$

where the oscillator energy reduces to $$H = \hbar wa^* a$$

$$<H> = 2 <\alpha|\epsilon(-)\epsilon(+)|\alpha> = 2\epsilon(-)\epsilon(+)$$

$$<H> =$$

$$2\left[i\left(\frac{\hbar w}{2}\right)^{\frac{1}{2}} \alpha^* e^{-ikx}\right]\left[-i\left(\frac{\hbar w}{2}\right)^{\frac{1}{2}} e^{ikx}\right] = \hbar w|\alpha|^2$$

The measurement of intensity I is related to the average energy $<H>$ carried over the alloted time interval $\Delta t$ is needed to detect $|\alpha|^2$ to a photon scanning complex with an area A $$I = \frac{1}{A} \frac{\Delta E}{\Delta t}$$

where $\Delta E = <H>$
coherent light $$I = \frac{1}{A} \frac{\hbar w <N>}{\Delta t} = \frac{1}{A} \frac{\hbar w |\alpha|^2}{\Delta t}$$

Upon simplification area A and time interval $\Delta t \Longrightarrow$ unity the intensity I is given by $$I = \hbar w|\alpha|^2 = \hbar w <N>$$

$$A = \begin{bmatrix} a_{11} & a_{12} & \ldots & a_{1n} \\ a_{21} & a_{22} & \ldots & a_{2n} \\ \ldots \\ a_{m1} & a_{m2} & \ldots & a_{mn} \end{bmatrix}$$

$$\epsilon = \begin{bmatrix} \epsilon_1 \\ \cdot \\ \cdot \\ \cdot \\ \epsilon_P \end{bmatrix}$$

$$[x = x \ldots xn]$$

$$\frac{dx}{dt} = \begin{bmatrix} \frac{dx_1}{dt} \\ \cdot \\ \cdot \\ \cdot \\ \frac{dxn}{dt} \end{bmatrix}$$

The mathematical expressions, derivations and the like which are to be disclosed in the foregoing forms the basis for the programs depicted in FIGS. 35 through 41, and are utilized in full accordance with the invention set forth herein below;

An estimate of the temperature of the target tissue as a function of time is necessary to give the observer data concerning the optimum pulse length. If the laser pulse is longer than the optimum pulse length, heat will be exhausted through dissipation to the surrounding region. When tissues are regarded as capacitance systems having a capacity to store energy for a finite period of time, and then radiating the same stored energy as heat, tissue damage can be avoided by controlling delivery of a given amount of energy for a predetermined time interval. Two cases involving heating are considered. In the first case, energy from a laser is considered to produce a rise in temperature in a cylindrical volume in the target and surrounding tissues, and that heat flows radially outward therefrom. In the second case, it is considered that there is an absorption upsurge in only a relatively shallow surface layer of the tissue being irradiated. The actual time necessary for the optimum pulse length falls between the estimates based upon the first and second cases.

Case 1: Absorption in a Cylindrical Volume

This case is predicated upon a radially gaussian distribution of laser energy given by $$I_{Laser} = I_o \rho - \frac{r^2}{2r_0^2}$$

Where r is an approximation of the radius of the laser spot, the heat diffusion equation in cylindrical coordinates is:

$$\nabla^2 T = \frac{\rho c}{K} \frac{\partial T}{\partial t}$$

Where

C = specific heat
K = heat conductivity
$\rho$ = density
T = (z,r,o,t).
If we assume $$\frac{\partial T}{\partial t} = \frac{\partial T}{\partial \theta} = 0, \text{ then } \frac{\rho c}{k}\frac{\partial T}{\partial t} = \frac{1}{r}\frac{\partial}{\partial r}\left(r\frac{\partial T}{\partial r}(r,t)\right),$$

and we may let $T(r,t) = -U^2 T(r)T(t)$.

The radial part is Bessel's i.e. with solutions:

$$T(r,o) = A(u) = Jo(ru)\rho - \frac{u^2 k}{\rho c}$$

We require $$att = o, T(r,t = u) = To\rho - \frac{r^2}{2ro^2}$$

A (U) is selected to make the solution match the i.e. using a Fourier-Bessel transform.

From Watson we get $$T(r,t) = r_o^2 \int_0^\infty rfo(v,r)\rho - \left(\frac{kt}{\rho c} + \frac{r_o^2}{2}\right)r^2 dv$$

To estimate the time necessary for the dissipation of a heating effect we set:
$T(r,t)/T(r,o) = \frac{1}{2}$ at $r = c$ this reduces to $2Kt/r^o\rho c = 1$ or $$t = \frac{1}{2}\frac{r_o^2 \rho c}{k}$$

In the second case it is assumed that complete energy absorption will initially take place at the surface and neglect the radial dependence of the laser energy:

$$\frac{\partial T}{\partial r} = \frac{\partial T}{\partial \theta} = 0$$

The heat diffusion equation becomes upon separation of variables:

$$\frac{1}{T(Z)}\frac{\partial^2 T(z)}{\partial Z^2} = -U^2 = \frac{1}{T(t)}\frac{\partial T}{\partial t}\frac{\rho c}{k}$$

This has solutions of the form:

$$T(z, t) = A(v) \cos(v, z)\rho - \frac{rkt}{\rho c}$$

For initial conditions we choose: $T(o,z) = T_o U(Z_o - z)$. Where $$U(Z_o - z) = 1, o < z < Z\rho$$
$$= 0, z \geq Z_o$$

This means that energy is deposited in a layer of thickness Zo, i.e., that T(Zo) = (constant) × (energy in laser pulse). A solution may be obtained by assuming $T(Z,t=0) \cong \delta(z)$.

We again require A(v) to match the i.e.:

$$T(o,z) = \int_0^\infty A(v) \cos(v,z) dv$$

so that $A(v) = \frac{2}{\pi} \int_0^\infty T(u,z) \cos(u,z) dz$ $$T(z,t) = \int_0^\infty A(u) \cos(u,z) \rho - \frac{uztk}{\rho c} du$$

$$= \frac{To}{\Sigma} \sqrt{\frac{\rho c}{nkt}} \int_0^{zo}\left\{\rho - (x+z)^2\frac{zpc}{4kt} 1 - \right.$$

$$\left. \rho - (x-z)^2 \frac{\rho c}{4kt}\right\}$$

The solution at z = 0 reduces to:

$$T(o,t) = \frac{zTo}{\sqrt{r}} \int_0^{zo} \sqrt{\frac{\rho c}{4kt}} \rho - v^2 dv$$

$$= T\rho rf\left(zo\frac{\sqrt{\rho c}}{4kt}\right)$$

From tables, the time required for the temperature to drop to 52% of its initial value gives us the condition:

$$\frac{1}{2} = Zo\sqrt{\frac{\rho c}{4kt}}$$

or $$t = \frac{Zo^2 \rho c}{K}$$

estimated surface absorption dt for 52% init.

The fluid dynamics of the departicalization procedure and the effects of indirect joule heating on boundary zones, such as vessel walls, infusiate, and associated structures, are as follows.

The fluid temperature is regarded as having a uniform ambient temperature until a sudden alteration in thermal continuity occurs due to joule heating. The laser emission source provides joule heating and a maximum flow rate which can be achieved in a relatively short distance from the emission's source. The maximum flow rate which can be exacted from an initial static condition, which results from an occlusion obstructing the flow rate from 25% to 99+%, is a velocity which is essentially parabolic (laminar flow).

Figure 49:
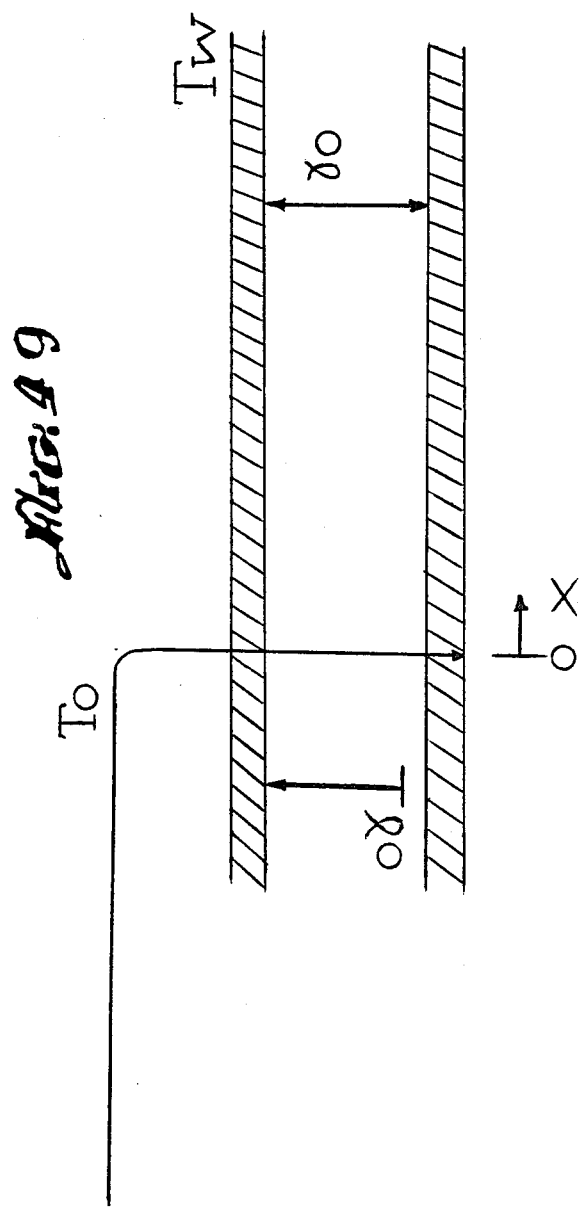
FIG. 49 denotes how a sudden discontinuity such as a blood clot can be depicted schematically.

A sudden discontinuity, such as a blood clot, can be depicted schematically as shown in FIG. 49.
Velocity $$U(\eta) = U\max\left(1 - \frac{\gamma^2}{\gamma o^2}\right)$$

where U max is the centerline velocity i.e. $\gamma=0$, $U=U$ max, $\gamma o=$radius of the tube.

The governing equation utilized to describe the surrounding fluid medium adjacent to and surrounding the clot is:

$$U\frac{\partial T}{\partial x} = \frac{\alpha}{\gamma}\frac{\partial}{\partial r}\left(\gamma\frac{\partial T}{\partial \gamma}\right), \gamma = \frac{K}{\rho cp},$$

Here, the fluid in contact with the clot is an aqueous preparation of buffered isotonic saline in distilled water.
K=conductivity
$\rho$=density
Cp=heat capacity.
The boundary conditions are:
    at $X \leq o$, $T=To$
    at $X > o$, $T(\gamma o,x)=Tw$ The solution is $$T^*(\gamma^*,x) = \sum_{\eta To}^{\alpha} Cnfn(\gamma^*)\rho - 2\lambda^2 nx^*$$

$$T^* = \frac{Tw - T}{Tw - To}, \gamma^* = \frac{\gamma}{\gamma o}, x^* = \frac{x}{(2\gamma o)RePy}$$

where $$Rc = \frac{U\max \gamma o}{\left(\frac{\mu}{\rho}\right)} = \text{Reyn. Number}$$

and $Pr = \frac{Cp\mu}{k} = $ Prandh Number $$= -\gamma^*\frac{\partial^2 fn}{\partial\gamma^{*2}} + \frac{\partial fn}{\partial\gamma^*} + \lambda_n^2\gamma^*(1-\gamma^{*2})fn = o,$$

fn(o)=1 for simplicity, and force fn (1)=o to satisfy the wall temperature condition $T^*(1,X^*)=o$:

$$Cn = \frac{\int_0^1 o\gamma^*(1-\gamma^{*2})fnd\gamma^*}{\int_0^1 \gamma^*(1-\gamma^{*2})fnd\gamma^*}$$

The boundary conditions fn (1)=o and fn (o)=1 are satisfied only for certain discrete values of $\lambda n$. the eigen values are the graetz functions fn. (The values of various constants of $\lambda n$ are given in standard tables).

An explicit equation for developing tube velocity is given by the following:

$$\frac{U}{U\max} = (1-\gamma^{*2}) - \frac{\alpha}{\eta}\sum_{\eta=1}^{\infty}\frac{8Jo(\lambda n\gamma^*)}{\lambda^3 nJ_1(\lambda n)}\exp\left(-\lambda_n^2\frac{vt}{\gamma o^2}\right)$$

Temperature profiles at various Prandh numbers for developing tube velocity may be obtained in standard works, such as F. M. White, "Viscous Fluid Flow." Here it is assumed that when an occlusion is completely eliminated, the flow rate will return to normal as long as the walls of the vessel maintain their integrity.

A normalized innovation process employed in accordance with the invention as set forth hereinbelow.
Discrete System:

$$x(k+1)=\Phi x(k)+GU(k)+\gamma w(k)$$

$$z(k)=Hx(k)+V(k), K=0,1,\ldots$$

$$E(W(t)WT(T))=Q\delta(t-r), E(v(t)V^T(T))=R\delta(t-r)$$

Normalized Innovation Process $$V = (HPH^T + R)^{-\frac{1}{2}}(z - H\hat{x})$$

$$\hat{x}(k+1) = \Phi\hat{x}(k) + Gu(k) + k(k)vk$$

$$[V(k+1)V^T(k)] = (HP(k+1)H^T + R)^{-\frac{1}{2}}(z(k+1) - H\hat{x}(k+1))(z(k) - H\hat{x}(k))^T$$

$$(HP(k)H^T + R)^{-\frac{1}{2}}$$

$$Z(k+1) = Hx(k+1) + V(k+1) = H(\Phi x(k) + Gu(k) + \gamma w(k)) + V(k+1)$$

$$Z(k+1) - H\hat{x}(k+1) = H\Phi\tilde{x}(k) + H\gamma W(k) + V(k+1) - Hk(k)[HP(k)H + R]^{-\frac{1}{2}}[z(k) - H\hat{x}(k)]$$

$$= H\Phi x(k) + H\gamma W(k) + V(k+1) - Hk(k)\Sigma^{-\frac{1}{2}}[Hx(k) + v(k)]$$
$$= (H\Phi - Hk(k)\Sigma^{-\frac{1}{2}}(k)H)\tilde{x}(k) + H\gamma W(k) + V(k+1) - Hk(k)\Sigma^{-\frac{1}{2}}(k)v(k)$$

$$E\{[z(k+1) - H\hat{x}(k+1)][z(k) - H\hat{x}(k)]^T\}, \Sigma(k) = HPH + R$$

$$E\{[(H\Phi - Hk(k)\Sigma^{-\frac{1}{2}}(k)H)\tilde{x}(k) + H\gamma W(k) + V(k+1) - Hk(k)\Sigma^{-\frac{1}{2}}(k)v(k)][H\tilde{x}(k) + v(k)]^T\}$$

$$= [H\Phi - Hk(k)\Sigma^{-\frac{1}{2}}(k)H]P(k)H^T - Hk(k)\Sigma^{-\frac{1}{2}}(k)R(k)$$

$$= H\Phi P(k)H^T - Hk(k)\Sigma^{-\frac{1}{2}}(k)(HPH + R(k)) = H\Phi PH^T - Hk\Sigma^{-\frac{1}{2}}\Sigma$$

$$= H[\Phi P(k)H - K(k)^{\frac{1}{2}}\Sigma] \therefore k(k) = \Phi PH\Sigma^{-\frac{1}{2}}$$

The secondary joule heating effects due to thermal exchange between the fluid medium and a given arterial or veinous wall can be expressed. The functions of fn are characteristic solutions to in order to have the expected value of zero.

A more elementary expression is needed to describe the radiant exposure of an emission source which impacts on each unit area of a target site. Let RE represent the energy impacting per unit area of a target site, H targ., such that $$RE = \int_0^T H\text{ targ. } dt,$$

which will give a value in joules/cm. The value H targ.$=\partial U/\partial t$, which has a value in watts per joule-second. U in the expression is equivalent to $$U = \int_0^T N dt$$

which gives a value in joules. (N is the number of watts delivered in a cylindrical volume per a given time interval.)

The case of deploying an energy source for the purpose of illuminating a given area, as performed in diagnosis, differs drastically from the process of departicalization or resectioning. The energy utilized to illuminate an area is described as the luminous energy. The term for luminous energy can be represented in the expression $$L = \int_0^T F dt,$$

which gives a value in lumen/sec or talbots. F in the expression is the luminous energy per unit time and is in fact measured in lumens such that $F=\partial L/\partial t$.

The simplified expression $E=\partial F/\partial A$ may be utilized to depict the luminous power reflected or transilluminated by a target site to a sensor array $$\left(\frac{\partial F}{\partial A} = \frac{\text{lumen}}{\text{meter}^2}\right).$$

The intensity or power per unit solid angle per unit source can be expressed in terms of $$I = \frac{\partial^2 F}{\partial A \partial \Omega} = \text{lumens/srm.}$$

The light images can be enhanced, electronically processed, and arranged in the form of an information matrix format.

Optical spectra signals and spatial temporal data information can be arranged, when digitized, into an information matrix in connection with analysis of laser light.

$$J = \delta\left[\left(\frac{\partial \ln L}{\partial b}\right)'\right] = \delta\left[\frac{\partial^2 \ln L}{\partial b \partial b'}\right]$$

J is designated the information matrix (Fisher)

$$Y = Ub + n$$

$$p(n) = \frac{1}{(2\pi)^{K/2} |N|^{\frac{1}{2}}} \exp[-\tfrac{1}{2}n'N^{-1}n]$$

An application of the Cramer-Rao inequality yielding the likelihood function.

$$L\{y;b\} = \frac{1}{(2\pi)^{K/2} |N|^{\frac{1}{2}}} \exp[-\tfrac{1}{2}(y - Ub)'N^{-1}(y - Ub)]$$

$$\ln L\{y;b\} = C - \tfrac{1}{2}(y - Ub)N^{-1}(y - Ub)$$

$$\frac{\partial \ln L}{\partial b} = +U'N^{-1}U$$

$$J = \delta[U'N^{-1}U] = U'N^{-1}U$$

the covariance is restricted to $$\text{Cov}[\hat{\beta}] \geq [U'N^{-1}U]^{-1}$$

For an a priori estimate of J, the expectation operator cannot be dropped; if u is a stochastic signal (n is white noise), then:

$$N^{-1} = \frac{1}{\sigma_n^2} I$$

and $$J = \frac{1}{\sigma_n^2} \delta[U'U],$$

$B=\{B_o,B_1\}$ in the case where $U_o$ & U, represents the same sequence of samples sifted in time over a single discrete sampling interval $$\delta[U'U] = k \begin{bmatrix} \psi uu(0) \psi uu(1) \\ \psi uu(1) \psi uu(0) \end{bmatrix} = K\sigma_u^2 \begin{bmatrix} 1 & P \\ P & 1 \end{bmatrix}$$

the minimum covariance is given by $$\text{cov}[\hat{\beta}] = \frac{\sigma_n^2}{K\sigma_u^2} \frac{1}{1-P^2} \begin{bmatrix} 1 & -P \\ -P & 1 \end{bmatrix} = c \begin{bmatrix} 1 & -P \\ -P & 1 \end{bmatrix}$$

for $p \neq o$ the off diagonal expression is equivalent to a correlation between errors $B_o$ $B_1$ and by means of a sample transformation, it is possible to observe the variance of the vector components $T\beta$;

$$T\beta = \frac{1}{\sqrt{2}} \begin{bmatrix} 1 & 1 \\ -1 & 1 \end{bmatrix} \begin{bmatrix} B_0 \\ B_1 \end{bmatrix} = \frac{1}{\sqrt{2}} \begin{bmatrix} B_0 + B_1 \\ -B_0 + B_1 \end{bmatrix} = Y$$

$$\text{cov}[\hat{Y}] =$$

$$\frac{c}{2} \begin{bmatrix} 1 & 1 \\ -1 & 1 \end{bmatrix} \begin{bmatrix} 1 & 1 \\ -P & 1 \end{bmatrix} \begin{bmatrix} 1 & -1 \\ 1 & 1 \end{bmatrix} = c \begin{bmatrix} 1-P & 0 \\ 0 & 1+P \end{bmatrix}$$

The continuous input of digitized signals is broken down into discrete matrix patterns which are reconverted into a series of overlapping fields, forming a single image of a given quadrant, in accordance with the foregoing. A program incorporating the foregoing controls the operation of the system and method of the invention, whereby the characteristics of laser light employed by the invention are controlled to perform the respective functions of non-invasive, non-destructive diagnosis and treatment of aberrant physiological conditions and sites.

In operation, the invention has two modes: diagnostic and surgical. In each of these modes, the system is computer controlled by use of programs based upon the mathematic formulation specified hereinabove.

In the diagnostic mode, doppler analysis of laser radiation reflected or re-emitted from the suspected aberrant target site is employed in order to obtain the chemical composition, molecular weight, concentration, dipole moment (if electrophoresis is used), and other characteristics of the suspected, aberrant site, for the purposes of diagnosis thereof.

Figure 35:
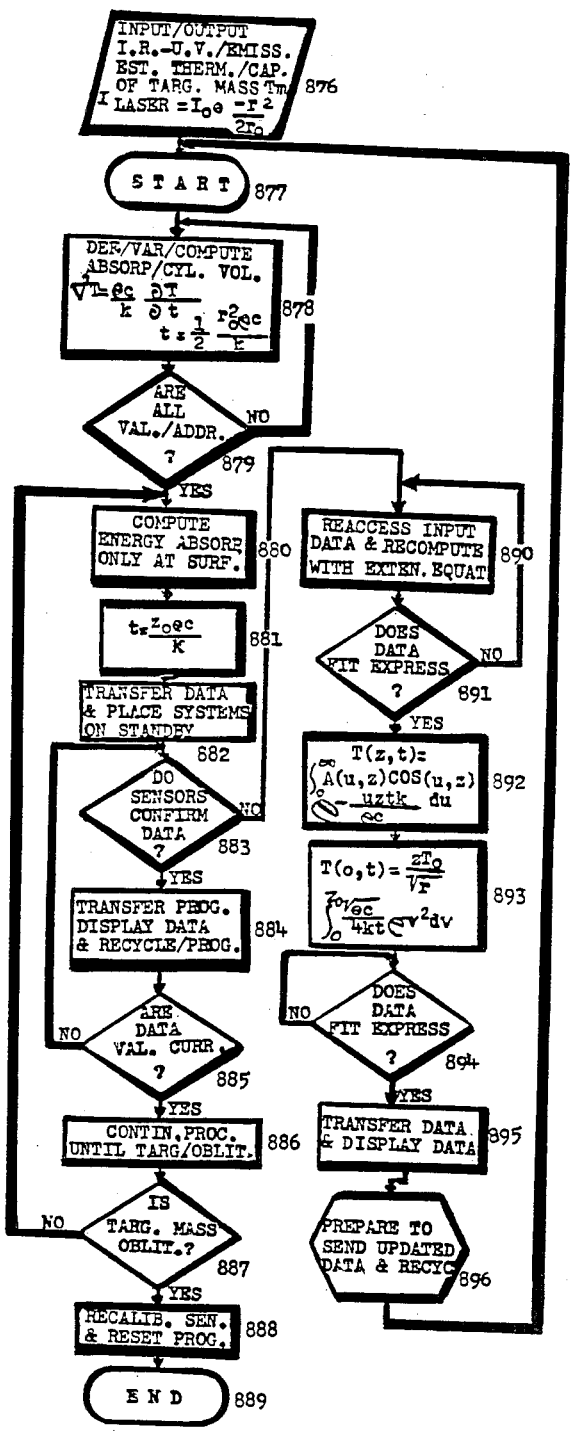
FIG. 35 depicts a flow diagram which represents a complex scanning process and data analysis procedure which is used for evaluating thermal capacitance of a given target mass.

FIG. 35 describes in brief a flow diagram outlining a complex program indicative of the scanning process and analytic procedure employed to specify the thermal capacitance of a given target loci. The data received from the input/output sensory array, number 876 utlilzes coherent radiation specifically to estimate the thermal capacitance of numeral 876 target mass, Tm, and the signals derived from actuating the start sequence. The start sequence number 877 enlists a process mode numeral 878, which defines various conditions if absorption occurs at the surface in a cylindrical volume, whereby all values of $\Delta^2 T$ and t are computed. The data from 878 is then conveyed to element 879, where it is determined whether or not all values are addressable. If the data is addressable, then the data is channeled to numeral 880, or reconveyed to the start sequence 877, if a negative response is elicited. Numeral 880 makes provisions to compute energy absorption only at the surface. The time necessary for a given target site, Tm, to radiate or re-emitted excess thermal energy incurred by laser bombardment is computed by numeral 881. The data from numeral 881 is transferred to element 883 by numeral 882, which also places the system on standby. Element 883 evaluates whether or not the data is confirmed by sensors. If the sensors confirm the data, then the data is conveyed to number 884 from element 883. If however, the sensors do not confirm the data, then the output from element 883 is shunted to numeral 890 for computation. Numeral 884 is wherein the program is transferred, the data is displayed and the program undergoes recycling. The data derived from 884 must be current and available, which is established by element 885. If the data values are deemed not current by element 885, then the said data is recycled to elements 883 for sensor confirmation. If data values are deemed current by element 885, then the laser emitter controller, the coupler unit, is ordered to commence and continue bombardment of a said target until target mass, Tm, is obliterated as described by numeral 886. Confirmation of target disintegration or departiclization is established by element 887. The data output undergoes sensor recalibration and the entire program is reset, as noted by numeral 888, if a positive response is elicited by element 887. The data from numeral 888 sends a signal which terminates the entire program sequence as described by number 889. Data which cannot be verified by element 887 is shunted back to the main program sequence at the level of numeral 880. As denoted earlier unsubstantiated information from element 883 is shunted to numeral 890, wherein the data is reaccessed and recomputed with extended equations. The data from numeral 890 is conveyed to element 891, where it is determined whether or not the data fits a specified expression. If a negative response is elicited by element 891, then the data is recycled back to numeral 890 for further specification. If however, the data elicits a positive response by element 891, then the data is conveyed by numerals 892 and 893, which computes values of T(z,t) and T(o,t). The computational parameters are set by a subroutine that ultimately attempts to compute surface absorption in the form of a first order differential rather than the more complexed second and third order equation, $t = Zo^2 pc/k$, which is the initial time it takes for the temperature of the target, Tm, to drop to approximatly 52% of the energy level supplied by the initial emissive bombardment. Element 894 confirms whether the data does indeed fit the mathematical equation, several of which are available and are chosen on the basis of closest approximation or best fit. The data from element 894 is then transferred to numeral 896 via numeral 895, which also displays data. It is in numeral 896 that a preparatory operation is enlisted to send up dated data to be recycled to the mainsequence program, re-entering at the start sequence level which is denoted by numeral 877. The data recycled from numeral 896 supplements new sensory data, which enters continuously and provides signal differentiation from the prior state of target Tm, and the present thermal kinetic state of the same said target.

Figure 36:
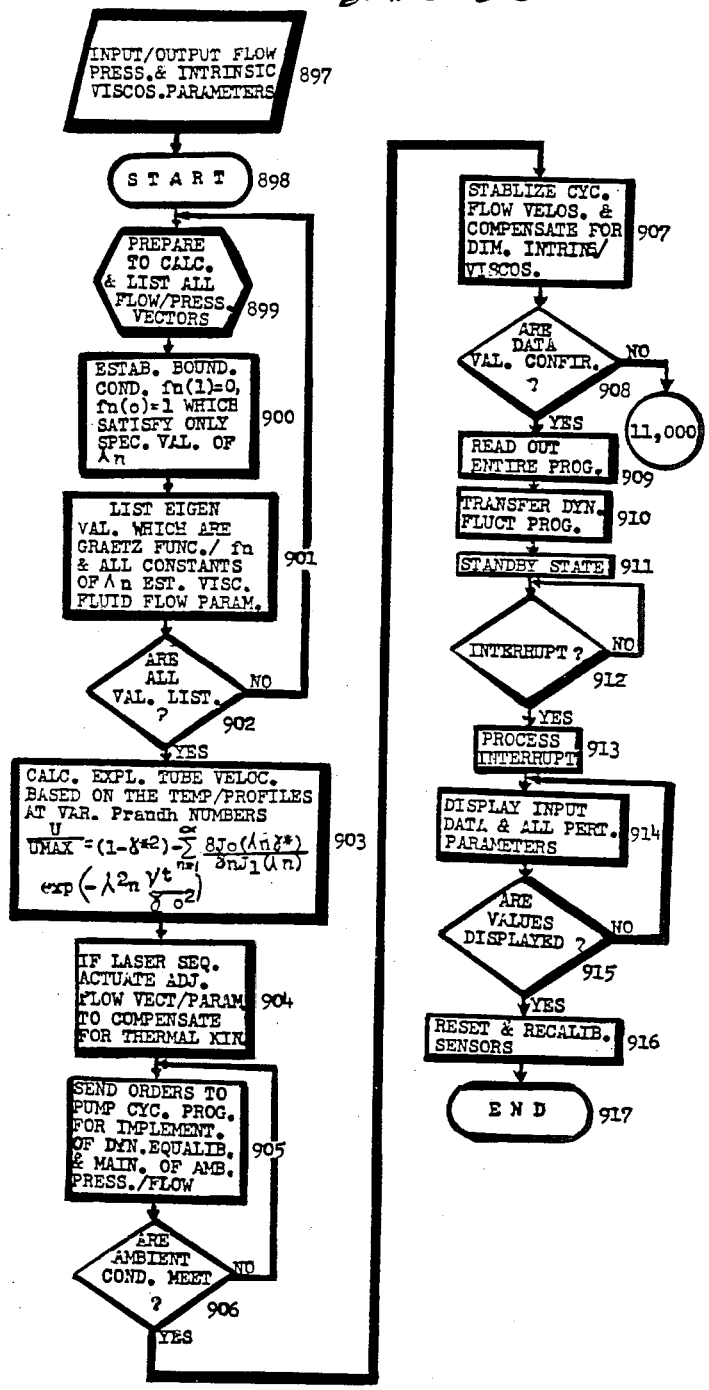
FIGS. 36 and 37 consist of flow diagrams which entail a continuous compensatory program to maintain ambient flow dynamics.
Figure 37:
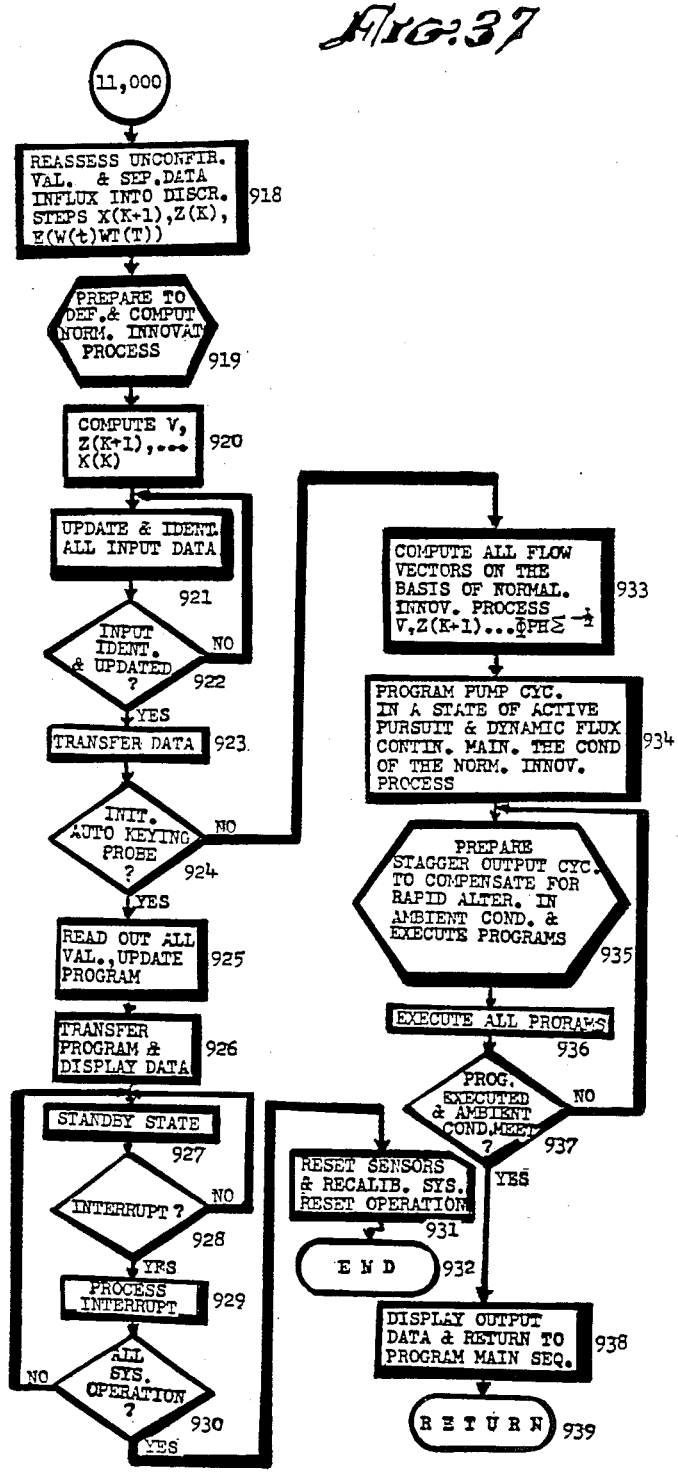

FIGS. 36 and 37 are flow diagrams which essentially provide a program to calculate and maintain ambient conditions of pressure, flow velocity, and to some extent thermal kinetic parameters of the infusiate. Catheter bound sensors specify the flow, pressure, and intrinsic viscosity parameters, as indicated by numeral 897. Numeral 897 actuates start sequence 898 and numeral 899 is a preparative operation necessary to calculate and list all flow pressure parameters. The boundary conditions are established fn (1)=o and fr (o)=1, which statisfy only specific values of λn is prescribed by numeral 900. The data from numeral 900 is then conveyed to numeral 901, wherein all specified eigen values are computed and listed, and the values are Graetz function fn and all constants of λn in order to provide the parameters necessary to estimate the dynamic flow and viscosity. Element 902 establishes whether or not all values are listed. If the values are unsubstantiated by element 902, then the data is recycled to the start sequence. If however, all values can be substantiated by element 902, the data is then conveyed to numeral 903. The calculation of explicit tube velocity which is based on the variance in temperature profiles at various Prandh numbers, and in so doing calculates all current values of U/UMAX; as prescribed by numeral 903. It is in numeral 904, wherein if a laser sequence is actuated the thermal kinetic parameters which are generated by the said transmission are computed, such that compensatory commands are directed towards the pump means. The command signals from numeral 904 are conveyed to numeral 905, wherein orders are sent to the pump means in order to implement its cycle program to adjust or compensate for disturbances in flow vectors, pressure gradients, or thermal kinetic fluctuations. The data from numeral 905 is channeled to element 906, where it is determined if ambient conditions are met and irregardless of whether the conditions are met initially the data output is conveyed to numeral 907. A negative response elicited by element 906 prescribes that the data be recycled and re-enters the system at the level of numeral 905. Numeral 907 denotes a subroutine which stabilizes cyclic flow velocities and compensates for diminished intrinsic viscosity and like processes. Element 908 establishes whether or not values can be confirmed by feedback sensors. If confirmation occurs at the level of 908, then the data is channeled to numeral 909. However, if the data is unconfirmable, then it is shunted by element 909 to numeral 918. Numeral 909 reads out the entire program which has been implemented and or is ongoing, and supplements the dynamic fluctuation program, which is transferred from number 909 to numeral 914 via numeral 910. While the data is undergoing transferal the entire system is placed in a standby state denoted by number 911. The standby state is followed by interrupt verification and process interrupt, which is denoted by element 912 and process numeral 913. The data is displayed and all pertinent parameters are presented, such that the user is made aware of and can act on present conditions. Element 915 assesses whether or not the necessary values are displayed. If the values are not displayed then the data is recycled for a signal verification, and it re-enters at number 914. The data which has been confirmed by element 915 sends a data signal, which resets and recalibrates all sensors as indicated by numeral 916. This occurs prior to program termination, as denoted by numeral 917.

FIG. 37 as described earlier is a continuation in part of FIG. 36 and it acts in a manner to instruct the aspiration infusion pump means act in compensatory fashion in order to correct deviations in the ambient conditions, which are caused by the laser departiclization process. If the data values are not confirmed by element 908 of FIG. 36, then the data is conveyed by element 918 of FIG. 37 as indicated by numeral 11,000. Nuneral 918 is indicative of a process wherein unconfirmed values are separated, re-evaluated and then re-entered in the form steps X (K,1), Z (K), E (W(t) WT (T)). Numeral 919 depicts a preparatory operation to define and compute data in terms of a normal and innovative processes. Number 920 is a computation process wherein V,Z (K+1)... and K (K). Numeral 921 is a step whereby all data is identified and updated. The data is confirmed on the basis of identification and is continuously being updated, as noted by element 922. Unconfirmed data is returned to be reprocessed by numeral 921. The data undergoes positive confirmation from element 922 and is then transferred to element 924, via numeral 923. Element 924 determines whether or not an auto keying probe is available. If a positive confirmation occurs in the data from element 924, then it is conveyed to numeral 925. However, if the auto keying probe is unavailable then the data from 924 is conveyed to numeral 933. A subprogram which reads out all updated values is provided by numeral 925. The program is then transferred and displayed, as indicated by numeral 926. The program is placed in a standby state described by numeral 927, as the data is displayed, in order to be viewed by the user. The standby procedure is followed by an interrupt and process interrupt, which is denoted by numeral 928 and 929. Element 930 assesses whether or not all systems are operational. If all systems are deemed operational then the sensors are reset, the entire system is recalibrated and all operative modes are reset as prescribed by numeral 931, prior to program termination as denoted by numeral 932. Numeral 933 is a process which denotes a procedure, in which all flow vectors are calculated on the basis of a second normalization innovation process V,Z (K+1)... $\Phi PH\Sigma - \frac{1}{2}$. It is in numeral 934 wherein the pump cycle is placed in an active pursuit state, following a programmed variation of the innovative process maintaining ambient conditions in the presents of dynamic flux. Numeral 935 denotes an operative process, where the pump cycle output is staggered in a specified linear stochastic operative mode. This in turn like the innovative process acts in a compensatory manner as to rapidly make correctional alterations in the flow parameters and like processes, such that the present set of conditions correspond to those of the said ambient condition. Number 936 executes all programs of the operative mode prepared by numeral 935. Confirmation of whether or not a program is executed in a sufficient manner is indicated by element 937. If a negative condition is elicited by element 937, then the data is sent back to 935 for further supplementation. However, if an affirmative response is indicated by element 937, then the data is displayed and returned to the main program sequence for further implementation, as noted by numeral 938. The data from 938 returns to the main computer complex as denoted by number 939, for further analysis and programming instructions.

Figure 38:
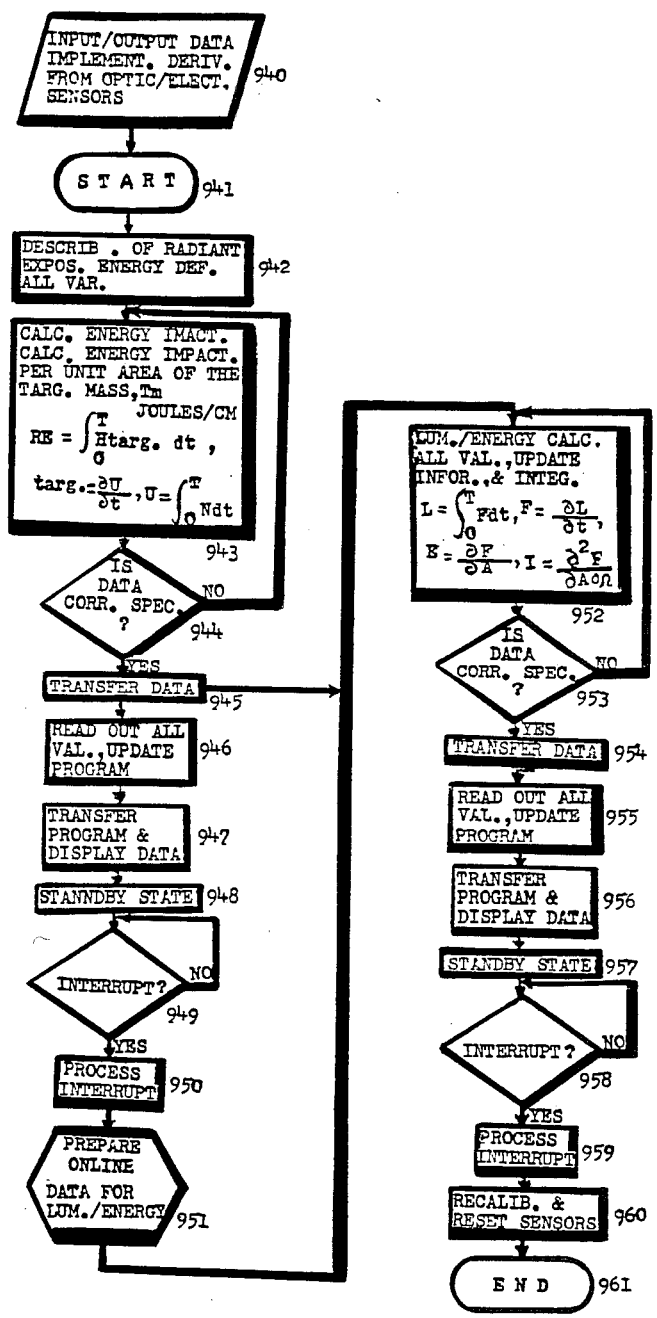
FIG. 38 initially details a flow diagram specifying a program which computes the radiant energy and or luminosity of emission sources as well as that reflected back by the target mass.

FIG. 38 initially details a flow diagram specifying an ancillary program which computes the radiant energy, and or luminosity of specified emission sources, as well as those specific emissions reflected back from a target mass. Numeral 940 is indicative of the continuous input/output data implementation derived from optical electronic sensors, which actuates the start sequence denoted by numeral 941. The radiant exposure energy and all variables therein are defined by number 942. Numeral 943 calculates the energy impact per unit area of the target mass Tm at a specified time interval, computing both RE and target variance. Element 944 discerns whether or not the data specification is correct or not. Unsubstantiated information re-enters the main sequence from element 944 at the level of 943. If data confirmation occurs at element 944, then the data is transferred from element 944 to numeral 946 by numeral 945. It is in numeral 946 wherein all data values are read, updated, and made available to the user. Program and data is displayed to the user as indicated by numeral 947. The entire program is momentarily placed in a standby state, which is denoted by numeral 948. A momentary interrupt verification and process interrupt is denoted by numbers 949 and 950 respectively. Numeral 951 denotes a preparatory operation which involves online sequencing of data for computation of luminosity energy ratio. The sequenced data is channeled from numeral 951 to numeral 952. Numeral 952 calculates all values, updated information and integration of L, F, E and I. Element 953 ascertains whether or not the data is in a form deemed correct. The data is ultimately transferred from element 953 to numeral 955, by the process, which is denoted by numeral 954. The data is once again read out and the program is updated by ancillary processes, as indicated by numeral 955. The program is transferred and the data is displayed, such that the accumulative information is made available to the user in the form of an interactive graphics system, as denoted by numeral 956. Numeral 956 is then followed by an initial standby mode or state number 957, and an interrupt verification/process interrupt, which is described by numbers 958 and 959 respectively. If all conditions of the program have been satisfied then a data signal exiting from numeral 959 enters a signal processor and compiler, which automatically resets and recalibrates all measuring sensors concerned with the program prior to the termination of the said program, as indicated by numerals 960 and 961.

Figure 39:
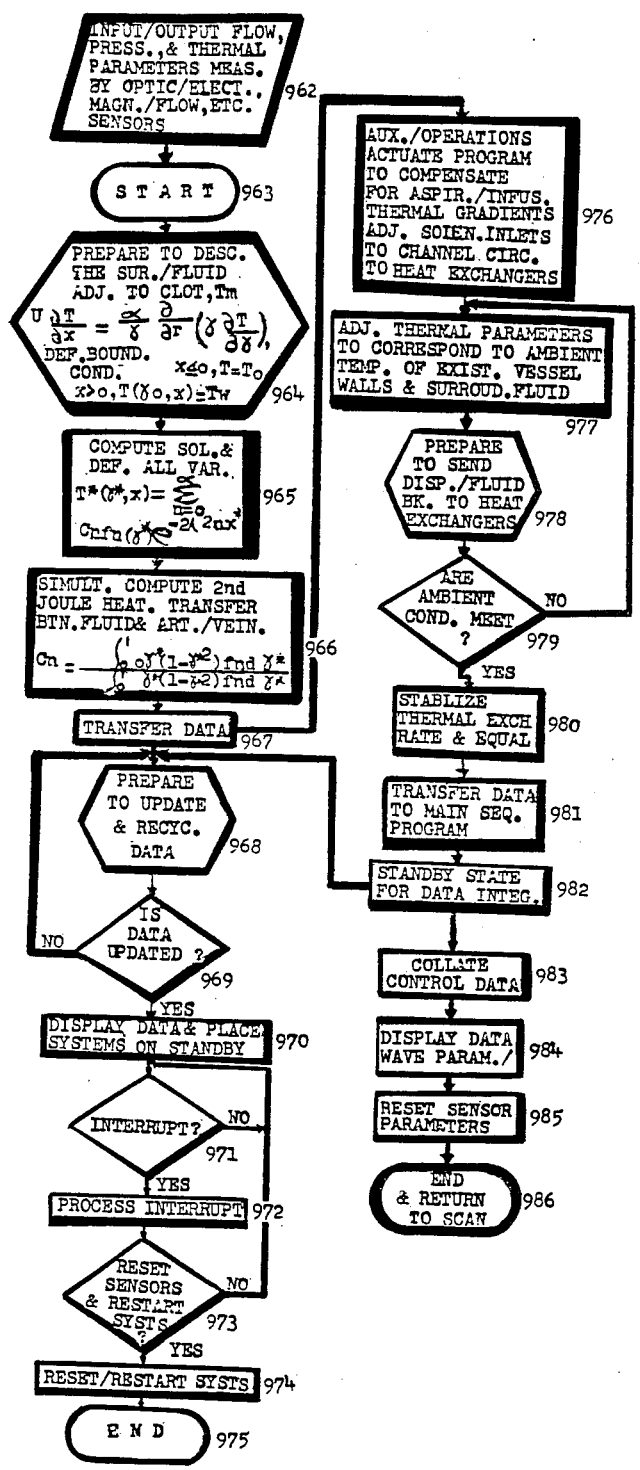
FIG. 39 is a flow diagram specifying a program which calculates flow, pressure and thermal parameters and rectifies offsets in these parameters.

FIG. 39 depicts a flow diagram specifying a program which calculates various flow, pressure and thermal kinetic parameters and provides the framework to effectively counter unwanted disturbances in the above mentioned parameters. Input/output flow, pressure and thermal kinetic parameters are measured by an optical electronic means, and is then conveyed with alternate equivalent data which is obtained by magnetic flow meters, radio frequency sensors, audio acoustical generators and the like, which in turn form the basis of the program actuator, as denoted by numeral 962. Numeral 962 actuates the start sequence which is described by number 963. Once the start sequence is actuated a data signal is conveyed from numeral 963 to numeral 964. Numeral 964 is a descriptive operation which prepares a detailed analysis of the surface fluid surrounding or adjacent to a target site defined as clot Tm. All necessary boundary conditions U $\partial T/\partial x$, To, Tw and the like are also described within the framework of number 964. It is in numeral 965 where the solution to all variables involving $T^*$ ($\gamma^* X$) are computed. It is in numeral 966 wherein simultaneous computations occur for secondary joule heating effects, due to heat conduction between known differential fluids, such as the infusiate and various structural vaults, such as veins, arteries, or other conduit structures, which are all collectively described by the C n term. Data specifications are transferred from numeral 966 to numeral 968 via numeral 967. The data is updated and recycled in the preparatory mode indicated by numeral 968. Element 969 assess whether the data is updated or not, and once confirmation has occurred the data from element 969 is then conveyed to numeral 970. Numeral 970 allows the user to be informed by enhanced color graphics and acoustics, all of the foregoing processes mentioned herein the above, while the system is placed on standby offering the user a chance to reply. Element 971 and numeral 972 are indicative of the typical interrupt verification process interrupt process, for sensory reset and recalibration. Element 973 assess whether or not the sensors are reset, and if the subsystems are in a restart sequence. Numeral 974 is a process wherein sensors are reset and the entire system is put on alert, which elicits an auto keying stage that initiates the start sequence prior to the programs first termination point, as prescribed by numeral 975. Data is then transferred from numeral 968 to numeral 976. Numeral 976 denotes a subprogram and subroutine wherein auxiliary operations are employed in order to actuate a subprogram, which compensates for aspiration/infusion thermal kinetic gradients to adjust the solenoid inlets to channels, where the contents are circulated to heat exchangers that dissipate excessive residual heat, until ambient conditions are met. Numeral 977 is a subroutine which adjusts thermal parameters to correspond to ambient temperatures of existing vessel walls and the surrounding fluid medium. Number 978 is a preparatory operation which sequentially conveys displacement fluid from the region of the target site back to the heat exchangers. Element 979 verifies whether or not the ambient conditions are met. An affirmative response conveys data from element 979 to numeral 980, whereas a negative response recycles data to element 979 and back to 977. Numeral 980 is a process which stabilizes the thermal exchange rate and maintains dynamic equilibrium. The data is transferred to the main sequence program, as indicated by number 981. Numeral 982 provides for a standby state for the entire program and data integration, divergently channeling information to numerals 968 and 983. Numeral 983 collates control data and further signals command. The data is displayed with information concerning wave parameters and the like, which is to be scanned by the user, as described by numeral 984. After the data is displayed the sensors are automatically reset as indicated by number 985, which occurs prior to the secured termination sequencer, as denoted by number 986. Number 986 sends a data signal which returns the program to the scanning mode.

Figure 40:
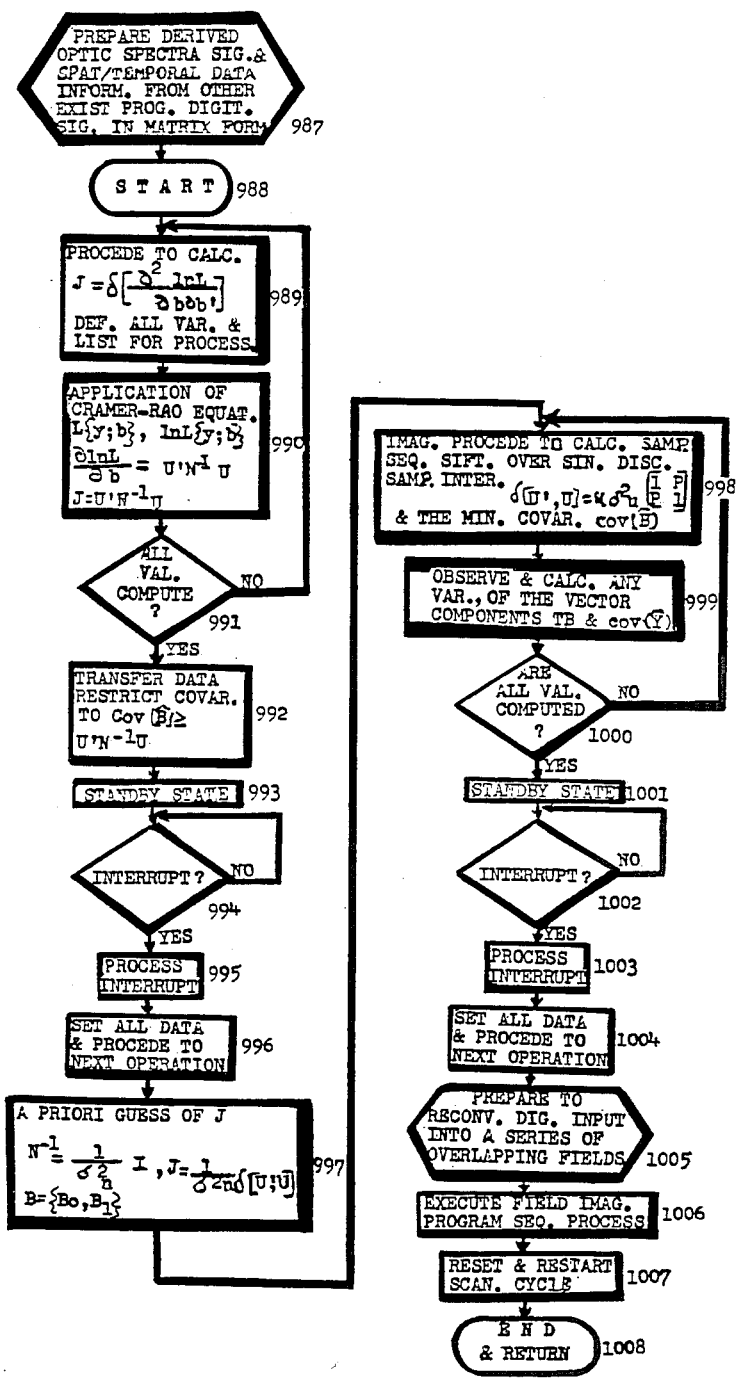
FIG. 40 is a flow diagram calling for a program which sequences optical electronic data to form optical fields and is based on the Maximum Likelyhood Method.

FIG. 40 is a flow diagram which calls for a program which sequences a number of separate optical electronic data matrices in order to form larger more unified optical fields, which are based on the Maximum Likelihood Method. Numeral 987 depicts a preparatory operation, wherein optical spectra signals and spatial temporal data along with other information from exiting programs are put in a digitized signal matrix form. Numeral 988 denotes the programs start sequence. Numeral 989 denotes a process estimates J and defines all variables, listing all appropriate values. Numeral 990 specifically applies the Cramer-Rao Equation which is utilized in order to describe L $\{y;b\}$; in $\{y;b\}$, $U'N^{-1}V$ and the like. Element 991 verifies whether or not all values are computed, and irregardless of the inital response the data is then conveyed from element 991 to numeral 992. The transferal of data from element 991 to numeral 996 is propagated by numeral 992. Numeral 992 is a process not exclusively limited to transferal, but is also adds supplemental data which then restricts the covariance, such that $T\gamma \; Cov[\hat{\beta}] \geq U'N^{-1} V$. While computations are enlisted by numeral 992 the entire program is put in a standby state, as denoted by numeral 993. A typical recovery period is utilized for data supplementation in order to give enough time for other priority systems to conduct their specific programming, as denoted by the interrupt verification, indicated by element 994 and numeral 995. Numeral 996 denotes a transitory process whereby all data is set, and the program or system is now readied to procede to the next phase of the operation. Numeral 997 defines an operation which makes a priori guess of J. The operative data obtained from numeral 977 is conveyed to numeral 998, wherein the uniformed coding and collation of smaller sampled optical fields are properly sequenced to form a single optical field in the form of an enhanced mosaic. The process of sequential imaging is an integrated digitized process described in brief by the value of $\delta[U', U]$, minimum covariance and the like. Numeral 999 describes a process whereby observable and calculated vectors, or the vector components of $T\beta + Cov \; (\overline{Y})$ are observed and calculated. Element 1000 assess whether or not all values are properly computed. If all values are properly computed, then the system is put in a normal standby mode as denoted by numeral 1001. However, if numerical values are accessible then the data is reconveyed to a point of entry, which corresponds to numeral 998. From the standby mode numeral 1001 the system enters a typical interrupt/process interrupt sequence, which is denoted by number 1002 and 1003. All data is effectively set and the programmed is commanded to go on to the next phase of its operation by the process of a compiler, which is described by numeral 1004. Operative process number 1005 prepares to convert each digitized optical electronic input field into a series of overlapping four dimensional image matrices and tend to collate the field data in order to form a single unified optical field. It is in numeral 1006, wherein the field imaging sequencing program is executed. The sensors are reset and the necessary restart cycle is engated for the digitized numeric scanning cycle, which is denoted by numeral 1007. Once numeral 1008 has completed its process then the program signal automatically terminates the program, and returns to the main computer complex for further instructions.

Figure 41:
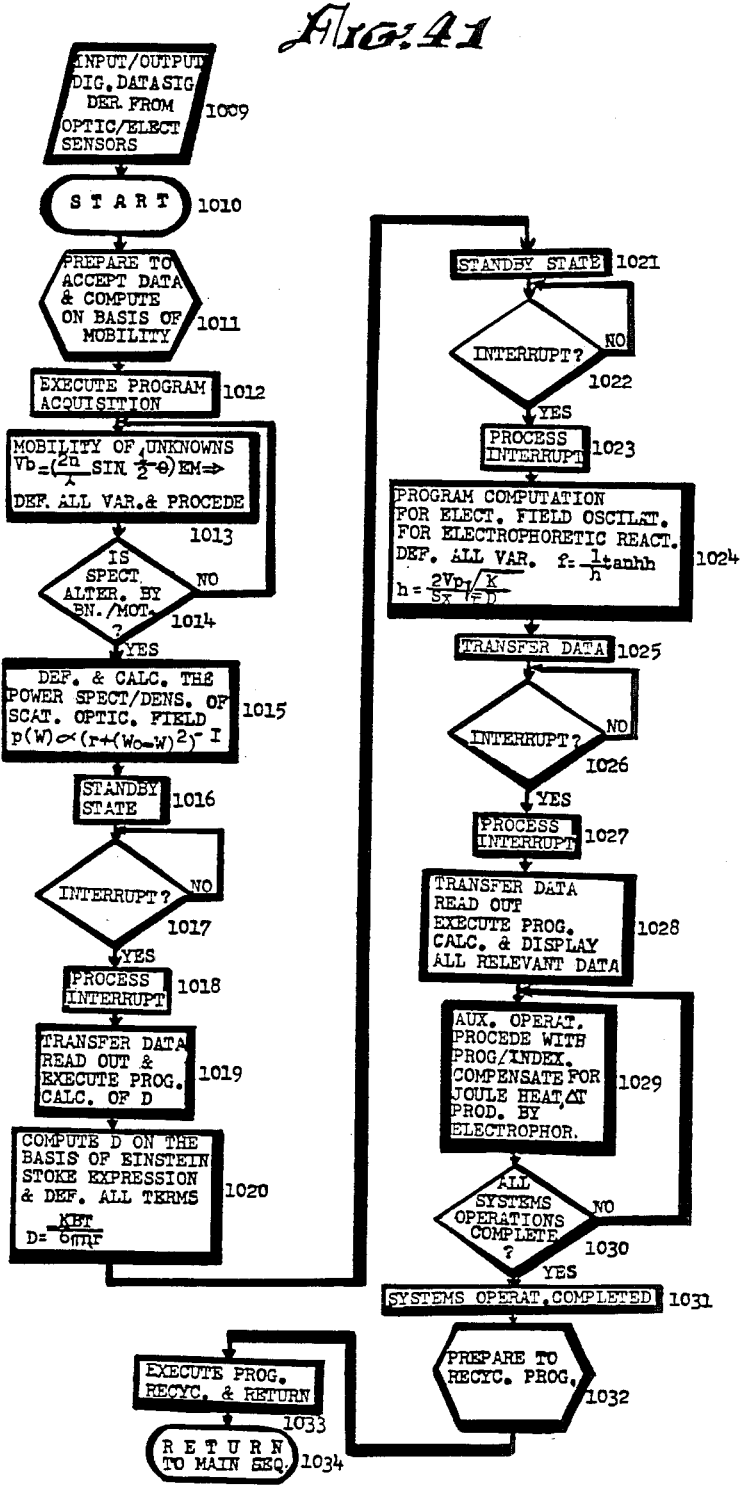
FIG. 41 details a flow diagram which provides a program for computing the mobility of unknowns in a tight optical electronic field.

FIG. 41 details a flow diagram for computing the mobility of unknowns in a tight optical electronic field. Numeral 1009 denotes digitized data input/output sequence obtained from optical electronic sensors, which collectively actuates the start sequence denoted by number 1010. Numeral 1011 depicts a preparatory operative mode, which readily accepts data and computes the type and number of species on the basis of their mobility. The actual acquisition program is executed at the level of number 1012. Numeral 1013 is wherein the mobilities of unknowns are computed, and all variables are defined, as tracking procedes in the active operative mode. Element 1014 assesss whether or not spectral characteristics are indeed altered by its motion in an oscillating charged field. If an affirmative response is elicited by element 1014, then the data is sent to numeral 1015 for further processing; and if a negative response is elicited, then the output data from element 1014 is recycled to the main sequence. Numeral 1015 describes an operative mode, which defines and calculates the power spectral density of local scatters with the specified optical field p (W). Numerals 1016, 1017 and 1018 denote a standby state, interrupt/process interrupt subsequence typically employed for the recovery period and time sharing, which was disclosed earlier in regards to the preceding figures. Numeral 1019 preferably transfers data, provides read out and executes a specific program for the calculation of D. It is in numeral 1020, wherein D is computed on the basis of the Einstein Stoke expression $D = KBT/6\pi I\eta$ and the specifications of all terms therein. Numbers 1021, 1022 and 1023 denote once again the typical recovery interval and time sharing period, whereby a system standby state is followed by the interrupt verification and process interrupt. Numeral 1024 denotes a program computation for electric field oscillations for electrophoretic reactions defining all variables f, h, and the like. A transferal mode denoted by numeral 1025 conveys data from numeral 1024 to 1028. An interrupt sequence and verification are denoted by numbers 1026 and 1027. The data is once again transferred as indicated in numeral 1028; but in this case it is to a higher order operative function, wherein data read out and the execution of the specified program occurs, while the values are being calculated and the said data is being displayed, such that all relevant data concerning the doppler shift and electric mobility of given chemical species are continuously displayed. Numeral 1029 consists of an auxiliary operation which procedes with a program of indexing the said identified chemical species, while simultaneously adjusting electronic field pulse oscillations to compensate for the effects of joule heating due to electrophoretic activity. Element 1030 establishes whether or not all systems operations are complete, and once verification occurs, then the systems operations are all encoded and listed for complete recall, as denoted by number 1031. Numeral 1032 is a preparatory operation, whereby all encoded programs are recalled and recycled. The subprogram controlling recycling is implemented as described by numeral 1033; and once the operation is completed all data derived from the said program terminates itself, and then sends the data back to the main sequence of the program as indicated by numeral 1034.

Figure 42:
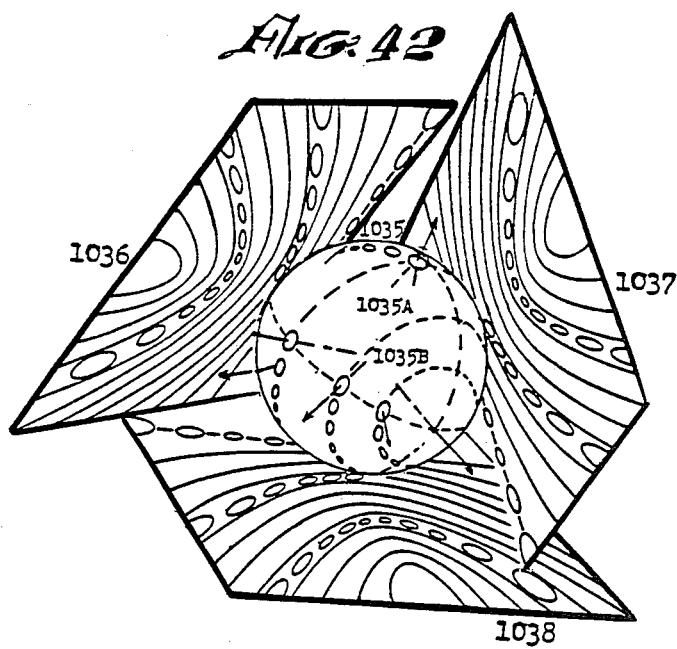
FIG. 42 is a graphical representation of a charged droplet suspended in an oscillating electromagnetic field.

FIG. 42 is an enhanced graphical representation of a charged droplet suspended in a tight electromagnetic field which is undergoing doppler analysis. The charged droplet designated by numeral 1035 is depicted as a spheroid for simplicity, which has several differentially charged regions peripherally located and collectively designated by numbers 1035A and 1035B. The motion of the charged droplet is shown in real time and in relation to three spatial temporal plates denoted by numbers 1036, 1037 and 1038. Each plate is revealed undergoing spatial distortion due to the effects of the oscillating electronic field, and intrinsic displacement due to the specific properties of the said molecular droplet number 1035.

Figure 42A:
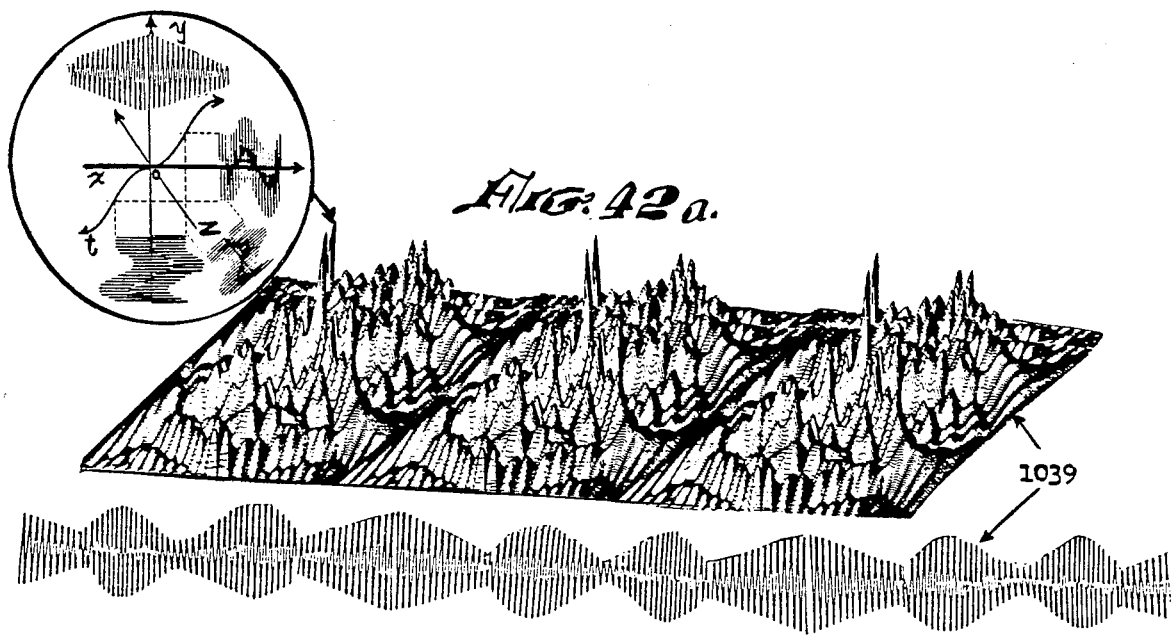
FIG. 42a is a complexed description of a four dimensional representation of a single wave tracing of a specified chemical species complex.

FIG. 42a consists of a typical single complexed four dimensional video image of the specified charged droplet, numeral 1035. Numeral 1039 depicts a series of binodal signals presented repetitively and each separated electronically by a linear sequencer. The four dimensional chain sequence depicted by numeral 1039 is the specific doppler signature of 1035.

Figure 42B:
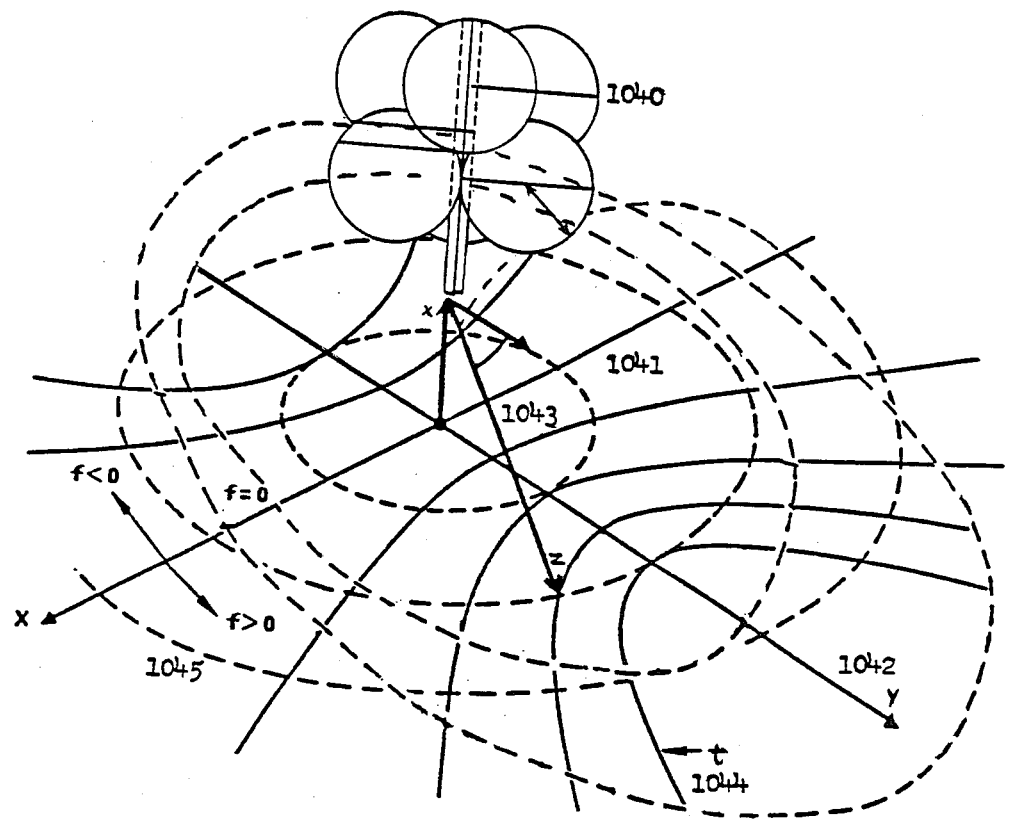
FIG. 42b is an illustration of a typical dispersal pattern produced by a cluster of charged droplets.

FIG. 42b depicts a series or cluster of droplets which have a single axial or nodal transmission point and generates numerous signatures. The common molecular cluster sharing a regional transmission point is indicated by numeral 1040. The spatial axial coordinates are represented by 1041, 1042 and 1043. The spatial temporal eliptical like displacement vectors which are elicited by the cluster, is denoted by number 1044. Numeral 1045 illustrates one of several electromagnetic fields generated by the cluster which as it rotates, radiates a repetitively signature signal, as denoted by the series of circular wave fields, indicated by the broken lines contained herein.

Figure 43:
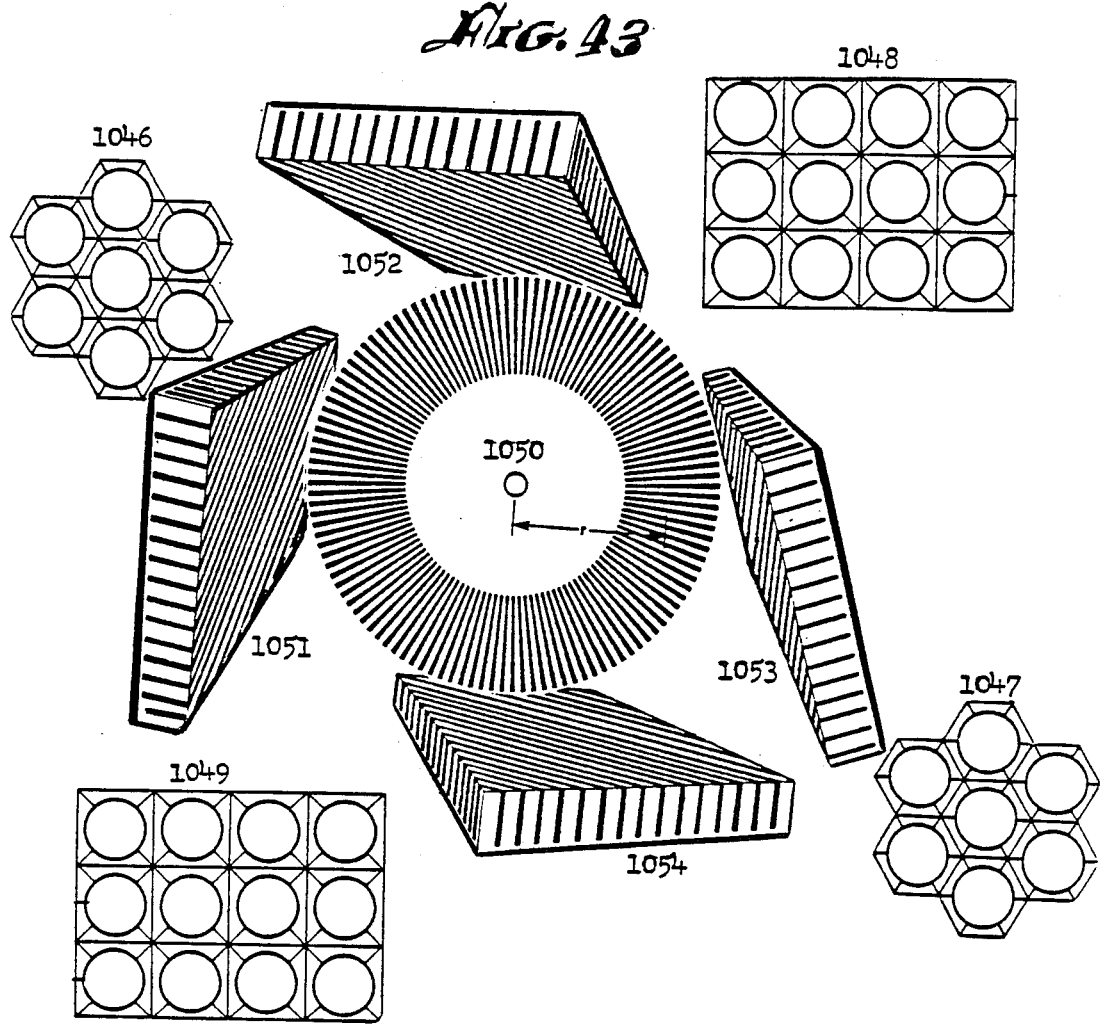
FIG. 43 graphically illustrates a cross-sectional view of an imaginary trilayered spheroid which is undergoing electronic oscillation.

FIG. 43 depicts an illustrative manner a cross-sectional view of trilayer spheroid consisting of lipids, fats and proteinoids caught in an electronic field. Numerals 1046 and 1047 represent geometrically a hexagonal arrangement of component parts from an outer membrane; whereas numerals 1048 and 1049 depict a rectangular lattice configuration of component parts from the same said membrane structure. Numeral 1050 represents the trilayered molecular membrane from a large spheroid structure. The outer layer consists of forward hydrophilic members which face the outer periphery, and with hydrophobic members which face the interior of the spheroid. A third nuclear membrane with a displacement radius r is also depicted in numeral 1050. The spheroid, 1050 is placed within the contexts of an oscillating electronic field, whereby its motion is set by intrinsic properties such as size, weight, charge and the like. The charge fields exerted by microelectrodes number 1052 and number 1054 provide vertical motion; whereas deflection plates 1051 and 1053 monitor an intrinsic molecular charge. The intrinsic molecular charge from the spheroid is shown graphically exerting pull on plate 1053.

Figure 43A:
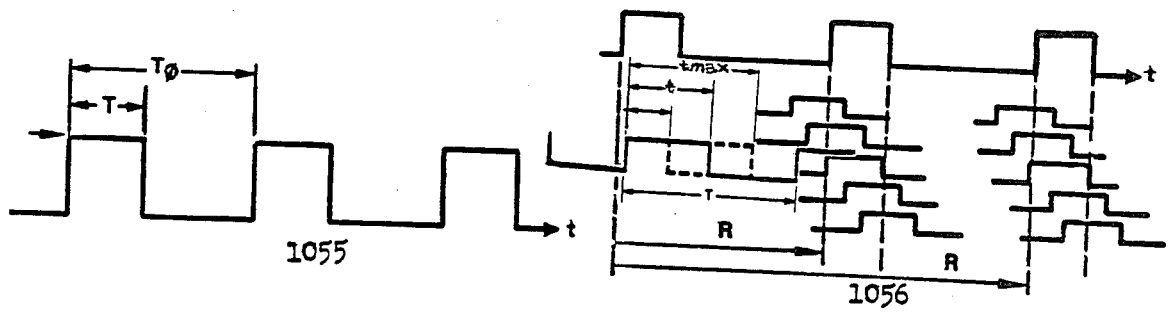
FIG. 43a depicts a series of typical signal tracing charts exemplary of the preferred embodiment.

FIG. 43a depicts in an illustrative manner simplified signal tracing charts, which are exemplary of those charts provided by systems operation in the preferred embodiment. Numeral 1055 is representative of a pulse spectrum, which scans targets at discrete frequencies or lines within the context of a spectral envelope. The signals derived from 1055 are not unlike radar signals which differ only in thier size magnitude and dimensions. $T\phi$ is equivalent to the interpulse or modulation period, which is equivalent to the pulse repetition interval. T is equivalent to the pulse, length or width and D equals the ratio of $T/T\phi$ or the duty factor. The average power being equivalent to the product of (D) (peak power). Number 1056 of FIG. 43a also reveals a single original transmit signal indexed against the return signal of the same transmit signal re-emitted from an ideal target. The step lines are graduated in close proximity and are produced by electronic modulation of the transmission beam, which produces a differential shift in the doppler spectrum. Not only the range and velocity of the said target can be computed, but the species verification or chemical composition of the target site can also be identified if enough transmission beams are indexed against reflected and or re-emitted emission from the same said target.

Figure 43B:
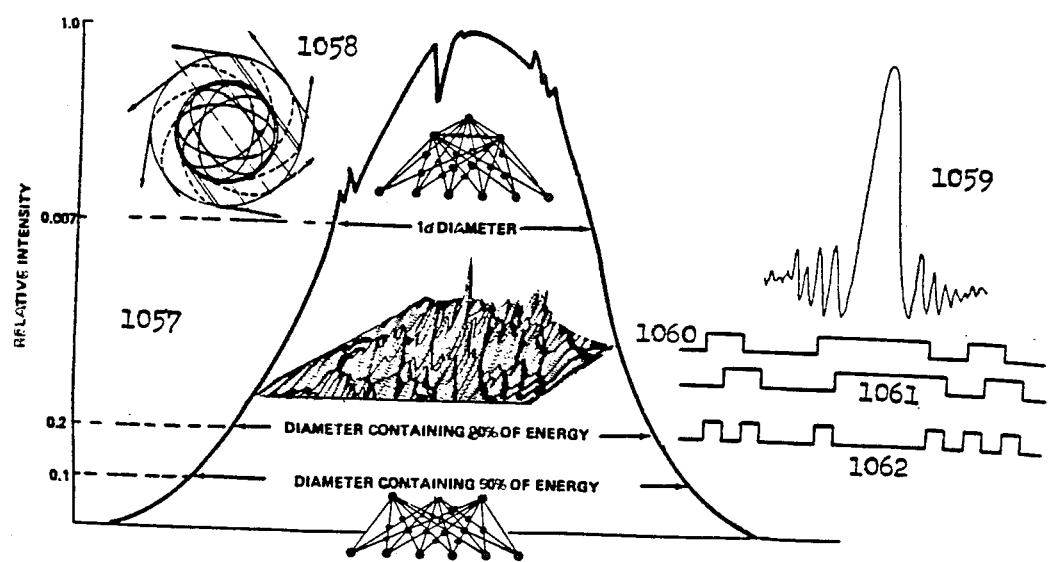
FIG. 43b describes graphically a typical energy distribution with the optimum pulse rate, and wave characteristics of the emissive fiber optics which are consistant with the preferred embodiment.

FIG. 43b depicts a typical energy distribution graph with its relative intensity fluxuations, optimum pulse rate, wave characteristics and the like. Numeral 1057 denotes a simplified version of a typical energy distribution. Over 90% of the entire energy output is contained within the confines of the first and third sigma values, as denoted by numeral 1058. Number 1059 describes in an illustrative manner the optimal transmission response needed to be exhibited by a single or group of optical fibers. The exact bandwidth frequency and wavelength values are initially omitted because they vary with the type of fiber optics means employed. It is for that reason, that a fiber optics means must be selected for its transmission capabilities for the given emission, or visa versa. There exists within the framework of the beam coupler device a vast quantity of encoded comparators and delay circuits, which are necessary to determine the doppler shift, or assess optical electronic wave characteristics, and or the like. In accordance with the entire complement of comparators, delay circuits and other readily commercially available components is a greatly simplified diagram of basic pulse width sequences. Numeral 1060 represents a typical input pulse stream, of which many are generated. Number 1061 is indicative of the same said input pulse described by 1060 however, it is delayed in time for the purpose of temporal differentiation. Numeral 1062 is indicative of a secondary pulse stream which provides a phase shift in the doppler spectra, if a spatial temporal separation is provided. The response time interval is variable ranging from one nanosecond to greater than one hundred nanoseconds, and it has a mean average of twenty-five nanoseconds.

FIG. 44 is a combination block diagram and a simplified schematic representation of only one of several equivalent optical electronic multiplexing stations associated with the preferred embodiment. Each electronic subsystem will be assigned a numerical equivalent and all pertinent component parts will be designated an alphanumeric value. Each and every component structure or equivalent structure is readily available commerical commerically from such sources as Hewette-Packard, Texas Instra. or other suitable manufacturers. A generalized version of a multiplex station is illustrated by 1063, 1064 denotes a logic gate. $\alpha 1$ is descriptive of a typical signal line, $\alpha 2$ defines the transmission line supply. Alphanumeric symbols $\alpha 4$, $\alpha 5$, $\alpha 6$ and $\alpha 7$, $\alpha 3$ collectively denote open collector outputs. $\alpha 8$ through $\alpha 13$ describes various resistive elements. The data is inputed via line $\alpha 14$ and $\alpha 15$ denotes an enable segment. The line status is denoted by $\alpha 16$. Numeral 1065 consists of two mutally exclusive or Flip Flop subsystems, as denoted by $\alpha 17$ and $\alpha 18$. Incorporated $\alpha 17$ is an independent wave interrupt sequence, whereas $\alpha 18$ consists of an exclusive or Flip Flop system with a Kalman filter. Numerals 1066 and 1067 consist of specially encoded optical electronic data output channels. Numerals 1069 and 1068 are indicative of a data influx channel with element 1068 being a data compression undergoing compression prior to systems entry. Numerals 1079 and 1071 describe two separate but equivalent block diagrams of a four chip hybrid receiver means, each of which act as separate wave discriminaters. Each digitized signal is analyzed on the basis of electronic wave characteristics $\alpha 19$ denotes the link monitor output VREF whereas $\alpha 20$ describes the ALC Amp and VREF. $\alpha 21$ is indicative of a negative peak comparator, whereas $\alpha 22$ is indicative of a positive peak comparator. The logic low and logic high comparators are denoted by $\alpha 23$ and $\alpha 24$. The differential amplifier stage and the gain control stage are described by $\alpha 25$ and $\alpha 26$. The bias voltage preamp described by $\alpha 27$ and $\alpha 28$ explains the D.C. restorer amp. Elements $\alpha 29$ through $\alpha 32$ depict resistors. The element $\alpha 33$ is representative of an R-S flip flop data output means. Numeral 1071, as previously noted is equivalent to numeral 1070 and therefore elements $\alpha 19$ through $\alpha 33$ are equivalent to elements $\alpha 34$ through $\alpha 48$. The present status of each signal enters element 1072, a mainline sequencer which sends its input data to a clock means, which is denoted by numeral 1073. The data processed by numerals 1072 and 1073 are collectively sent to numeral 1074 through numeral 1076, which consists of three equivalent short term storage multivibrator means. Numerals 1077, 1078 consists of a Kalman filter encoder means. Numeral 1079 depicts a biphasic line. The digitized electronic signals are converted into thier optical electronic binary equivalents, and is then sent to the main computer complex for further analysis, as noted by numeral 1080.

Figure 45:
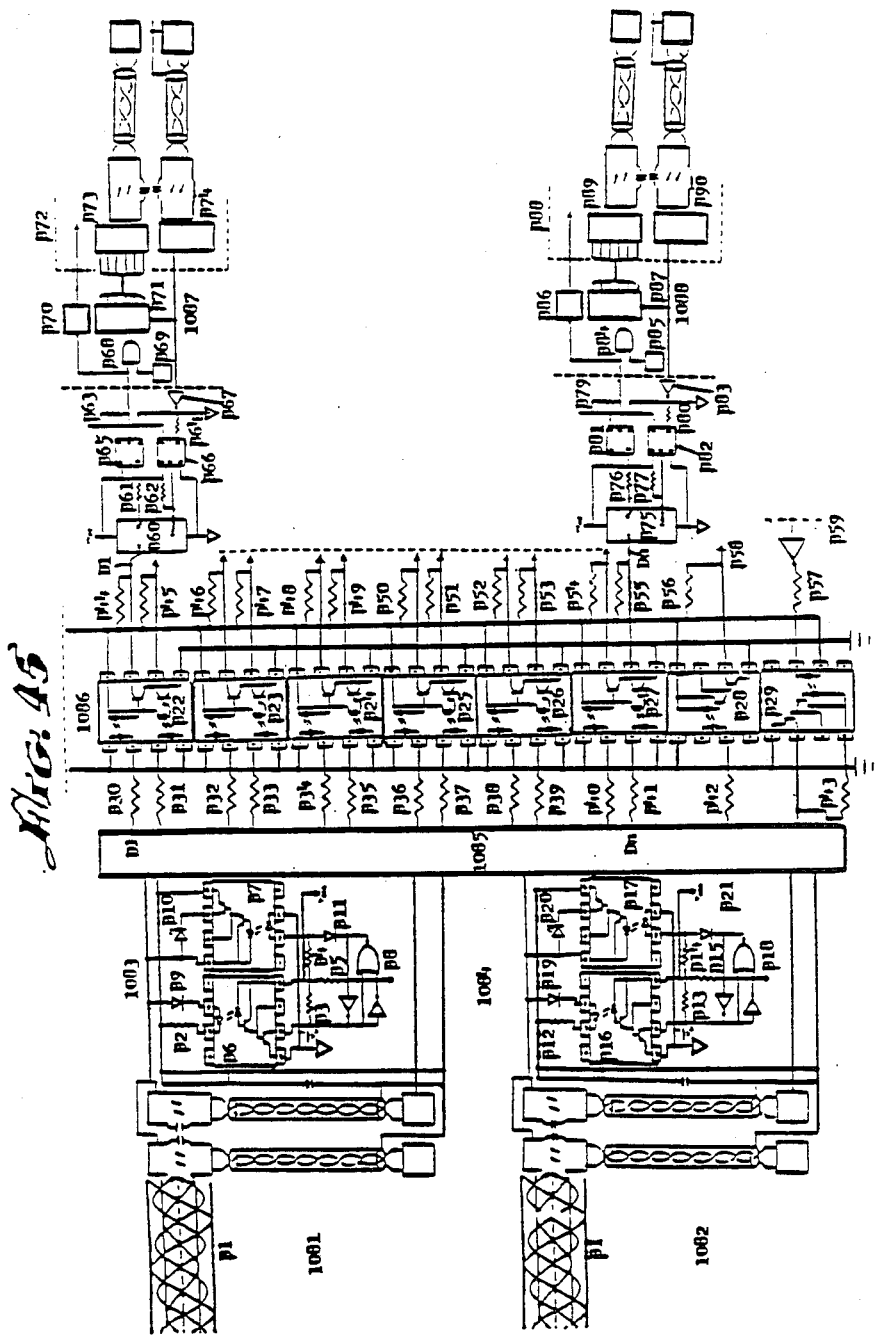
FIG. 45 depicts a combination block diagram and a partial schematic representation of an exemplary form of a single optical electronic analog/digital converter unit.

FIG. 45 depicts a combination block diagram and a partial schematic of an exemplary form of a single optical electronic analog/digital converter unit. FIG. 45 like that of FIG. 44 is composed entirely of commercially available components, each of which is assigned an alphanumeric value. Subsystems 1081 and 1082 are equivalent optical line driver and receiver means that receive a given transmission wavelength and or its referrence beams. Numerals 1083 and 1084 are equivalent and indictive of common optoisolators. The resistor elements of 1083 are denoted by $\beta 1$ through $\beta 5$. The accompaning optical electronic IC means is described by $\beta 6$ and $\beta 7$ respectively. The effective ground and logic element is described by $\beta 8$. $\beta 9$, $\beta 10$ and $\beta 11$ described other diode means, which are associated with the subsystem. Numeral 1083 is equivalent to numeral 1084, therefore all components of numeral 1083 are equivalent to those of 1082, such that components $\beta 1$ through $\beta 10$ are equivalent to components $\beta 11$ through $\beta 21$. Numeral 1085 represents an analog digital converter means IC $\beta 22$ through $\beta 29$ of numeral 1086, which describes the isolated analog/digital in terms of parallel data outputs. Components $\beta 30$ through $\beta 57$ denote resistor elements of numeral 1086 for the respective data outputs denoted by Di through Dn. $\beta 58$ denotes the start converter process, whereas $\beta 59$ describes the termination of the converter process. Each data output is received by a digital/analog isolator system, two of which are denoted by numbers 1087 and 1088. Numeral 1087 and 1088 are equivalent to one another, and to all similar such units. A multivibrator means of numeral 1087 is denoted by $\beta 60$. The resistive elements of subsystem 1087 are described by the alphanumeric values $\beta 61$ through $\beta 64$. There are two equivalent IC's denoted by $\beta 65$ and $\beta 66$. $\beta 67$ is indicative of a logic inverter, $\beta 68$ depicts a oscillator and $\beta 69$ denotes a logic AND gate. The one shot means is denoted by β70 and the clock counter means is described by β71. The microprocessor system is described herein by β72 with an input port denoted by β73 and an output port indicated by β74 component elements β75 through β90 of numeral 1088 are equivalent to those elements β60 through β74 of numeral 1087.

Figure 46:
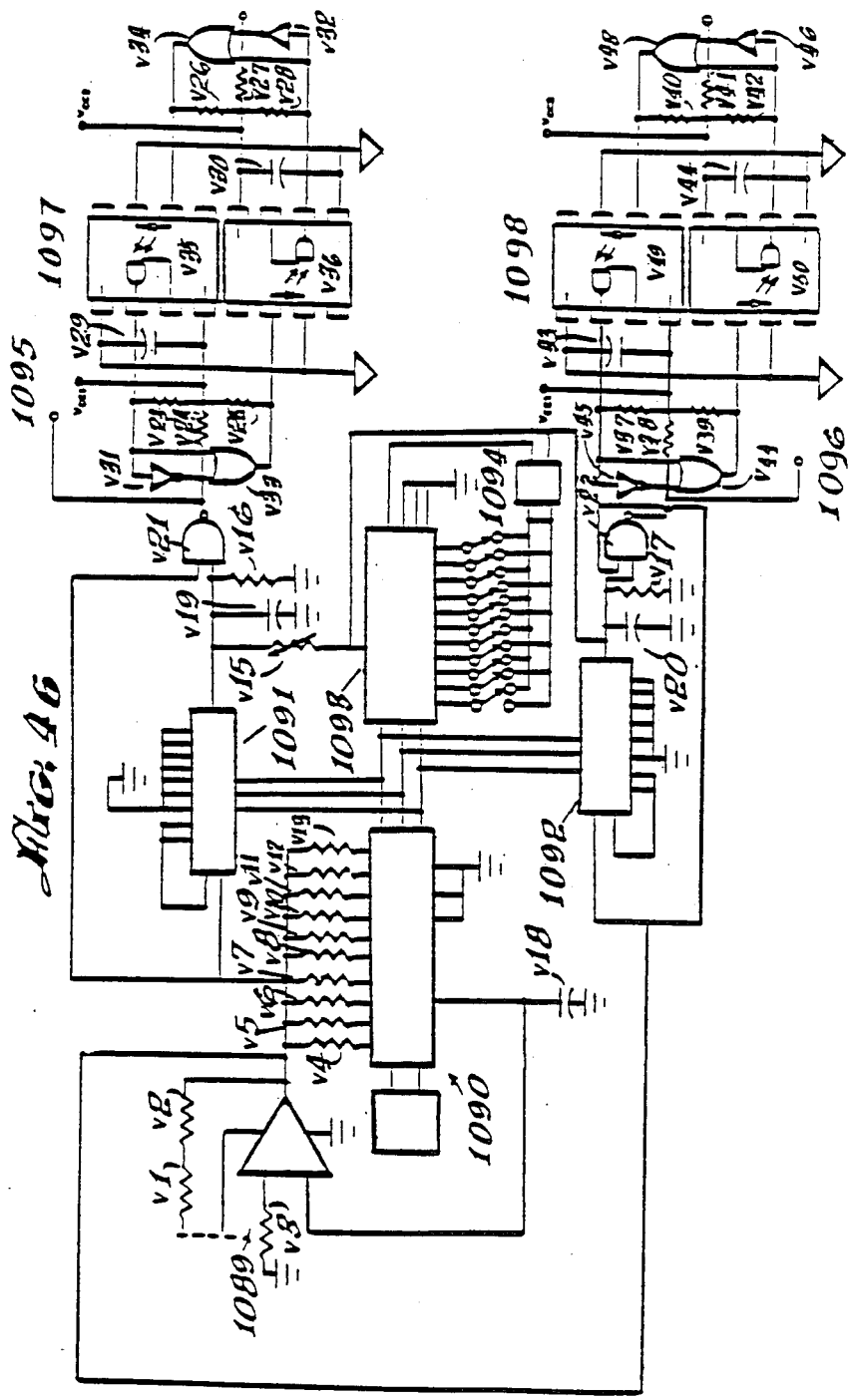
FIG. 46 is a generalized schematic of a multiple tone generator utilized by the coupler unit.

FIG. 46 is a generalized schematical representation of a multiple tone generator typical of one of several deployed by the coupler device. All component part depicted in FIG. 46 are commerically available. Numeral designations of the tone generating system proper are as follows: a basic voltage regulator or governor is indicated by numeral 1089. An analog multiplexer is described by numeral 1090 and two binary counters are indicated by numeral 1091 and 1092 respectively. The tone frequency generating IC is indicated by numeral 1093, which is adjacent to the key or switching elements, denoted by number 1094. The resistor elements are denoted by alphanumeric values V1 through V14 and the capacitors V15 and V17. The typical NAND (inverting AND) gate is denoted by V18 and V19. The frequency generated tone sequence can enter any one of four or all of the following systems denoted by numerals 1095 through 1098, which terminate in either a speaker system or equivalent piezoelectric means for audio sound to be preceived by the user. Normal tonal sequences are conducted through lines 1095 and 1096; whereas alternate tone sequence or tonal sounds are provided by high speed duplex systems, if specified by either the user or the main computer, via the keying means. Subsystems 1097 and 1098 are equivalent units. Numeral 1097 resistive elements are described by V20 through V25, whereas V26 and V27 denote the capacitance means. The invert means are defined by V28 and V29, whereas the logic or gate is designated by V30 and V31 respectively. The controlling IC s of 1097 are prescribed by V32 and V33. As mentioned earlier 1097 and 1098 are equivalent subsystems, therefore component V20 through V33 are equivalent to components V34 through V47.

Figure 47:
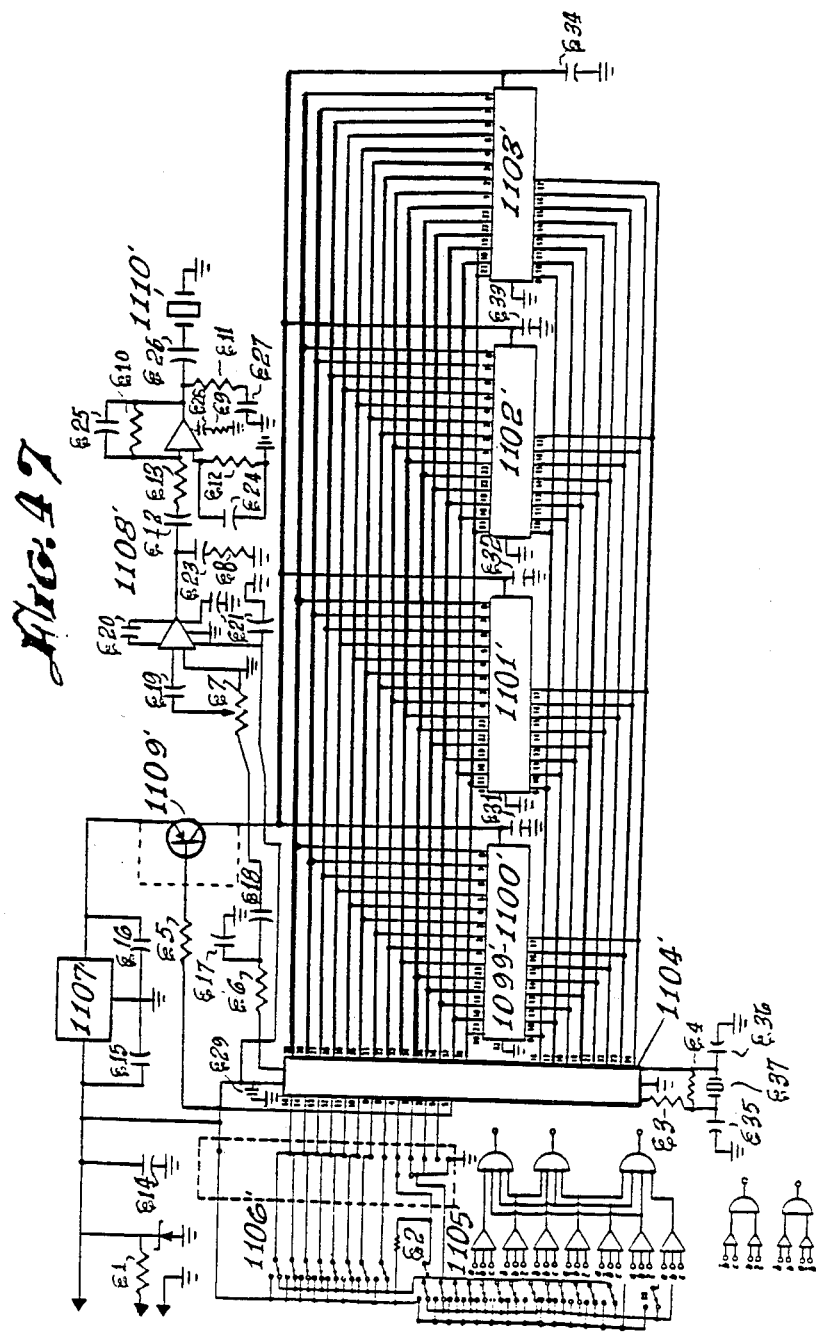
FIG. 47 represents a basic schematic of a modified electronic speech synthesizer, modified with extended vocabulary.

FIG. 47 is representative of a basic schematic of a modified electronic speech synthesizer, which is typical of the type deployed in the coupler device. The extended vocabulary is in excess of 1,000 words, and more than 20 phrases which is announciated in either a male voice, a female voice or both vocies. As with preceding figures all components are commercially available by such manufactures as National Semiconductor and others. Numerals 1099 through 1103 depicts equivalent speech ROM IC s which contain revelant speech data, whereas the IC denoted by numeral 1104 represents the actual speech processor. An encoder signal digitizer and auto keying complex is described by numeral 1105 and the manual keying sequencer is indicated by numeral 1106. The systems resistor elements are denoted by alphanumeric values ε1 through ε13 and the various capacitor components are noted by ε14 through ε35. Numerals 1106, 1107 and 1108 describe a typical voltage regulator IC and two audio amp IC chips. Numeral 1109 denotes a typical transistor element. ε36 denotes a crystal oscillator, whereas numeral 1110 describes a piezoelectric wafer which is utilized as a speaker means.

Figure 48:
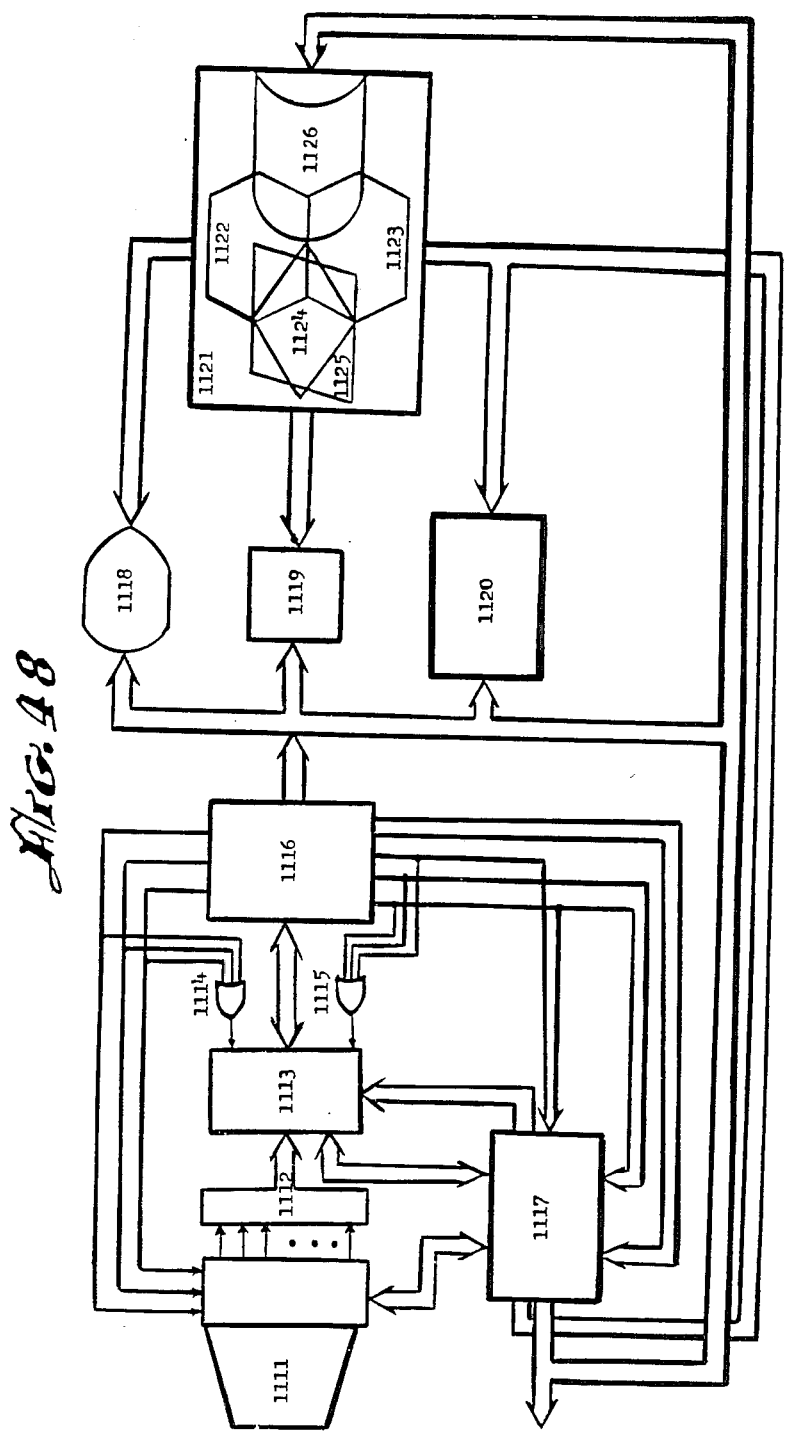
FIG. 48 denotes a simplified block diagram explicitly showing the effective position of both the tone generator and speech synthesizer relative to an enchanced computer system.

FIG. 48 denotes a simplified block diagram which explicitly shows the effective position of both the tone generator and speech synthesizer relative to an interactive computer complex. Numeral 1111 denotes a key matrix, numeral 1112 describes an encoder means and number 1113 indicates a multiplexer unit. Numbers 1114 and 1115 are illustrative of logic gates, whereas numeral 1116 describes a common signal condensing microprocessor means. Numeral 1117 defines a commercially available ROM, RAM and EEPROM means, such as the SDK86 and or its equivalent as described earlier in this disclosure. Numerals 1118, 1119 and 1120 describe a interactive graphics display terminal, a tone generator and a speech synthesizer as previously indicated in the body of this disclosure. Numeral 1121 through 1126 depicts the entire ancillary portion of the computer complex as denoted by numeral 1121, which has operative subunits described therein by numerals 1122 to 1126; which provide for a totatlly interactive expandable system, with a voice recognition and voice actuated computerized command program. The operative subunits overlap each other partially. Numerals 1122 and 1123 depict preparatory function where the data is processed. The data enters and exits the computer complex as illustrated by number 1124; whereas numeral 1125 is indicative of a decision process. The online storage means of the computer complex is described by numeral 1126.

Although the foregoing the embodiments were described by taking examples of the current state of the art coupler device, the present embodiment can be generalized to modified versions of the earlier coherent radiation beam coupler device or expanded versions of the same said present coupler device, or similar such apparatus which can be made in accordance with either of the above described embodiments, as readily apparent to those skilled in the art, and hence a detailed description thereof will be presently omitted.

Although the present invention has been illustrated in detail the scope of the present invention is to be interpreted to cover the application of all equivalent electronic, optical electronic, or manually operated devices rather than in a limiting sense. The invention and devised process forming the embodiment of the present invention are to be accorded the full scope of the claims appended hereto.

What is claimed is:

1. In a Coherent Beam Coupler System comprising a source of variable-wavelength laser light, automated beam-splitting means optically coupled to said source of variable-wavelength laser light and having a plurality of optical output channels, automated dye cell means optically coupled to said optical output channels of said beam splitting means to produce coherent light at predetermined wavelengths;

optical-fiber light transmission means coupled to said automated dye cell means for carrying laser light at selected frequencies to aberrant organic sites for bombardment of same;

combination sensor and fiber-optic networks for carrying light returned by said aberrant sites and analyzing the spectral content of such returned light;

infusate insertion means coupled hydraulically to said aberrant sites;

microelectrophoresis means hydraulically coupled to said aberrant sites for analyzing exudants therefrom; and digital computer and data storage means, having an operating program, coupled electronically to said source of laser light, to said automated beam splitting means, to said automated dye-cell means and to said infusate insertion means for controlling all of the foregoing in accordance with the interactive operating program of said digital computer and data storage means and coupled electronically to said combination sensor and fiber-optic network for receiving input information therefrom, as to conditions at said aberrant sites, the method of eliminating aberration at said aberrant sites, which includes the step of introducing to said aberrant organic sites, by way of said infusate insertion means, infusates of an amount and nature controlled by said digital storage and computer means in response to return signals from said laser-bombarded aberrant sites.

2. The method according to claim 1 which includes the additional steps of pre-storing in said digital storage and computer means digitized signals representative of returned light from organic sites with known physiological conditions, comparing digitized signals from said combination sensor and fiber optic network with said pre-stored digitized signals and generating control signals in said digital storage and computer means for application to said source of variable wavelength laser light to control the amplitude, frequency and duration of light emitted by said variable-wavelength laser light source, in accordance with the operating program in the digital storage and computer means.

3. The method according to claim 1 which includes the additional steps of pre-storing in said digital storage and computer means digitized signals representative of re-emitted light from organic sites with known physiological conditions, comparing digitized signals from said combination sensor and fiber optic network representative of re-emitted light from a laser excited organic site with said pre-stored digitized signals for analyzing aberrant chemical properties of the material making up the aberrant organic sites and for determining the nature and amount of the infusate introduced to said aberrant organic sites.

4. The method according to claim 3 which includes the additional step of generating control signals in said digital storage and computer means for application to said source of variable wavelength laser light to control the amplitude, frequency and duration of light emitted by said variable-wavelength laser light source, in accordance with the interactive operating program of the digital storage and computer means and the analyses of the chemical properties of the materials making up said organic sites.

* * * * *